United States Patent
Sill et al.

(10) Patent No.: US 8,524,784 B2
(45) Date of Patent: *Sep. 3, 2013

(54) POLYMER MICELLES CONTAINING ANTHRACYLINES FOR THE TREATMENT OF CANCER

(75) Inventors: Kevin N. Sill, Tampa, FL (US); Habib Skaff, Tampa, FL (US); Jonathan Rios-Doria, Land O Lakes, FL (US)

(73) Assignee: Intezyne Technologies, Incorporated, Tampa, FL (US)

( * ) Notice: Subject to any disclaimer, the term of this patent is extended or adjusted under 35 U.S.C. 154(b) by 193 days.

This patent is subject to a terminal disclaimer.

(21) Appl. No.: 12/915,446

(22) Filed: Oct. 29, 2010

(65) Prior Publication Data

US 2011/0142950 A1 Jun. 16, 2011

Related U.S. Application Data

(63) Continuation-in-part of application No. 12/771,676, filed on Apr. 30, 2010.

(60) Provisional application No. 61/178,630, filed on May 15, 2009, provisional application No. 61/174,160, filed on Apr. 30, 2009.

(51) Int. Cl.
*A61K 9/00* (2006.01)
*A61K 49/00* (2006.01)
*A01N 25/00* (2006.01)

(52) U.S. Cl.
USPC ......... 514/772.1; 424/400; 514/772; 514/773

(58) Field of Classification Search
USPC ..................... 424/400; 514/772.1, 772, 773
See application file for complete search history.

(56) References Cited

U.S. PATENT DOCUMENTS

| | | | |
|---|---|---|---|
| 4,920,016 | A | 4/1990 | Allen et al. |
| 5,013,556 | A | 5/1991 | Woodle et al. |
| 5,510,103 | A | 4/1996 | Yokoyama et al. |
| 5,605,703 | A | 2/1997 | Lambiez et al. |
| 5,795,589 | A | 8/1998 | Mayer et al. |
| 6,060,518 | A | 5/2000 | Kabanov et al. |
| 6,110,491 | A | 8/2000 | Kirpotin |
| 6,322,805 | B1 | 11/2001 | Kim et al. |
| 6,338,859 | B1 | 1/2002 | Leroux et al. |
| 6,709,679 | B2 | 3/2004 | Kratz |
| 7,097,856 | B2 | 8/2006 | Frechet et al. |
| 7,163,698 | B2 | 1/2007 | Oh et al. |
| 7,332,527 | B2 | 2/2008 | Bronich et al. |
| 7,601,796 | B2 | 10/2009 | Breitenkamp et al. |
| 7,638,558 | B2 | 12/2009 | Breitenkamp et al. |
| 7,659,314 | B2 | 2/2010 | Bae et al. |
| 2003/0143184 | A1 | 7/2003 | Seo et al. |
| 2006/0142506 | A1 | 6/2006 | Breitenkamp et al. |
| 2007/0218120 | A1 | 9/2007 | Lee et al. |
| 2007/0253899 | A1 | 11/2007 | Ai et al. |
| 2008/0035243 | A1 | 2/2008 | Breitenkamp et al. |
| 2008/0248097 | A1 | 10/2008 | Kwon et al. |
| 2008/0274173 | A1 | 11/2008 | Sill et al. |
| 2008/0318879 | A1 | 12/2008 | Etrych et al. |
| 2009/0105351 | A1 | 4/2009 | Jackson et al. |
| 2009/0110662 | A1 | 4/2009 | Breitenkamp et al. |
| 2009/0274753 | A1 | 11/2009 | Bae et al. |
| 2010/0009926 | A1 | 1/2010 | Kim et al. |
| 2010/0035799 | A1 | 2/2010 | Fernandez et al. |
| 2010/0069295 | A1 | 3/2010 | Lavasanifar et al. |
| 2011/0142950 | A1* | 6/2011 | Sill et al. ............... 424/497 |

FOREIGN PATENT DOCUMENTS

| | | |
|---|---|---|
| WO | 9710849 | 3/1997 |
| WO | 9712895 | 4/1997 |
| WO | 9807434 | 2/1998 |
| WO | 9959548 | 11/1999 |
| WO | 0200194 | 1/2002 |
| WO | 02/26867 | 4/2002 |
| WO | 03033592 | 4/2003 |
| WO | 2005/120585 | 12/2005 |
| WO | 2006047419 | 5/2006 |
| WO | 2006074202 | 7/2006 |
| WO | 2006098547 | 9/2006 |
| WO | 2007110003 | 10/2007 |
| WO | 2007127440 | 11/2007 |
| WO | 2007127473 | 11/2007 |
| WO | 2008071009 | 6/2008 |
| WO | 2008134731 | 6/2008 |
| WO | 2008134761 | 11/2008 |
| WO | 2009091103 | 7/2009 |
| WO | 2010013836 | 4/2010 |

OTHER PUBLICATIONS

O'Reilly et al., Chem. Mater., 2005, 17, 5976-5988.*
International Search Report for PCT/US2010/033205, mailed Jul. 2, 2010.
Written Opinion for PCT/US2010/033205, mailed Jul. 2, 2010.
Oh, Kyung et al. "L-Histidine-based pH-sensitive anticancer drug carrier micelle: Reconstitution and brief evaluation of its systematic toxicity". Department of Pharmaceutics and Pharmaceutical Chemistry, University of Utah. Mar. 13, 2008.
Yueying, He et al. "Mlcellar carrier based on methoxy poly(ethylene glycol)-block-poly-(e-caprolactone) block copolymers bearing ketone groups on the polyester block for doxorubicin delivery". Science+Business Media, Oct. 15, 2009.
El-Sayed, Mohamed et al. "Rational design of composition and activity correlations for pH-responsive and glutathione-reactive polymer therapeutics". Journal of Controlled Science, Mar. 19, 2005.
Yang, Xiaoqiang, et al. "Tumor-Targeting, pH-Responsive, and Stable Unimolecular Micelles as Drug Nanocarriers for Targeted Cancer Therapy". Department of Mechanical Engineering, Department of Biological Sciences, and Department of Materials, University of Wisconsin-Milwaukee. Jan. 31, 2010.
Theodoulou et al. "Cardiac profiles of liposomal anthracyclines: greater cardiac safety versus conventional doxorubicin?" Cancer. May 15, 2004;100(10):2052-63.

(Continued)

*Primary Examiner* — Abigail Fisher

(74) *Attorney, Agent, or Firm* — Choate, Hall & Stewart LLP; Andrea L. C. Robidoux; Danielle M. Nihan

(57) ABSTRACT

The present invention provides micelles having an anthracycline encapsulated therein, the micelles comprising a multiblock copolymer. The invention further provides methods of preparing and using said micelles, and compositions thereof.

11 Claims, 23 Drawing Sheets

(56) References Cited

OTHER PUBLICATIONS

Gabizon et al. "In vivo fate of folate-targeted polyethylene-glycol liposomes in tumor-bearing mice." Clin Cancer Res. Dec. 15, 2003;9(17):6551-9.
Yamada et al. "Design of folate-linked liposomal doxorubicin to its antitumor effect in mice." Clin Cancer Res. Dec. 15, 2008;14(24):8161-8.
Wong et al. "A new polymer-lipid hybrid nanoparticle system increases cytotoxicity of doxorubicin against multidrug-resistant human breast cancer cells." Pharm Res. Jul. 2006;23(7):1574-85.
Lee et al. "A single dose of doxorubicin-functionalized bow-tie dendrimer cures mice bearing C-26 colon carcinomas." Proc Natl Acad Sci U S A. Nov. 7, 2006;103(45):16649-54.
Ryppa et al. "In vitro and in vivo evaluation of doxorubicin conjugates with the divalent peptide E-[c(RGDfK)2] that targets integrin alphavbeta3." Bioconjug Chem. Jul. 2008;19(7):1414-22.
Meyer-Losic et al. "Improved therapeutic efficacy of doxorubicin through conjugation with a novel peptide drug delivery technology (Vectocell)." J Med Chem. Nov. 16, 2006;49(23):6908-16.
Bibby et al. "Pharmacokinetics and biodistribution of RGD-targeted doxorubicin-loaded nanoparticles in tumor-bearing mice." Int J Pharm. Apr. 11, 2005;293(1-2):281-90.
Nasongkla et al. "cRGD-functionalized polymer micelles for targeted doxorubicin delivery." Angew Chem Int Ed Engl. Nov. 26, 2004;43(46):6323-7.
Shuai et al. "Micellar carriers based on block copolymers of poly(epsilon-caprolactone) and poly(ethylene glycol) for doxorubicin delivery." J Control Release. Aug. 27, 2004;98(3):415-26.
Gao et al. "Doxorubicin loaded pH-sensitive micelle targeting acidic extracellular pH of human ovarian A2780 tumor in mice." J Drug Target. Aug. 2005;13(7):391-7.
Lee et al. "Doxorubicin loaded pH-sensitive polymeric micelles for reversal of resistant MCF-7 tumor." J Control Release. Mar. 21, 2005;103(2):405-18.
Gillies E. et al. "pH-Responsive copolymer assemblies for controlled release of doxorubicin." Bioconjug Chem. Mar.-Apr. 2005;16(2):361-8.
Kataoka K et al. "Doxorubicin-loaded poly(ethylene glycol)-poly(beta-benzyl-L-aspartate) copolymer micelles: their pharmaceutical characteristics and biological significance." J Control Release. Feb. 14, 2000;64(1-3):143-53.
Liu et al. "Bio-functional micelles self-assembled from a folate-conjugated block copolymer for targeted intracellular delivery of anticancer drugs." Biomaterials. Mar. 2007;28(7):1423-33.
Yoo et al. "Folate-receptor-targeted delivery of doxorubicin nano-aggregates stabilized by doxorubicin-PEG-folate conjugate." J Control Release. Nov. 24, 2004;100(2):247-56.
Bae et al. "Design of environment-sensitive supramolecular assemblies for intracellular drug delivery: polymeric micelles that are responsive to intracellular pH change." Angew Chem Int Ed Engl. Oct. 6, 2003;42(38):4640-3.
Sakai et al. The structure of copolymers of L-proline with gamma-benyl-L-glutamate in organic solvents. Bull Chem. Soc. Japan 1969, 42, 1332-1336.
Paolillo et al. "Nuclear magnetic resonance and optical spectroscopic studies of copolymers of polypeptides_II Random copoly(benzyl-L-glutamate_benzyl -L-aspartate) and (benzyl-n-glutamate_ benzyl-L-aspartate)" Biopolymers 1972, 11, 2043-2052.
Cho et al. "Synthesis and characterization of di- and triblock copolymers of poly(ethylene oxide) and poly(DL-valine-co-DL-leucine)" Polymer 2003, 44, 5497-5500.
Chatterjee et al. "pH-reversible magnetic gel with a biodegradable polymer" J. App. Polym. Sci. 2004, 91, 3337-3341.
Du et al. "pH-Responsive Vesicles Based on a Hydrolytically Self-Cross-Linkable Copolymer" J. Am. Chem. Soc. 2005, 127, 12800-12801.
Twaites et al. Thermo and pH responsive polymers as gene delivery vectors: effect of polymer architecture on DNA complexation in vitro' J. Control. Release 2004, 97, 551-566.

Murthy et al. "Design and synthesis of pH-responsive polymeric carriers that target uptake and enhance the intracellular delivery of oligonucleotides" J.Control. Release 2003, 89, 365-374.
El-Sayed et al. "Rational design of composition and activity correlations for pH-responsive and glutathione-reactive polymer therapeutics" J. Control. Release 2005, 104, 417-427.
Liu et al. "New poly(d-glucaramidoamine)s induce DNA nanoparticle formation and efficient gene delivery into mammalian cells" J Am Chem Soc. Jun. 23, 2004;126(24):7422-3.
Schiffelers et al. "Anti-tumor efficacy of tumor vasculature-targeted liposomal doxorubicin". Journal of Controlled Release 91 (2003) 115-122.
Veronese et al. "PEG-Doxorubicin Conjugates: Influence of Polymer Structure on Drug Release, in Vitro Cytotoxicity, Biodistribution, and Antitumor Activity" Bioconjugate Chem. 2005, 16, 775-784.
Ko et al. "Tumoral acidic extracellular pH targeting of pH-responsive MPEG-poly (β-amino ester) block copolymer micelles for cancer therapy". Journal of Controlled Release 123 (2007) 109-115.
Matsumura et al. "Phase I clinical trial and pharmacokinetic evaluation of NK911, a micelle-encapsulated doxorubicin". British Journal of Cancer (2004) 91, 1775-1781.
Kim et al. "Polymeric Micelles with Ionic Cores Containing Biodegradable Cross-Links for Delivery of Chemotherapeutic Agents" Biomacromolecules 2010, 11, 919-926.
Yin et al. "Physicochemical aspects of doxorubicin-loaded pH-sensitive polymeric micelle formulations from a mixture of poly(L-histidine)-b-poly(L-lactide)-b-poly(ethylene glycol)". European Journal of Pharmaceutics and Biopharmaceutics 71 (2009) 223-230.
Hruby et al. "Polymeric micellar pH-sensitive drug delivery system for doxorubicin" Journal of Controlled Release 103 (2005) 137-148.
Xiong et al. "Multifunctional Polymeric Micelles for Enhanced Intracellular Delivery of Doxorubicin to Metastatic Cancer Cells" Pharm Res. Nov. 2008;25(11):2555-66.
Kim et al. "Doxorubicin-Loaded Polymeric Micelle Overcomes Multidrug Resistance of Cancer by Double-Targeting Folate Receptor and Early Endosomal pH" Small. Nov. 2008;4(11):2043-50.
Minko et al. "Pluronic block copolymers alter apoptotic signal transduction of doxorubicin in drug-resistant cancer cells" Journal of Controlled Release 105 (2005) 269-278.
Allen et al. "Pharmacokinetics and Pharmacodynamics of Lipidic Nano-Particles in Cancer" Anti-Cancer Agents in Medicinal Chemistry, 2006, 6, 513-523.
Rolland et al. "Direct Fabrication and Harvesting of Monodisperse, Shape-Specific Nanobiomaterials" J. Am. Chem. Soc. 2005, 127, 10096-10100.
Wu et al. "Tumor-Targeting Peptide Conjugated pH-Responsive Micelles as a Potential Drug Carrier for Cancer Therapy" Bioconjugate Chem. 2010, 21, 208-213.
Rihova et al. Biological evaluation of polymeric micelles with covalently bound doxorubicin, Bioconjugate Chem. 2009, 20, 2090-2097.
Zhu et al. "Novel micelles from graft polyphosphazenes as potential anti-cancer drug delivery systems: Drug encapsulation and in vitro evaluation". International Journal of Pharmaceutics 373 (2009) 133-140.
Yokoyama et al. "Characterization of physical entrapment and chemical conjugation of adriamycin in polymeric micelles and their design for in vivo delivery to a solid tumor" Journal of Controlled Release 50 (1998) 79-92.
Lee et al. "Synthesis, Characterization, Antitumor Activity of Pluronic Mimicking Copolymer Micelles Conjugated with Doxorubicin via Acid-Cleavable Linkage". Bioconjugate Chem. 2008, 19, 525-531.
Bae et al. "In Vivo Antitumor Activity of the Folate-Conjugated pH-Sensitive Polymeric Micelle Selectively Releasing Adriamycin in the Intracellular Acidic Compartments". Bioconjug Chem. Jul.-Aug. 2007;18(4):1131-9.
Kwon et al. "Block copolymer micelles for drug delivery: loading and release of doxorubicin". Journal of Controlled Release 48 (1997) 195-201.
Williams et al. "The chemical speciation of zinc in human saliva: possible correlation with reduction of the symptoms of the common cold produced by zinc gluconate-containing lozenges", Chemical Speciation and Bioavailability, vol. 11, No. 3, (1999), 95-101(7).

Lee et al. ""Clickable" polymer-caged nanobins as a modular drug delivery platform." J Am Chem Soc. Jul. 8, 2009;131 (26):9311-20.

Laginha et al. "Bioavailability and therapeutic efficacy of HER2 scFv-targeted liposomal doxorubicin in a murine model of HER2-overexpressing breast cancer." J Drug Target. Aug. 2008;16(7):605-10.

Tezcan et al. Metal-Mediated Self-Assembly of Protein Superstructures: Influence of Secondary Interactions on Protein Oligomerization and Aggregation. J Am Chem Soc. May 14, 2008;130(19):6082-4.

Eby, "Zinc ion availability—the determinant of efficacy in zinc lozenge treatment of common colds." J Antimicrob Chemother. Oct. 1997;40(4):483-93.

Opanasopit, P. et al., Block Copolymer Design for Camptothecin Into Polymer Micelles for Passive Tumor Targeting, Pharmaceutical Research, 21:2001-2008 (2004).

Yamamoto, T. et al., What are the determining factors for stable drug encapsulation into polymeric micelle carriers? Consideration on physical and chemical characters of the micelle inner core, Journal of Controlled Release, 123:11-18 (2007).

* cited by examiner

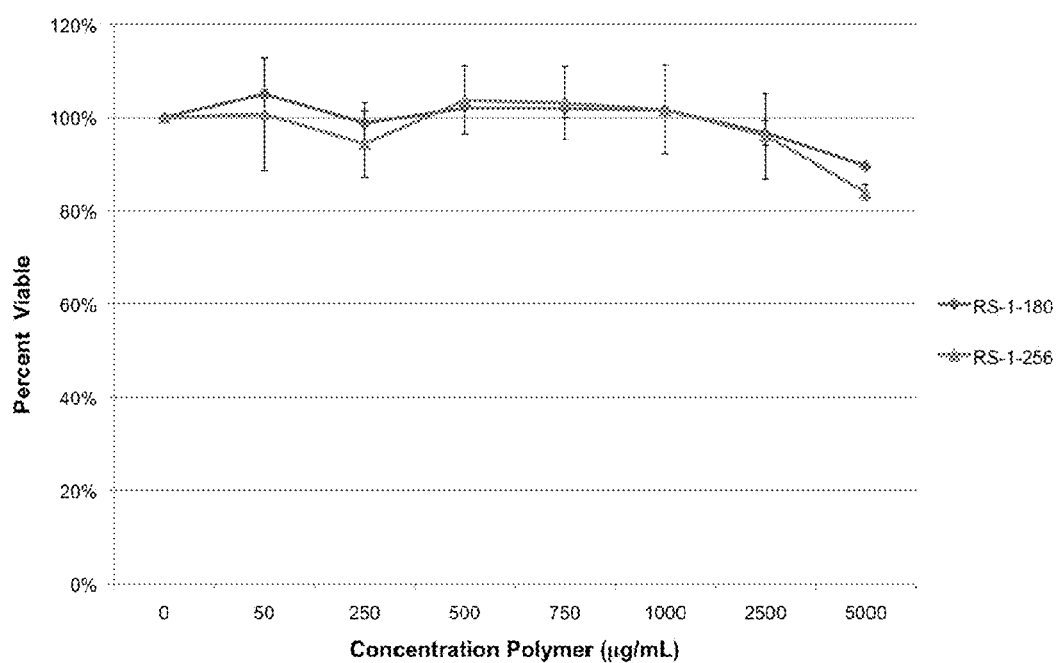
Figure 1. Cytotoxic effects of triblock co-polymers on HUVEC cells.

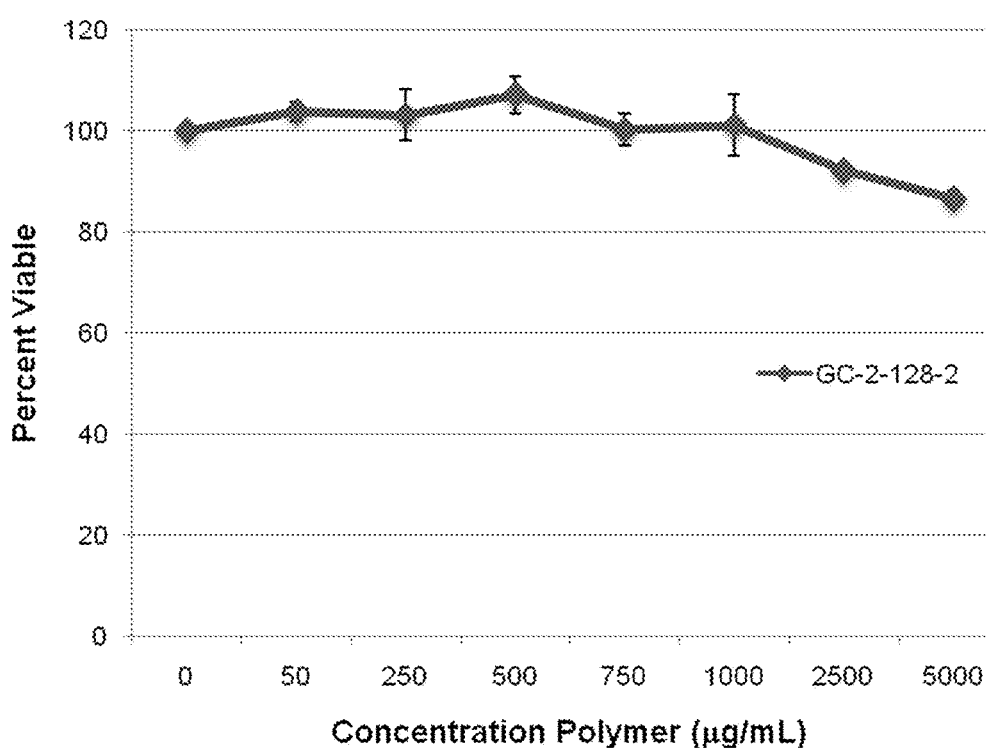
Figure 2. Cytotoxic effects of histylated polymer on HUVEC cells

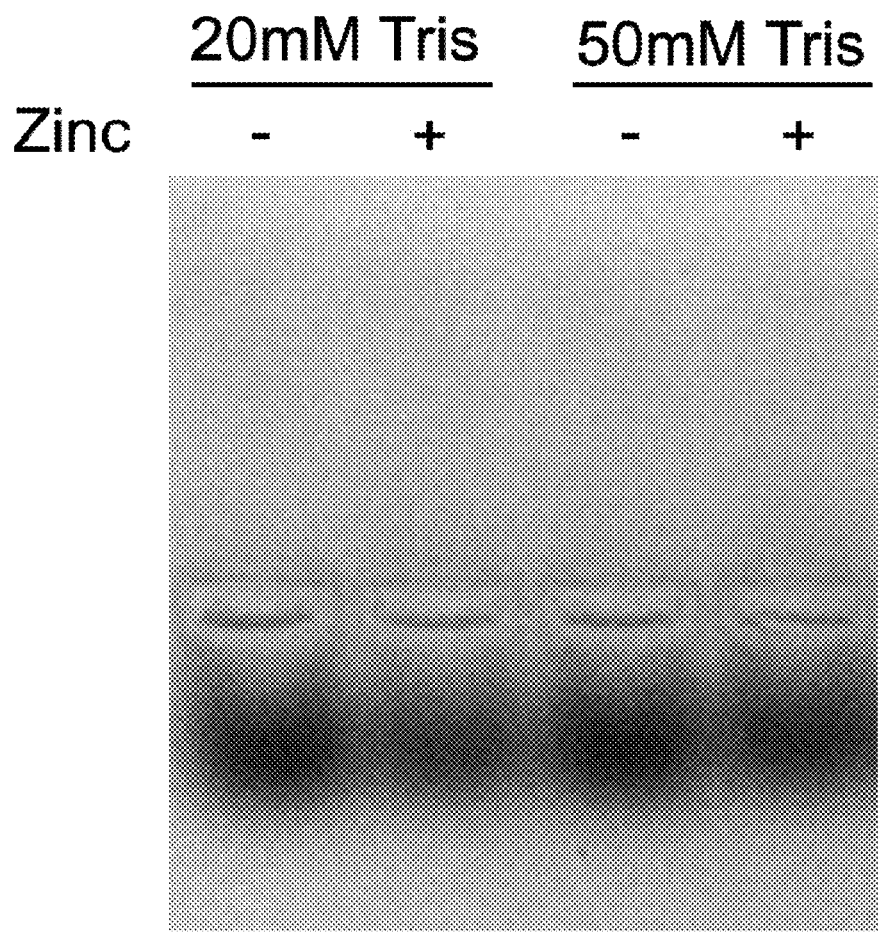
Figure 3. Agarose Gel Electrophoresis of Dox loaded Micelles and crosslinked DOX loaded micelles

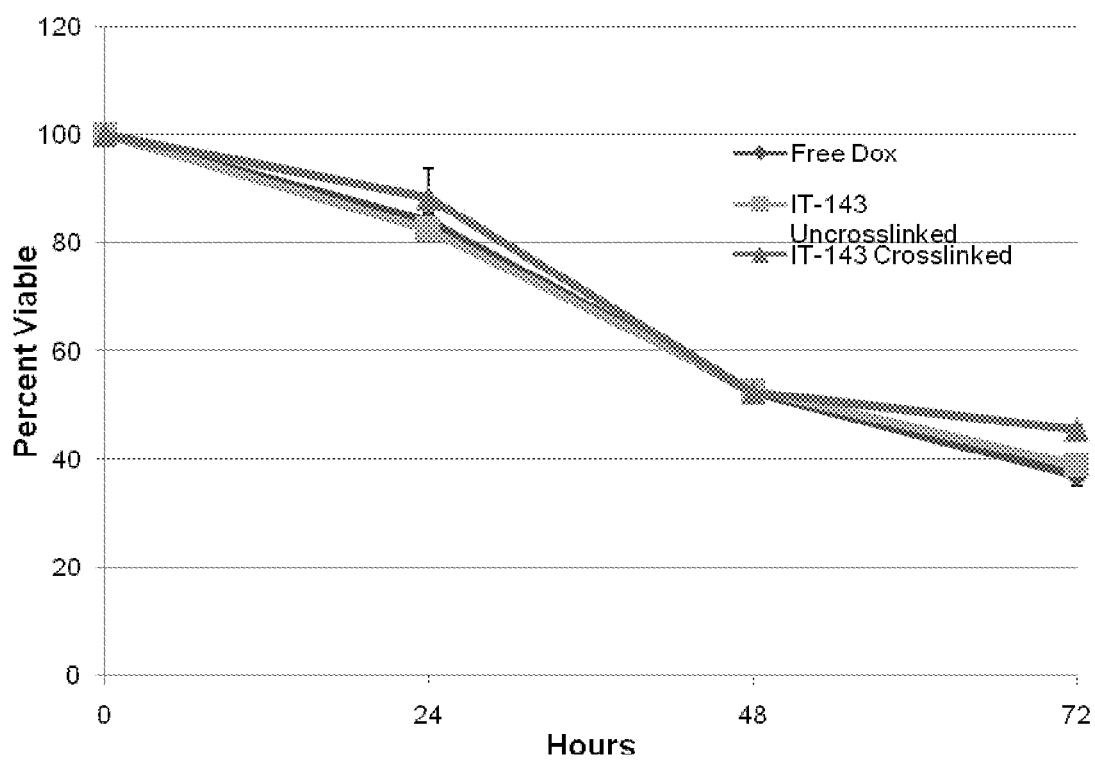
Fig. 4. MCF-7 cells treated with Free doxorubicin, Dox Loaded micelles (IT-143 uncrosslinked) or crosslinked DOX loaded micelles (IT-143 crosslinked)

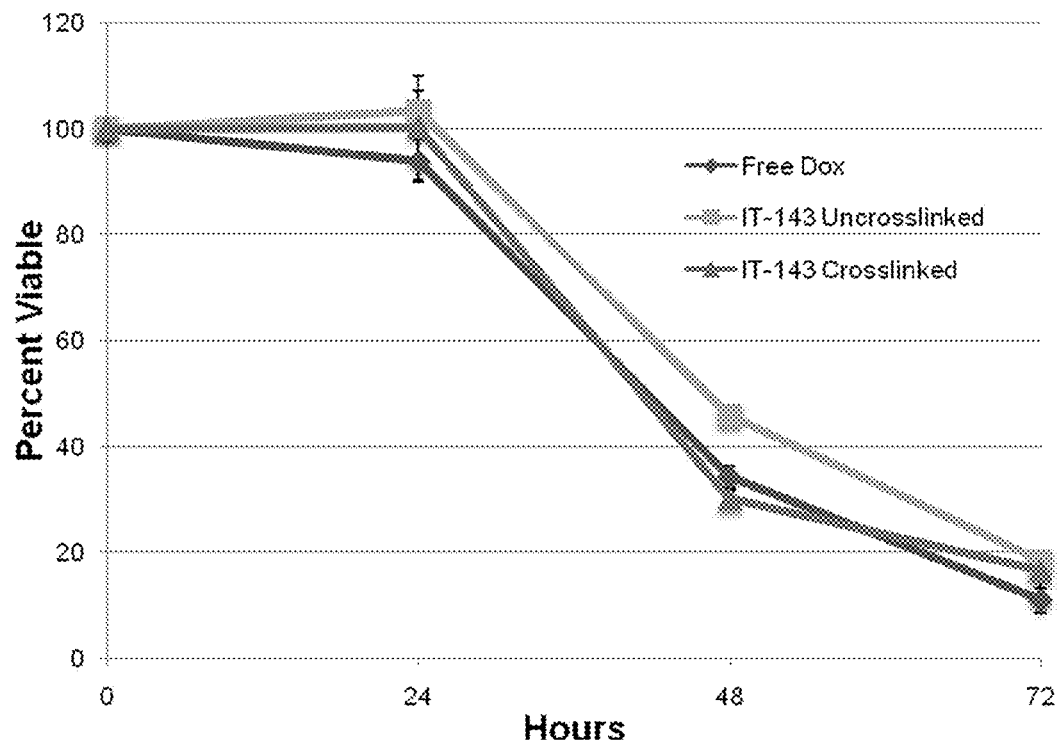
Fig. 5. MDA-MB-453 cells treated with Free doxorubicin, Dox Loaded micelles (IT-143 uncrosslinked) or crosslinked DOX loaded micelles (IT-143 crosslinked)

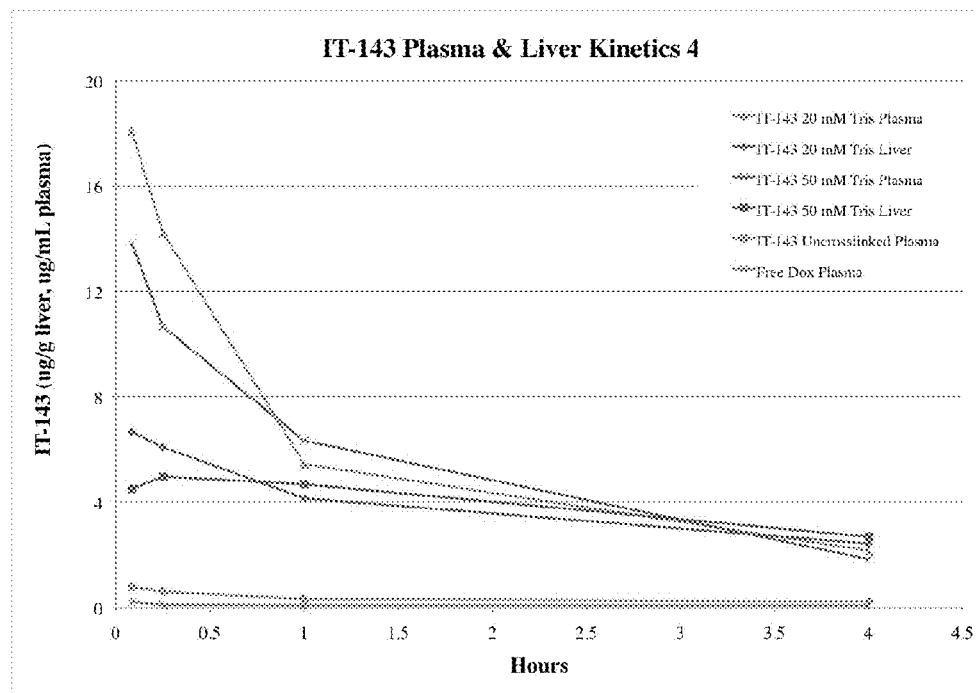
Figure 6. Pharmacokinetic data for free doxorubicin, uncrosslinked dox loaded micelles, and crosslinked dox loaded micelles

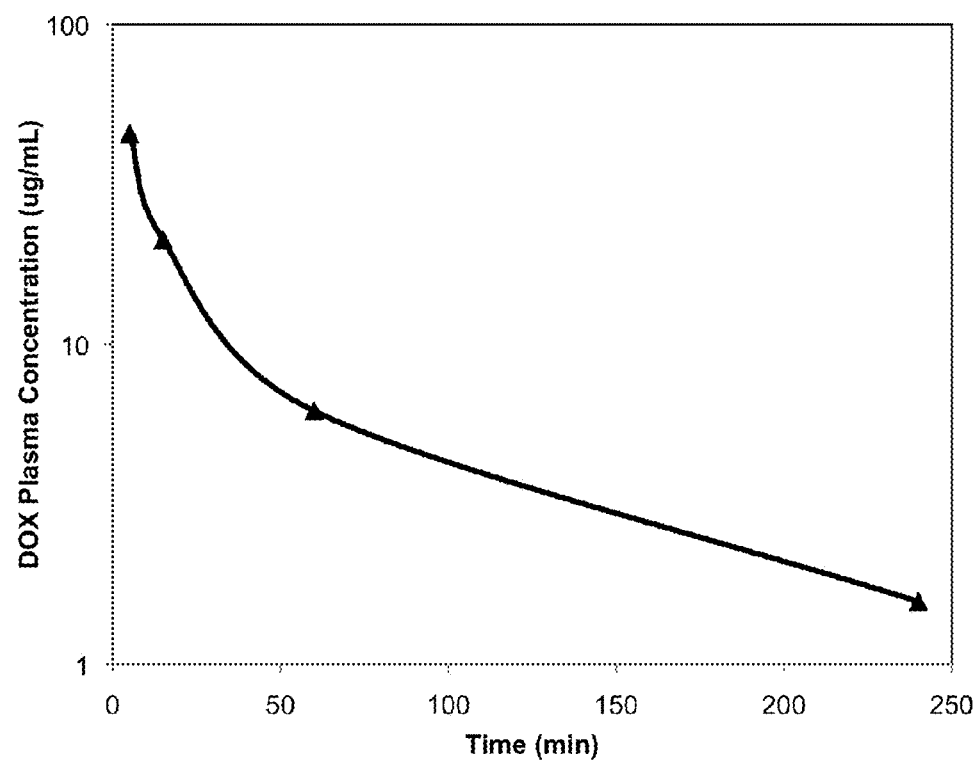
Figure 7. Pharmacokinetic data for crosslinked Dox loaded micelles from Example 30

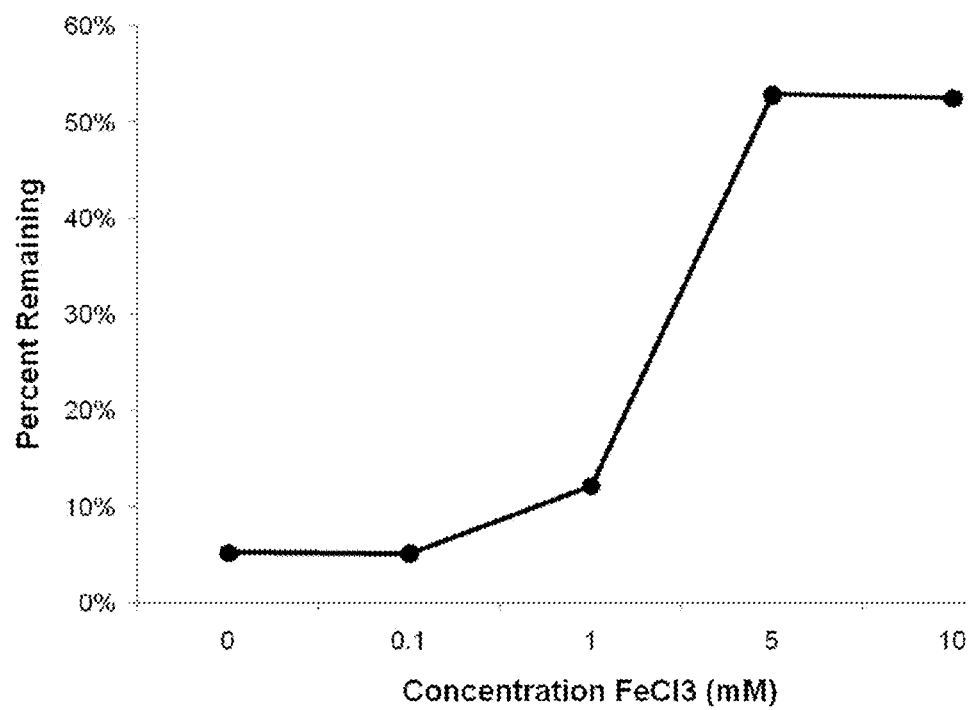
Figure 8. Stability of Iron (III) Crosslinked Dox micelles.

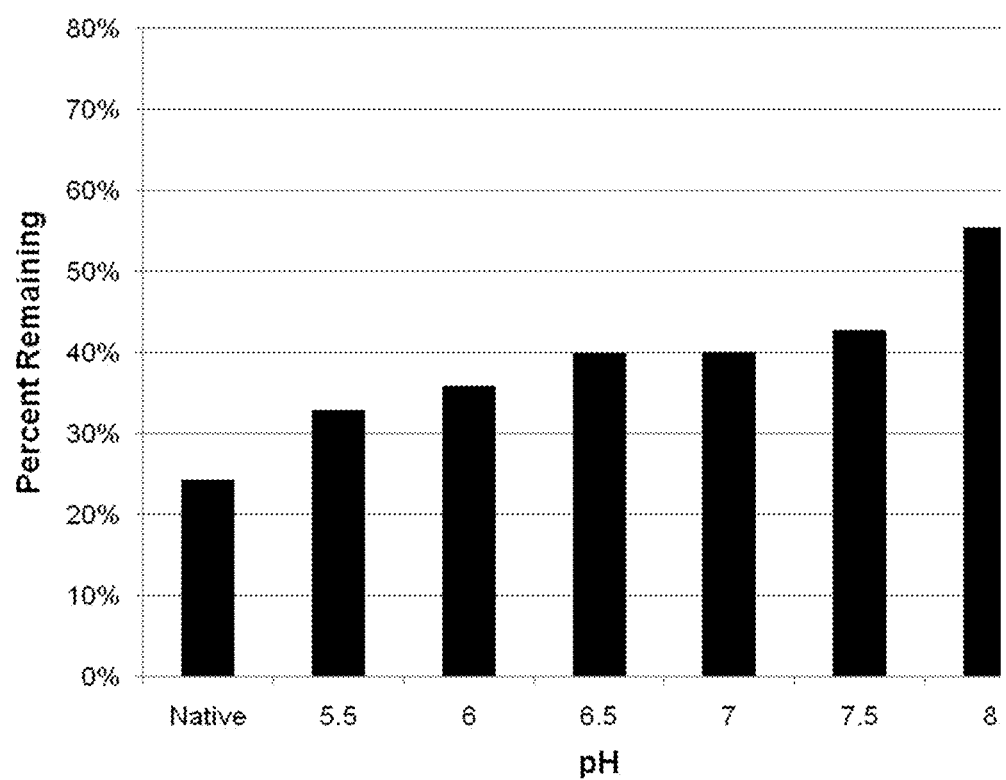
Figure 9. Crosslinking optimization with iron (III) chloride.

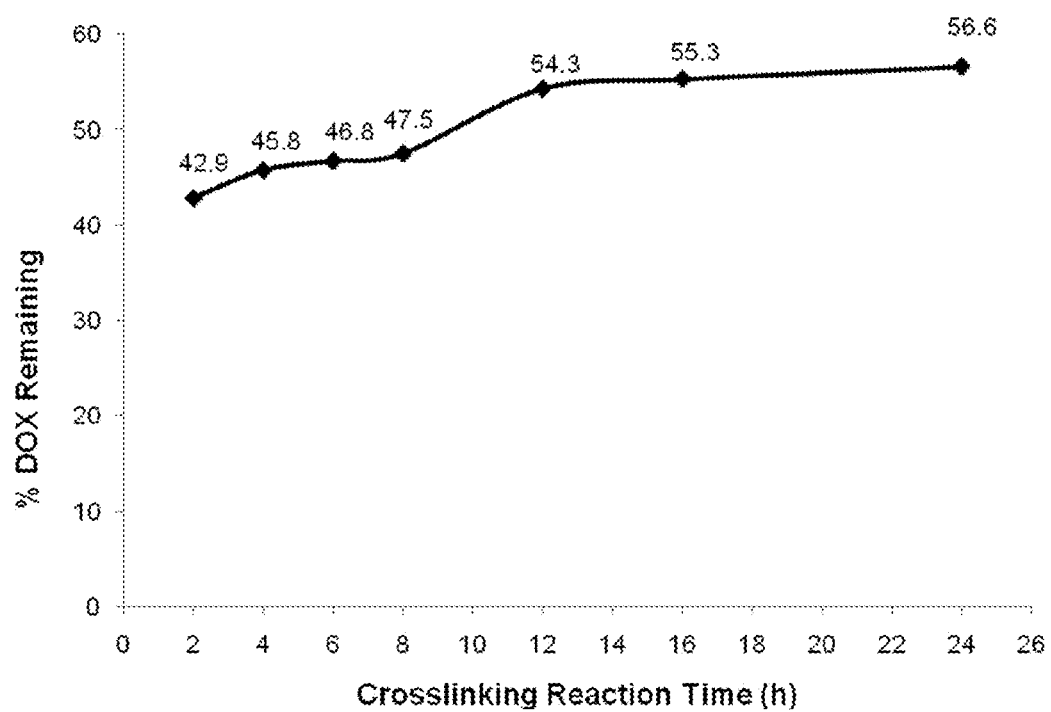
Figure 10. Crosslinking kinetics with iron (III) chloride

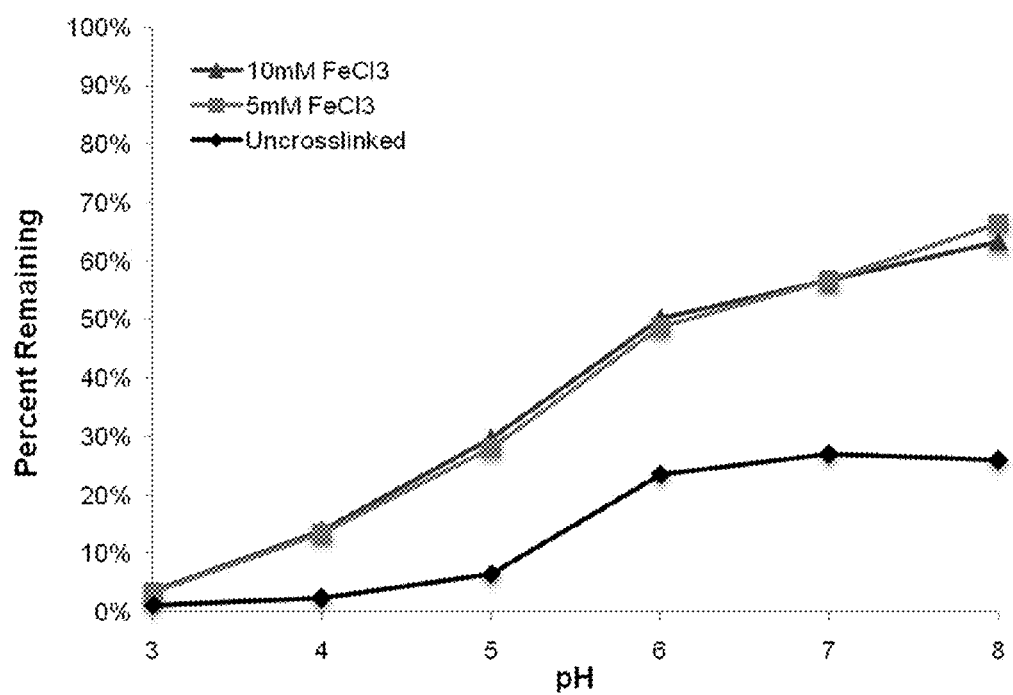
Figure 11. pH-Dependent release of iron (III)crosslinked micelles vs. uncrosslinked micelles.

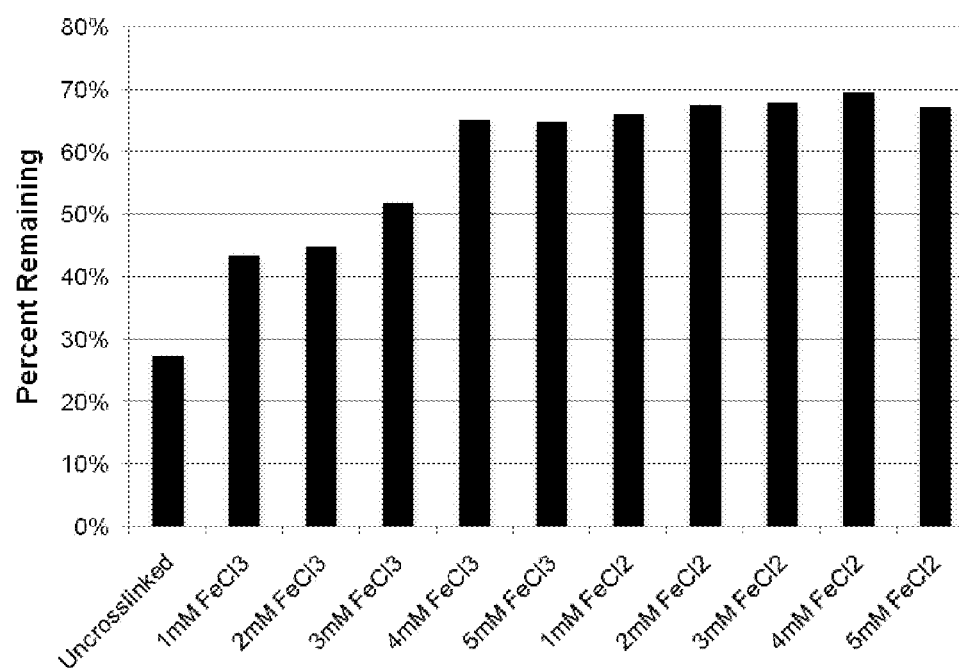
Figure 12. Comparison of crosslinking using iron (II) vs. iron (III)

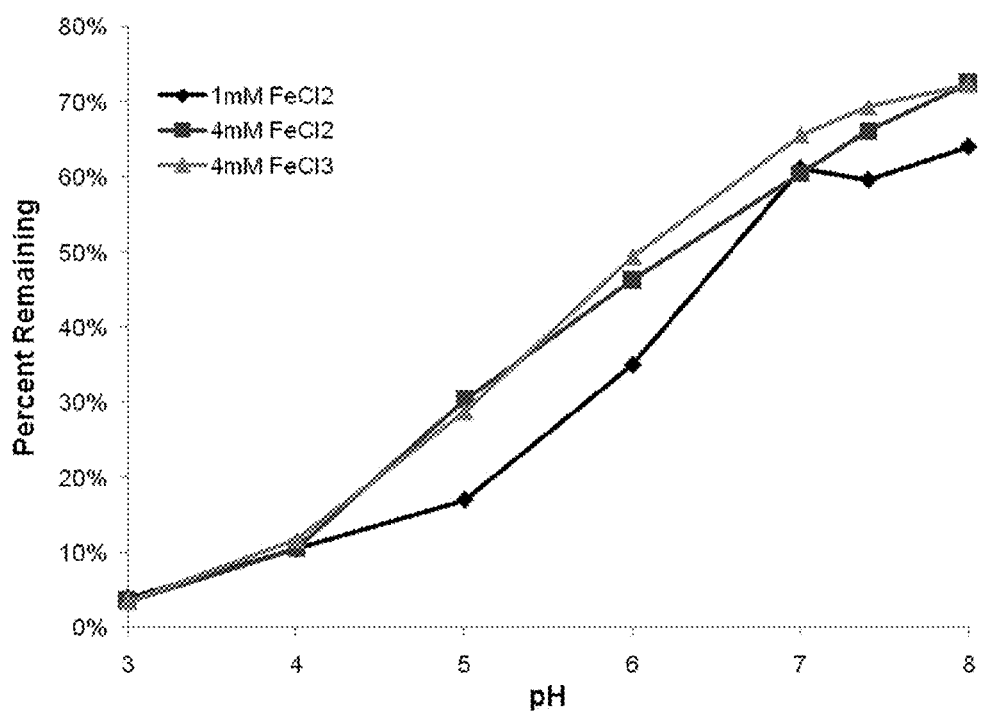
Figure 13. pH Dependent Release of iron (II) vs. iron (III) crosslinked micelles.

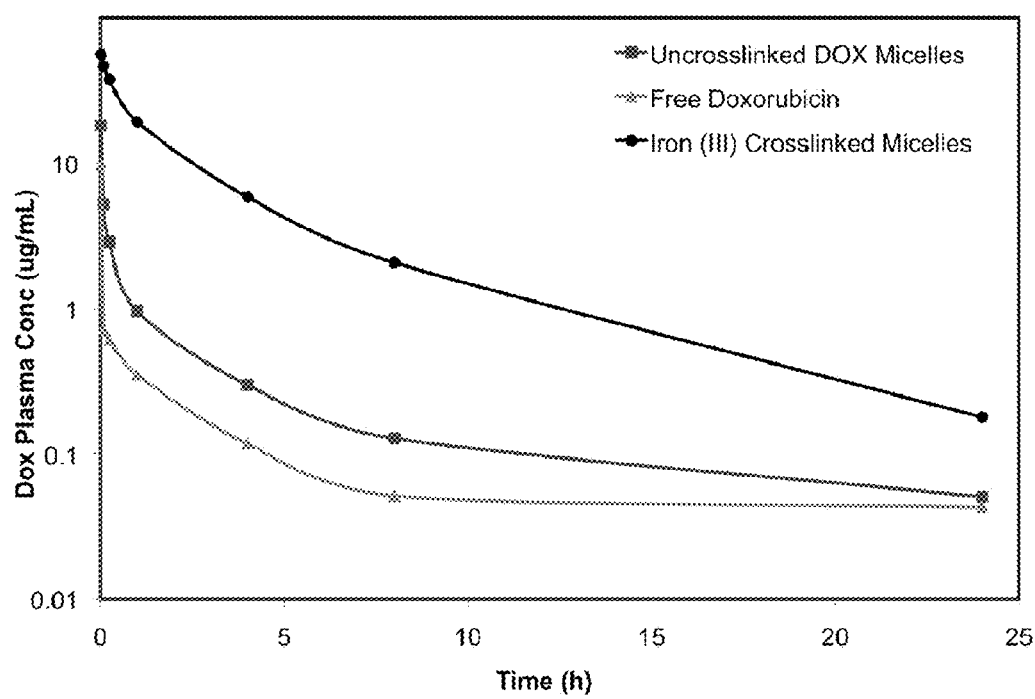
Figure 14. Rat PK of Free DOX compared to uncrosslinked and iron (III) crosslinked micelles.

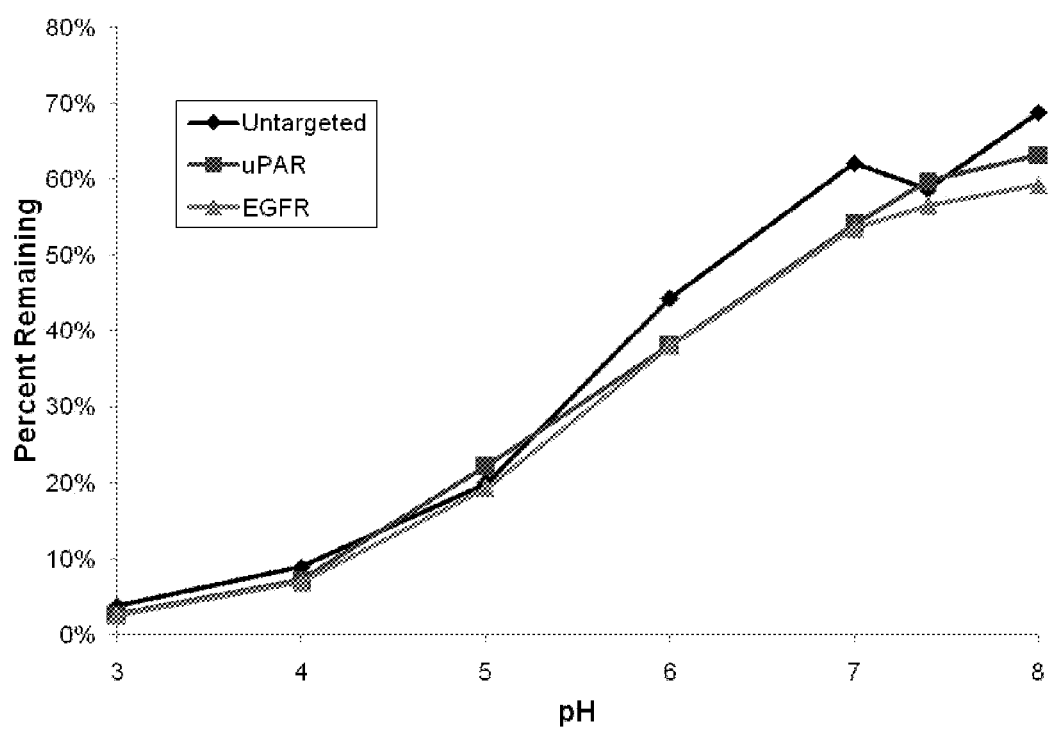
Figure 15. pH Dependent release of crosslinked Dox micelles.

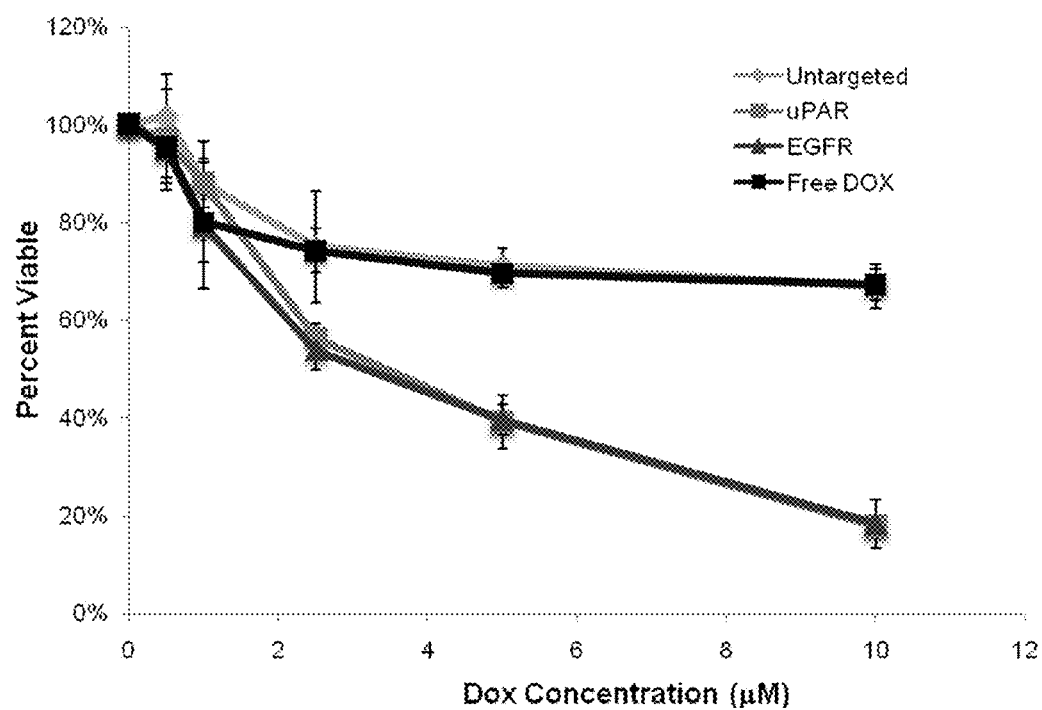
Figure 16. Pulse-treatment cytotoxicity assay for free drug and targeted and untargeted crosslinked Dox micelles in A549 cells.

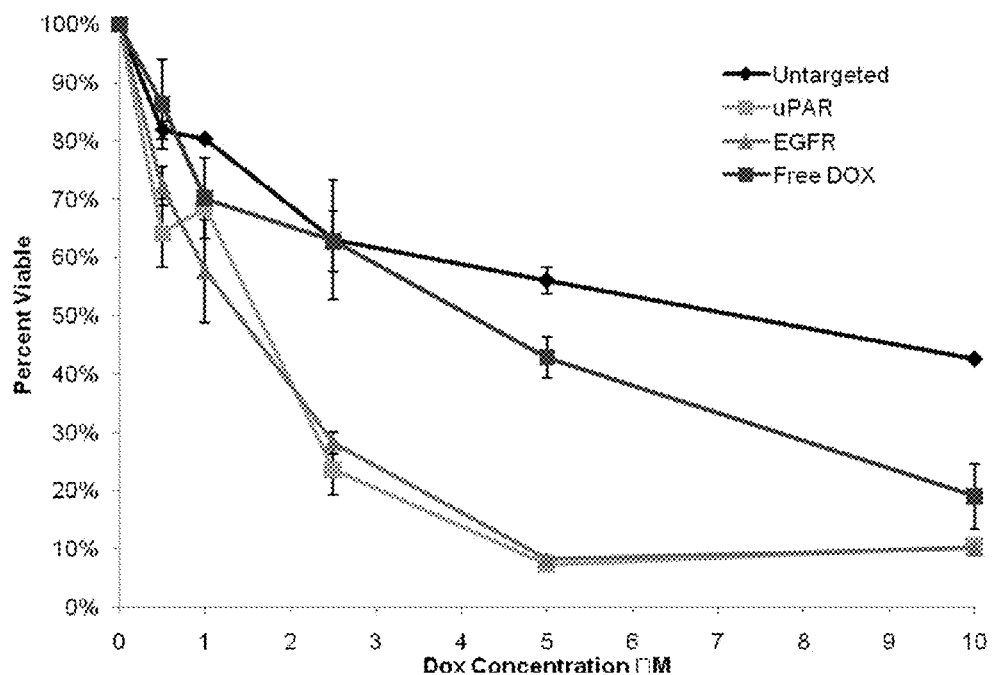
Figure 17. Pulse-treatment cytotoxicity assay for free drug and targeted and untargeted crosslinked Dox micelles in 8505C cells.

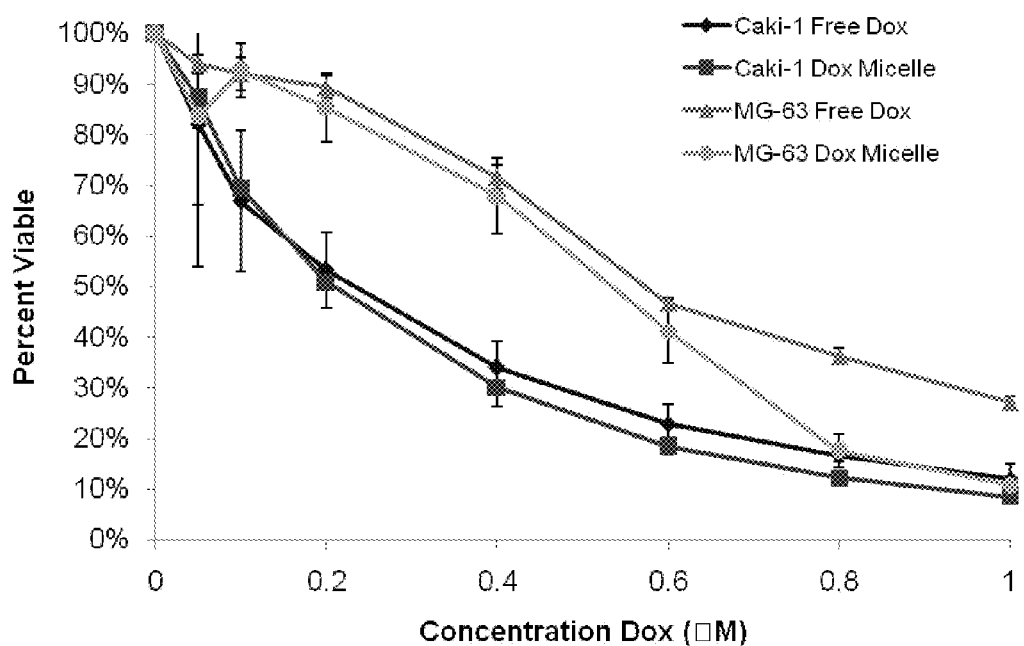
Figure 18. 72-hour cytotoxicity assay for free doxorubicin and crosslinked Dox micelles in Caki-1 and MG-63 cells.

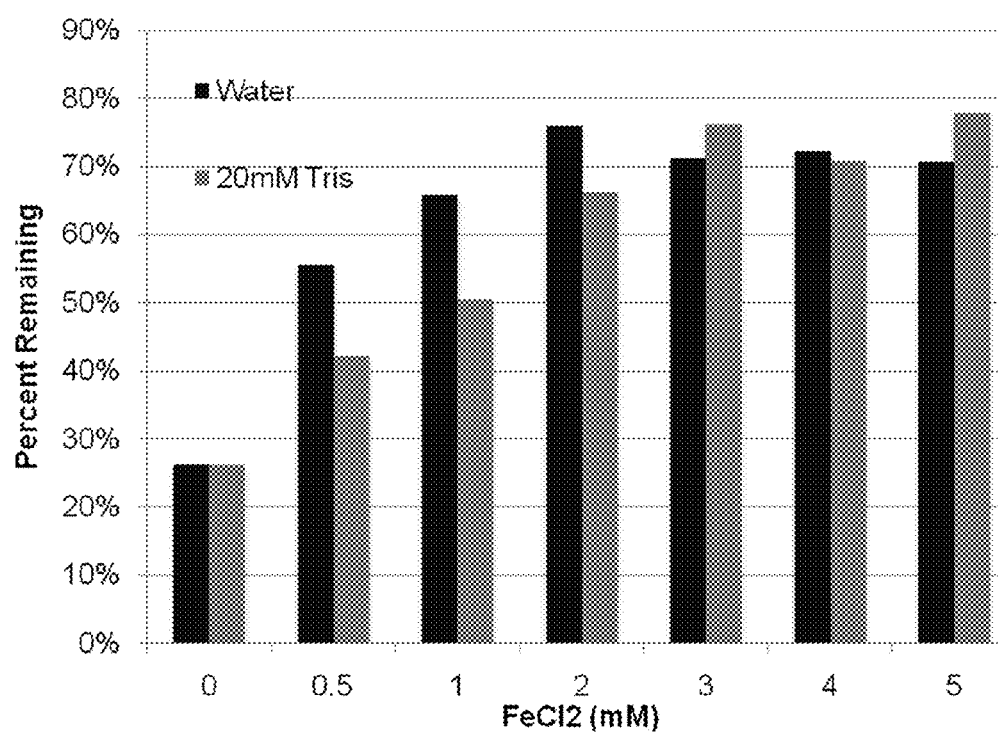
Figure 19. Iron (II)-mediated crosslinking of daunorubucin in water or 20mM Tris buffer.

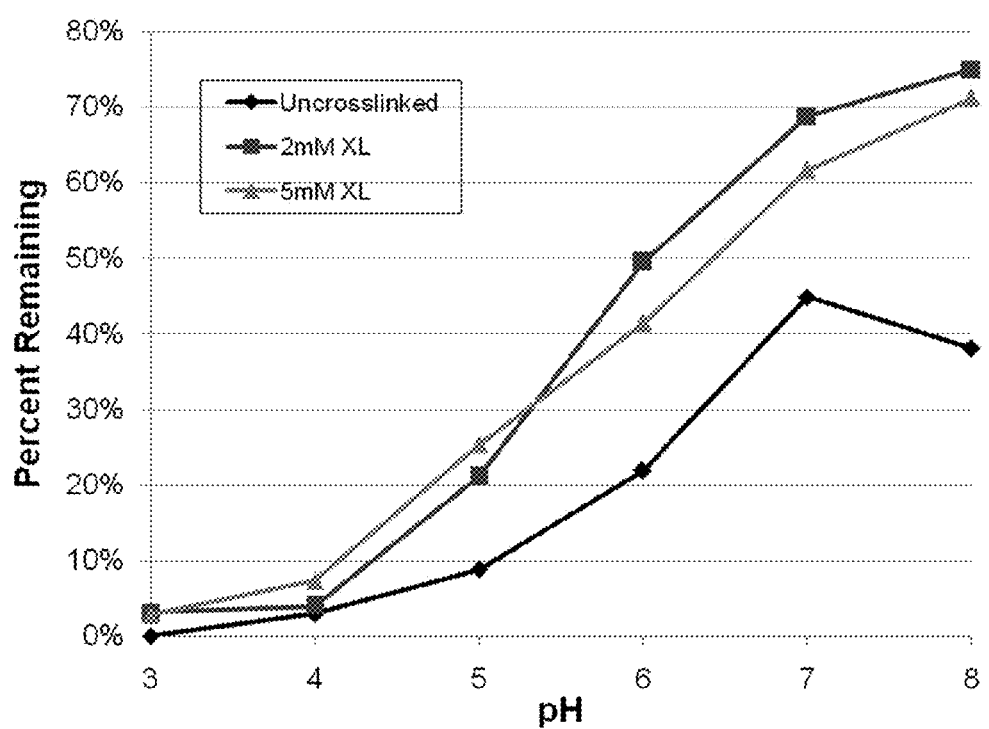
Figure 20. pH-dependent release of 2mM or 5mM iron (II) crosslinked and uncrosslinked daunorubicin micelles.

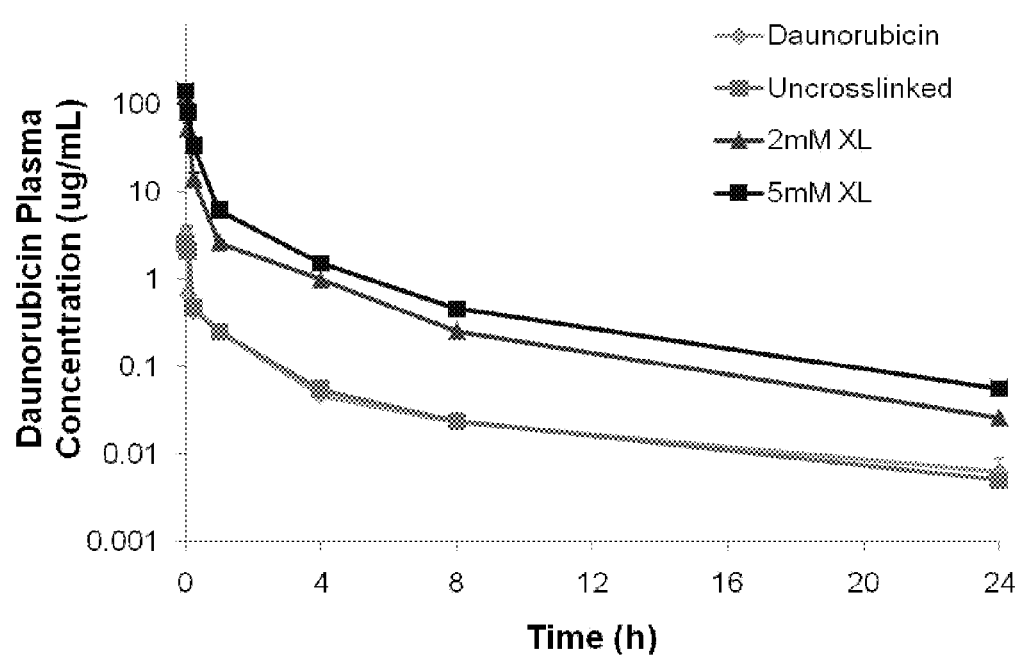
Figure 21. Rat pharmacokinetics of free daunorubicin compared to uncrosslinked and iron (II) crosslinked daunorubicin micelles.

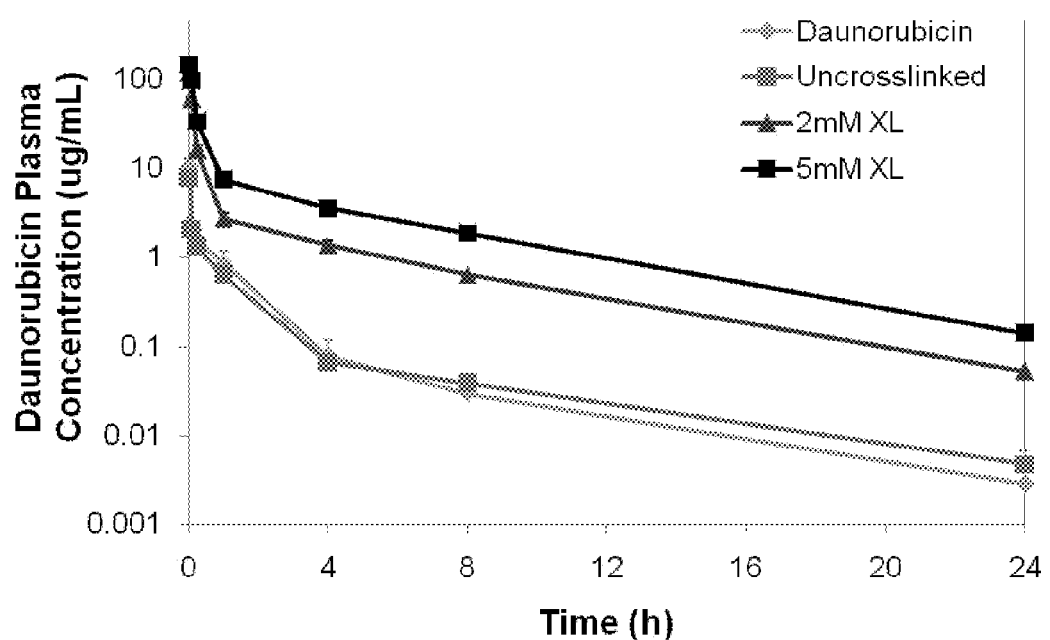
Figure 22. Repeat experiment of Rat pharmacokinetics of free daunorubicin compared to uncrosslinked and iron (II) crosslinked daunorubicin micelles.

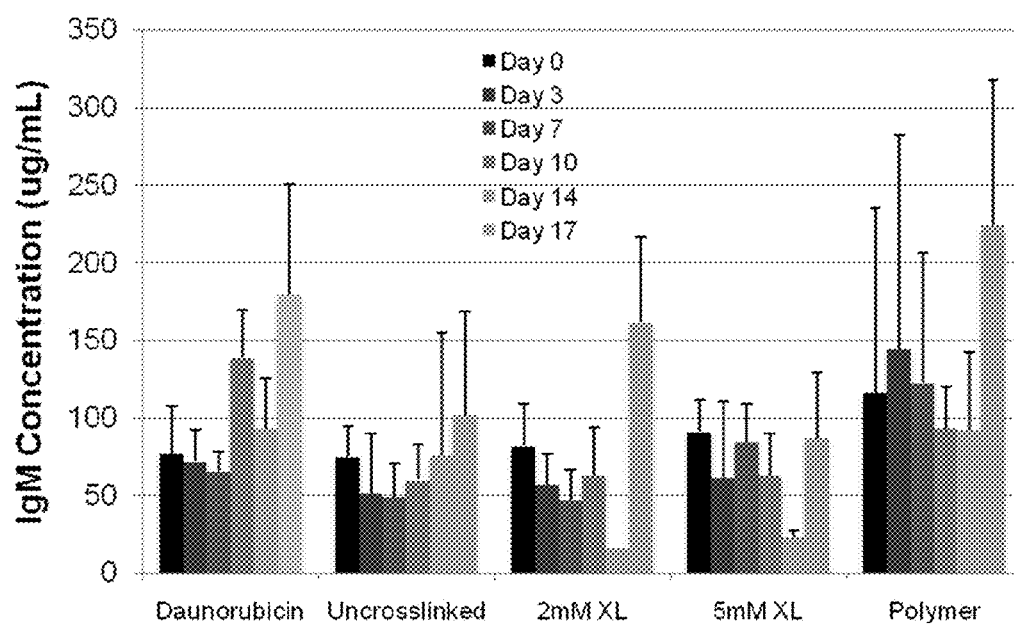
Figure 23. ELISA for rat IgM from Example 55.

POLYMER MICELLES CONTAINING ANTHRACYLINES FOR THE TREATMENT OF CANCER

CROSS-REFERENCE TO RELATED APPLICATIONS

The present application claims priority to U.S. Provisional patent application Ser. No. 61/174,160, filed Apr. 30, 2009, and U.S. Provisional patent application Ser. No. 61/178,630, filed May 15, 2009, the entire contents of both of which are incorporated herein by reference.

FIELD OF THE INVENTION

The present invention relates to the field of polymer chemistry and more particularly to polymer micelles and uses thereof.

BACKGROUND OF THE INVENTION

The development of new therapeutic agents has dramatically improved the quality of life and survival rate of patients suffering from a variety of disorders. However, drug delivery innovations are needed to improve the success rate of these treatments. Specifically, delivery systems are still needed which effectively minimize premature excretion and/or metabolism of therapeutic agents and deliver these agents specifically to diseased cells thereby reducing their toxicity to healthy cells.

Rationally-designed, nanoscopic drug carriers, or "nanovectors," offer a promising approach to achieving these goals due to their inherent ability to overcome many biological barriers. Moreover, their multi-functionality permits the incorporation of cell-targeting groups, diagnostic agents, and a multitude of drugs in a single delivery system. Polymer micelles, formed by the molecular assembly of functional, amphiphilic block copolymers, represent one notable type of multifunctional nanovector.

Polymer micelles are particularly attractive due to their ability to deliver hydrophobic therapeutic agents. In addition, the nanoscopic size of polymeric micelles allows for passive accumulation in diseased tissues, such as solid tumors, by the enhanced permeation and retention (EPR) effect. Using appropriate surface functionality, polymer micelles are further decorated with cell-targeting groups and permeation enhancers that can actively target diseased cells and aid in cellular entry, resulting in improved cell-specific delivery.

Drug delivery vehicles are needed, which are stable to post-administration dilution, can avoid biological barriers (e.g. reticuloendothelial system (RES) uptake), and deliver drugs in response to the physiological environment encountered in diseased tissues, such as solid tumors.

BRIEF DESCRIPTION OF THE DRAWINGS

FIG. 1. Cytotoxic effects of triblock co-polymers on HUVEC cells.

FIG. 2. Cytotoxic effects of histylated polymer on HUVEC cells

FIG. 3. Agarose Gel Electrophoresis of Dox loaded Micelles and crosslinked DOX loaded micelles FIG. 4. MCF-7 cells treated with Free doxorubicin, Dox Loaded micelles (IT-143 uncrosslinked) or crosslinked DOX loaded micelles (IT-143 crosslinked)

FIG. 5. MDA-MB-453 cells treated with Free doxorubicin, Dox Loaded micelles (IT-143 uncrosslinked) or crosslinked DOX loaded micelles (IT-143 crosslinked)

FIG. 6. Pharmacokinetic data for free doxorubicin, uncrosslinked dox loaded micelles, and crosslinked dox loaded micelles FIG. 7. Pharmacokinetic data for crosslinked dox loaded micelles from Example 30

FIG. 7. Pharmacokinetic data for crosslinked dox loaded micelles from Example 30

FIG. 8. Stability of iron (III) crosslinked Dox micelles

FIG. 9. Crosslinking optimization with iron (III) chloride

FIG. 10. Crosslinking kinetics with iron (III) chloride

FIG. 11. pH-Dependent release of iron (III) crosslinked micelles vs. uncrosslinked micelles FIG. 12. Comparison of crosslinking using iron (II) vs. iron (III)

FIG. 13. pH Dependent Release of iron (II) vs. iron (III) crosslinked micelles FIG. 14. Rat PK of Free DOX compared to uncrosslinked and iron (III) crosslinked micelles FIG. 15. pH Dependent release of crosslinked Dox micelles FIG. 16. Pulse-treatment cytotoxicity assay for free drug and targeted and untargeted crosslinked Dox micelles in A549 cells FIG. 17. Pulse-treatment cytotoxicity assay for free drug and targeted and untargeted crosslinked Dox micelles in 8505C cells FIG. 18. 72-hour cytotoxicity assay for free doxorubicin and crosslinked Dox micelles in Caki-1 and MG-63 cells FIG. 19 Iron (II)-mediated crosslinking of daunorubicin in water or 20 mM Tris buffer.

FIG. 20. pH-dependent release of 2 mM or 5 mM iron (II) crosslinked and uncrosslinked daunorubicin micelles.

FIG. 21. Rat pharmacokinetics of free daunorubicin compared to uncrosslinked and iron (II) crosslinked daunorubicin micelles.

FIG. 22. Repeat experiment of Rat pharmacokinetics of free daunorubicin compared to uncrosslinked and iron (II) crosslinked daunorubicin micelles.

FIG. 23. ELISA assay for rat IgM from Example 55.

DETAILED DESCRIPTION OF CERTAIN EMBODIMENTS OF THE INVENTION

1. General Description

Anthracyclines represent a class of antibiotics derived from *Streptomyces* bacteria. While effective toward the inhibition of bacteria growth, their potent cytotoxicity towards mammalian cells has hindered the clinical use of these compounds to treat infections. However, anthracyclines have found widespread use as anticancer agents. There are three mechanisms of action by which this class of compounds is thought to act as antiproliferative agents: DNA intercalation, Topoisomerase II inhibition, and free radical production to induce DNA damage. Due to the multiple mechanisms of action, anthracyclines are toxic against a broad spectrum of cell lines, and thus effective against multiple types of cancer.

Several anthracycline derivates have been produced and have found use in the clinic for the treatment of leukemias, Hodgkin's lymphoma, as well as cancers of the bladder, breast, stomach, lung, ovaries, thyroid, and soft tissue sarcoma. Such anthracycline derivatives include daunorubicin (also known as Daunomycin or daunomycin cerubidine), doxorubicin (also known as DOX, hydroxydaunorubicin, or adriamycin), epirubicin (also known as Ellence or Pharmorubicin), idarubicin (also known as 4-demethoxydaunorubicin, Zavedos, or Idamycin), and valrubicin (also known as N-trifluoroacetyladriamycin-14-valerate or Valstar). Anthracyclines are typically prepared as an ammonium salt (e.g. hydrochloride salt) to improve water solubility and allow for ease of administration.

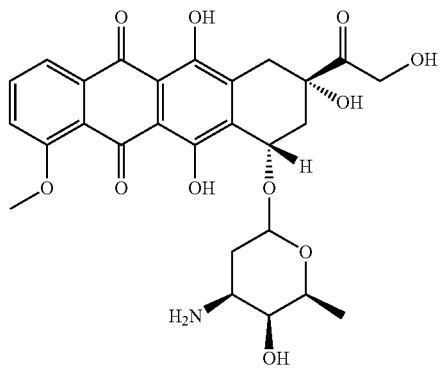

doxorubicin

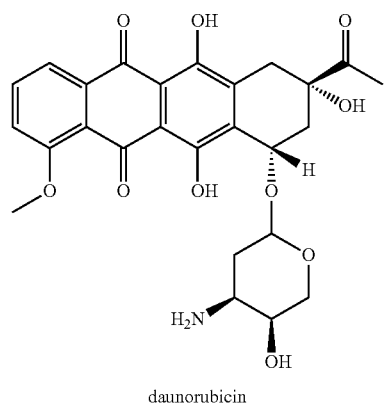

daunorubicin

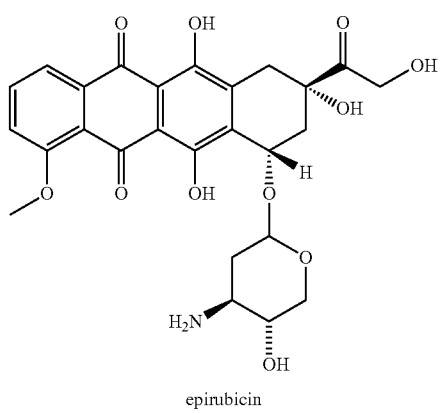

epirubicin

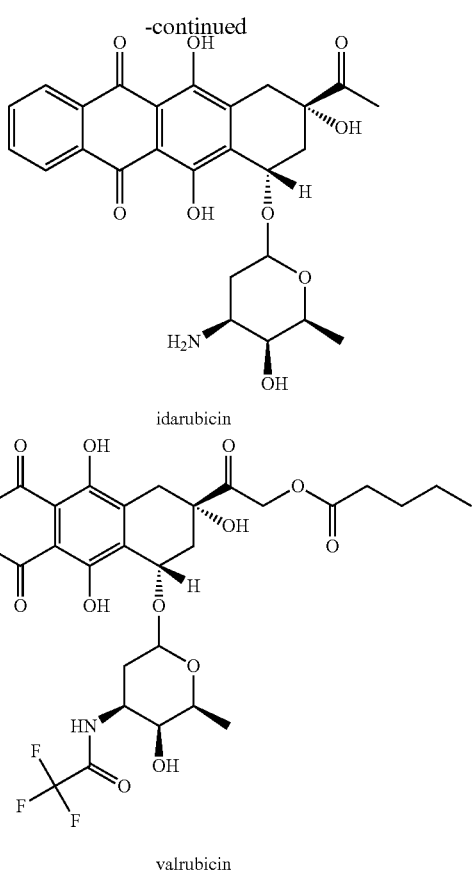

-continued idarubicin valrubicin

While excellent, broad-spectrum antitumor activity has been shown for anthracyclines, a significant side effect is severe cardiotoxicity. An anthracycline formulation with reduced cardiotoxicity would be highly desirable.

A number of approaches have been undertaken to provide an anthracycline formulation with lower toxicity. Liposomal formulations have been developed including doxorubicin loaded into pegylated and nonpegylated liposomes, as well as liposomal daunorubicin (Theodoulou, M., *Cancer.* 2004 15; 100 (10):2052-63). The most successful formulation is Doxil™, a pegylated liposomal formulation that exhibits lower cardiotoxicity than conventional doxorubicin; however, there is little to no improvement in efficacy. Other liposomal formulations have been developed containing cell targeting groups, such as the folate receptor or Her-2 antibody fragments (Gabizon et al., *Clin Cancer Res.* 2003 Dec. 15; 9(17):6551-9, Laginha et. al. *J Drug Target.* 2008 August; 16(7):605-10, Yamada, A. et. al., *Clin Cancer Res.* 2008 Dec. 15; 14(24):8161-8). Currently, liposomal doxorubicin is the only doxorubicin formulation approved for human use aside from conventional doxorubicin.

Other types of formulations include doxorubicin-polymer conjugates or doxorubicin loaded nanoparticles (Wong, H et al., *Pharm Res.* 2006 July; 23(7):1574-85). Lee et al. describes doxorubicin loaded into polyester dendrimers (Lee et. al., *Proc Natl Acad Sci USA.* 2006 Nov. 7; 103(45): 16649-54). However, it is well known that dendrimers are difficult to manufacture and exhibit poor circulation times in vivo. Other groups have developed doxorubicin conjugated to polymers or cell-targeting peptides (Ryppa, C. et. al. *Bioconjug Chem.* 2008 July; 19(7):1414-22, Meyer-Losic, F. et. al, *J Med. Chem.* 2006 Nov. 16; 49(23):6908-16, Bibby, D. et. al., *Int J.*

*Pharm.* 2005 Apr. 11; 293(1-2):281-90). A disadvantage of these types of systems is that doxorubicin is inadequately shielded from degradation in the bloodstream, or poor biocompatibily of the polymers used.

Micellar systems of encapsulated doxorubicin have been reported. Polymeric micelles are particles that are self-assembled from block copolymers in aqueous solutions. Examples of previously described doxorubicin-loaded micellar formulations can be found in Nasongkla, N., et. al., *Angew Chem Int Ed Engl.* 2004 Nov. 26; 43(46):6323-7, Shuai, X. et. al., *J Control Release.* 2004 Aug. 27; 98(3):415-26, Gao, Z. et. al., *J Drug Target.* 2005 August; 13(7):391-7, Lee, E. et. al., *J Control Release.* 2005 Mar. 21; 103(2):405-18, Gillies, E. et. al., *Bioconjug Chem.* 2005 March-April; 16(2):361-8, Kataoka, K. et. al. J Control Release. 2000 Feb. 14; 64(1-3): 143-53, and Liu, S., et. al., *Biomaterials.* 2007 March; 28(7): 1423-33. One limitation of these micellar formulations is that they do not possess a crosslinkable or other chemical method to entrap doxorubicin in the core of the micelle thereby enabling the needed extended circulation times. Alternatively, some micellar systems utilize covalent attachment of doxorubicin to polymers (Yoo, H. et. al., *J Control Release.* 2004 Nov. 24; 100(2):247-56, Bae, Y. et. al., *Angew Chem Int Ed Engl.* 2003 Oct. 6; 42(38):4640-3). However, such methods of covalent attachment of doxorubicin to polymers results in a reduction in overall bioavailability.

According to one embodiment, the present invention provides a micelle comprising a multiblock copolymer having an anthracycline encapsulated therein.

According another embodiment, the present invention provides a stabilized or crosslinked micelle comprising a multiblock copolymer having an anthracycline encapsulated therein.

In certain embodiments, the multiblock copolymer comprises a hydrophilic poly(ethylene glycol) block, a carboxylic acid-containing poly(amino acid) block, and a hydrophobic poly(amino acid) block characterized in that the resulting micelle has an inner core, a carboxylic acid-containing outer core, and a hydrophilic shell. It will be appreciated that the hydrophilic poly(ethylene glycol) block corresponds to the hydrophilic shell, stabilizing carboxylic acid-containing poly (amino acid) block corresponds to the carboxylic acid-containing outer core, and the hydrophobic poly(amino acid) block corresponds to the inner core.

In other embodiments, the multiblock copolymer comprises a hydrophilic poly(ethylene glycol) block, a imidazole-containing poly(amino acid) block, and a hydrophobic poly(amino acid) block characterized in that the resulting micelle has an inner core, an imidazole-containing outer core, and a hydrophilic shell. It will be appreciated that the hydrophilic poly(ethylene glycol) block corresponds to the hydrophilic shell, stabilizing imidazole-containing poly(amino acid) block corresponds to the imidazole-containing outer core, and the hydrophobic poly(amino acid) block corresponds to the inner core.

In certain embodiments, the multiblock copolymer comprises a hydrophilic poly(ethylene glycol) block, a carboxylic acid-containing poly(amino acid) block, and a hydrophobic D,L mixed poly(amino acid) block characterized in that the resulting micelle has an inner core, a carboxylic acid-containing outer core, and a hydrophilic shell. It will be appreciated that the hydrophilic poly(ethylene glycol) block corresponds to the hydrophilic shell, stabilizing carboxylic acid-containing poly(amino acid) block corresponds to the carboxylic acid-containing outer core, and the hydrophobic D,L mixed poly(amino acid) block corresponds to the inner core.

In other embodiments, the multiblock copolymer comprises a hydrophilic poly(ethylene glycol) block, a imidazole-containing poly(amino acid) block, and a hydrophobic D,L mixed poly(amino acid) block characterized in that the resulting micelle has an inner core, an imidazole-containing outer core, and a hydrophilic shell. It will be appreciated that the hydrophilic poly(ethylene glycol) block corresponds to the hydrophilic shell, stabilizing imidazole-containing poly(amino acid) block corresponds to the imidazole-containing outer core, and the hydrophobic D,L mixed poly(amino acid) block corresponds to the inner core.

2. Definitions

Compounds of this invention include those described generally above, and are further illustrated by the embodiments, sub-embodiments, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As used herein, the term "multiblock copolymer" refers to a polymer comprising one synthetic polymer portion and two or more poly(amino acid) portions. Such multi-block copolymers include those having the format W—X'—X", wherein W is a synthetic polymer portion and X and X' are poly(amino acid) chains or "amino acid blocks". In certain embodiments, the multiblock copolymers of the present invention are triblock copolymers. As described herein, one or more of the amino acid blocks may be "mixed blocks", meaning that these blocks can contain a mixture of amino acid monomers thereby creating multiblock copolymers of the present invention. In some embodiments, the multiblock copolymers of the present invention comprise a mixed amino acid block and are tetrablock copolymers.

As used herein, the term "portion" or "block" refers to a repeating polymeric sequence of defined composition. A portion or a block may consist of a single monomer or may be comprise of on or more monomers, resulting in a "mixed block".

One skilled in the art will recognize that a monomer repeat unit is defined by parentheses around the repeating monomer unit. The number (or letter representing a numerical range) on the lower right of the parentheses represents the number of monomer units that are present in the polymer chain. In the case where only one monomer represents the block (e.g. a homopolymer), the block will be denoted solely by the parentheses. In the case of a mixed block, multiple monomers comprise a single, continuous block. It will be understood that brackets will define a portion or block. For example, one block may consist of four individual monomers, each defined by their own individual set of parentheses and number of repeat units present. All four sets of parentheses will be enclosed by a set of brackets, denoting that all four of these monomers combine in random, or near random, order to comprise the mixed block. For clarity, the randomly mixed block of [BCADDCBADABCDABC] would be represented in shorthand by $[(A)_4(B)_4(C)_4(D)_4]$.

As used herein, the term "triblock copolymer" refers to a polymer comprising one synthetic polymer portion and two poly(amino acid) portions.

As used herein, the term "inner core" as it applies to a micelle of the present invention refers to the center of the micelle formed by the hydrophobic poly(amino acid) block. In accordance with the present invention, the inner core is not crosslinked. By way of illustration, in a triblock polymer of the format W—X'—X", as described above, the inner core corresponds to the X" block.

As used herein, the term "outer core" as it applies to a micelle of the present invention refers to the layer formed by the first poly(amino acid) block. The outer core lies between the inner core and the hydrophilic shell. In accordance with the present invention, the outer core is either crosslinkable or is cross-linked. By way of illustration, in a triblock polymer of the format W—X'—X", as described above, the outer core corresponds to the X' block. It is contemplated that the X' block can be a mixed block.

As used herein, the terms "drug-loaded" and "encapsulated", and derivatives thereof, are used interchangeably. In accordance with the present invention, a "drug-loaded" micelle refers to a micelle having a drug, or therapeutic agent, situated within the core of the micelle. In certain instances, the drug or therapeutic agent is situated at the interface between the core and the hydrophilic coronoa. This is also referred to as a drug, or therapeutic agent, being "encapsulated" within the micelle.

As used herein, the term "polymeric hydrophilic block" refers to a polymer that is not a poly(amino acid) and is hydrophilic in nature. Such hydrophilic polymers are well known in the art and include polyethyleneoxide (also referred to as polyethylene glycol or PEG), and derivatives thereof, poly(N-vinyl-2-pyrolidone), and derivatives thereof, poly(N-isopropylacrylamide), and derivatives thereof, poly(hydroxyethyl acrylate), and derivatives thereof, poly(hydroxylethyl methacrylate), and derivatives thereof, and polymers of N-(2-hydroxypropoyl)methacrylamide (HMPA) and derivatives thereof.

As used herein, the term "poly(amino acid)" or "amino acid block" refers to a covalently linked amino acid chain wherein each monomer is an amino acid unit. Such amino acid units include natural and unnatural amino acids. In certain embodiments, each amino acid unit of the optionally a crosslinkable or crosslinked poly(amino acid block) is in the L-configuration. Such poly(amino acids) include those having suitably protected functional groups. For example, amino acid monomers may have hydroxyl or amino moieties which are optionally protected by a suitable hydroxyl protecting group or a suitable amine protecting group, as appropriate. Such suitable hydroxyl protecting groups and suitable amine protecting groups are described in more detail herein, infra. As used herein, an amino acid block comprises one or more monomers or a set of two or more monomers. In certain embodiments, an amino acid block comprises one or more monomers such that the overall block is hydrophilic. In still other embodiments, amino acid blocks of the present invention include random amino acid blocks, ie blocks comprising a mixture of amino acid residues.

As used herein, the term "D,L-mixed poly(amino acid) block" refers to a poly(amino acid) block wherein the poly (amino acid) consists of a mixture of amino acids in both the D- and L-configurations. In certain embodiments, the D,L-mixed poly(amino acid) block is hydrophobic. In other embodiments, the D,L-mixed poly(amino acid) block consists of a mixture of D-configured hydrophobic amino acids and L-configured hydrophilic amino acid side-chain groups such that the overall poly(amino acid) block comprising is hydrophobic.

Exemplary poly(amino acids) include poly(benzyl glutamate), poly(benzyl aspartate), poly(L-leucine-co-tyrosine), poly(D-leucine-co-tyrosine), poly(L-phenylalanine-co-tyrosine), poly(D-phenylalanine-co-tyrosine), poly(L-leucine-coaspartic acid), poly(D-leucine-co-aspartic acid), poly(L-phenylalanine-co-aspartic acid), poly(D-phenylalanine-co-aspartic acid).

As used herein, the phrase "natural amino acid side-chain group" refers to the side-chain group of any of the 20 amino acids naturally occurring in proteins. Such natural amino acids include the nonpolar, or hydrophobic amino acids, glycine, alanine, valine, leucine isoleucine, methionine, phenylalanine, tryptophan, and proline. Cysteine is sometimes classified as nonpolar or hydrophobic and other times as polar. Natural amino acids also include polar, or hydrophilic amino acids, such as tyrosine, serine, threonine, aspartic acid (also known as aspartate, when charged), glutamic acid (also known as glutamate, when charged), asparagine, and glutamine. Certain polar, or hydrophilic, amino acids have charged side-chains. Such charged amino acids include lysine, arginine, and histidine. One of ordinary skill in the art would recognize that protection of a polar or hydrophilic amino acid side-chain can render that amino acid nonpolar. For example, a suitably protected tyrosine hydroxyl group can render that tyroine nonpolar and hydrophobic by virtue of protecting the hydroxyl group.

As used herein, the phrase "unnatural amino acid side-chain group" refers to amino acids not included in the list of 20 amino acids naturally occurring in proteins, as described above. Such amino acids include the D-isomer of any of the 20 naturally occurring amino acids. Unnatural amino acids also include homoserine, ornithine, and thyroxine. Other unnatural amino acids side-chains are well know to one of ordinary skill in the art and include unnatural aliphatic side chains. Other unnatural amino acids include modified amino acids, including those that are N-alkylated, cyclized, phosphorylated, acetylated, amidated, azidylated, labelled, and the like.

As used herein, the term "tacticity" refers to the stereochemistry of the poly(amino acid) hydrophobic block. A poly(amino acid) block consisting of a single stereoisomer (e.g. all L isomer) is referred to as "isotactic". A poly(amino acid) consisting of a random incorporation of D and L amino acid monomers is referred to as an "atactic" polymer. A poly(amino acid) with alternating stereochemistry (e.g. . . . DLDLDL . . . ) is referred to as a "syndiotactic" polymer. Polymer tacticity is described in more detail in "Principles of Polymerization", 3rd Ed., G. Odian, John Wiley & Sons, New York: 1991, the entire contents of which are hereby incorporated by reference.

As used herein, the term anthracycline refers to a class of antibiotics derived from Streptomyces bacteria. Examples include, but are not limited to, daunorubicin (also known as Daunomycin or daunomycin cerubidine), doxorubicin (also known as DOX, hydroxydaunorubicin, or adriamycin), epirubicin (also known as Ellence or Pharmorubicin), idarubicin (also known as 4-demethoxydaunorubicin, Zavedos, or Idamycin), and valrubicin (also known as N-trifluoroacetyladriamycin-14-valerate or Valstar) and salts thereof.

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-20 carbon atoms. In some embodiments, aliphatic groups contain 1-10 carbon atoms. In other embodiments, aliphatic groups contain 1-8 carbon atoms. In still other embodiments, aliphatic groups contain 1-6 carbon atoms, and in yet other embodiments aliphatic groups contain 1-4 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as in neutron scattering experiments, as analytical tools or probes in biological assays.

As used herein, the term "detectable moiety" is used interchangeably with the term "label" and relates to any moiety capable of being detected (e.g., primary labels and secondary labels). A "detectable moiety" or "label" is the radical of a detectable compound.

"Primary" labels include radioisotope-containing moieties (e.g., moieties that contain $^{32}$P, $^{33}$P, $^{35}$S, or $^{14}$C), mass-tags, and fluorescent labels, and are signal-generating reporter groups which can be detected without further modifications.

Other primary labels include those useful for positron emission tomography including molecules containing radioisotopes (e.g. $^{18}$F) or ligands with bound radioactive metals (e.g. $^{62}$Cu). In other embodiments, primary labels are contrast agents for magnetic resonance imaging such as gadolinium, gadolinium chelates, or iron oxide (e.g. $Fe_3O_4$ and $Fe_2O_3$) particles. Similarly, semiconducting nanoparticles (e.g. cadmium selenide, cadmium sulfide, cadmium telluride) are useful as fluorescent labels. Other metal nanoparticles (e.g colloidal gold) also serve as primary labels.

Unless otherwise indicated, radioisotope-containing moieties are optionally substituted hydrocarbon groups that contain at least one radioisotope. Unless otherwise indicated, radioisotope-containing moieties contain from 1-40 carbon atoms and one radioisotope. In certain embodiments, radioisotope-containing moieties contain from 1-20 carbon atoms and one radioisotope.

The terms "fluorescent label", "fluorescent group", "fluorescent compound", "fluorescent dye", and "fluorophore", as used herein, refer to compounds or moieties that absorb light energy at a defined excitation wavelength and emit light energy at a different wavelength. Examples of fluorescent compounds include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethylrhodamine (TMR), Carboxytetramethylrhodamine (TAMRA), Texas Red, Texas Red-X.

3. Description of Exemplary Embodiments

A. Anthracycline Loaded Multiblock Copolymer Micelles

As described generally above, the present invention provides a micelle comprising a multiblock copolymer having an anthracycline encapsulated therein.

According another embodiment, the present invention provides a stabilized or crosslinked micelle comprising a multiblock copolymer having an anthracycline encapsulated therein.

In certain embodiments, the multiblock copolymer comprises a hydrophilic poly(ethylene glycol) block, a carboxylic acid-containing poly(amino acid) block, and a hydrophobic poly(amino acid) block characterized in that the resulting micelle has an inner core, a carboxylic acid-containing outer core, and a hydrophilic shell. It will be appreciated that the hydrophilic poly(ethylene glycol) block corresponds to the hydrophilic shell, stabilizing carboxylic acid-containing poly (amino acid) block corresponds to the carboxylic acid-containing outer core, and the hydrophobic poly(amino acid) block corresponds to the inner core.

In other embodiments, the multiblock copolymer comprises a hydrophilic poly(ethylene glycol) block, a imidazole-containing poly(amino acid) block, and a hydrophobic poly(amino acid) block characterized in that the resulting micelle has an inner core, an imidazole-containing outer core, and a hydrophilic shell. It will be appreciated that the hydrophilic poly(ethylene glycol) block corresponds to the hydrophilic shell, stabilizing imidazole-containing poly(amino acid) block corresponds to the imidazole-containing outer core, and the hydrophobic poly(amino acid) block corresponds to the inner core.

In certain embodiments, the multiblock copolymer comprises a hydrophilic poly(ethylene glycol) block, a carboxylic acid-containing poly(amino acid) block, and a hydrophobic D,L mixed poly(amino acid) block characterized in that the resulting micelle has an inner core, a carboxylic acid-containing outer core, and a hydrophilic shell. It will be appreciated that the hydrophilic poly(ethylene glycol) block corresponds to the hydrophilic shell, stabilizing carboxylic acid-containing poly(amino acid) block corresponds to the carboxylic acid-containing outer core, and the hydrophobic D,L mixed poly(amino acid) block corresponds to the inner core.

In other embodiments, the multiblock copolymer comprises a hydrophilic poly(ethylene glycol) block, a imidazole-containing poly(amino acid) block, and a hydrophobic D,L mixed poly(amino acid) block characterized in that the resulting micelle has an inner core, an imidazole-containing outer core, and a hydrophilic shell. It will be appreciated that the hydrophilic poly(ethylene glycol) block corresponds to the hydrophilic shell, stabilizing imidazole-containing poly (amino acid) block corresponds to the imidazole-containing outer core, and the hydrophobic D,L mixed poly(amino acid) block corresponds to the inner core.

Amphiphilic multiblock copolymers, as described herein, can self-assemble in aqueous solution to form nano- and micron-sized structures. In water, these amphiphilic multiblock copolymers assemble by multi-molecular micellization when present in solution above the critical micelle concentration (CMC). Without wishing to be bound by any particular theory, it is believed that the hydrophobic poly(amino acid) portion or "block" of the copolymer collapses to form the micellar core, while the hydrophilic PEG block forms a peripheral corona and imparts water solubility. In certain embodiments, the multiblock copolymers in accordance with the present invention possess distinct hydrophobic and hydrophilic segments that form micelles. In addition, these multiblock polymers optionally comprise a poly(amino acid) block which contains functionality suitable for crosslinking. It will be appreciated that this functionality is found on the corresponding amino acid side-chain.

In certain embodiments, the present invention provides a micelle having an anthracycline encapsulated therein, wherein said micelle comprises a multiblock copolymer which comprises:
 a hydrophilic poly(ethylene glycol) block;
 a stabilizing carboxylic acid-containing poly(amino acid) block; and
 a hydrophobic D,L-mixed poly(amino acid) block.

In some embodiments, the stabilizing carboxylic acid-containing poly(amino acid) block is a poly(glutamic acid) block or a poly(aspartic acid) block. In other embodiments, the stabilizing carboxylic acid-containing poly(amino acid) block is a random poly(glutamic acid-co-apartic acid) block.

In certain embodiments, the present invention provides a micelle having an anthracycline encapsulated therein, wherein said micelle comprises a multiblock copolymer which comprises:
 a hydrophilic poly(ethylene glycol) block;
 a stabilizing imidazole-containing poly(amino acid) block; and
 a hydrophobic D,L-mixed poly(amino acid) block.

In some embodiments, the stabilizing imidazole-containing poly(amino acid) block is histadine. In other embodiments, the stabilizing imidazole-containing poly(amino acid) block is an histamine derivative.

The "hydrophobic D,L-mixed poly(amino acid)" block, as described herein, consists of a mixture of D and L enantiomers to facilitate the encapsulation of hydrophobic moieties. It is well established that homopolymers and copolymers of amino acids, consisting of a single stereoisomer, may exhibit secondary structures such as the a-helix or β-sheet. See *a-Aminoacid-N-Caroboxy-Anhydrides and Related Heterocycles*, H. R. Kricheldorf, Springer-Verlag, 1987. For example, poly(L-benzyl glutamate) typically exhibits an a-helical conformation; however this secondary structure can be disrupted by a change of solvent or temperature (see *Advances in Protein Chemistry XVI*, P. Urnes and P. Doty, Academic Press, New York 1961). The secondary structure can also be disrupted by the incorporation of structurally dissimilar amino acids such as b-sheet forming amino acids (e.g. proline) or through the incorporation of amino acids with dissimilar stereochemistry (e.g. mixture of D and L stereoisomers), which results in poly(amino acids) with a random coil conformation. See Sakai, R.; Ikeda; S.; Isemura, T. *Bull Chem. Soc. Japan* 1969, 42, 1332-1336, Paolillo, L.; Temussi, P. A.; Bradbury, E. M.; Crane-Robinson, C. *Biopolymers* 1972, 11, 2043-2052, and Cho, I.; Kim, J. B.; Jung, H. J. *Polymer* 2003, 44, 5497-5500.

While the methods to influence secondary structure of poly(amino acids) have been known for some time, it has been suprisingly discovered that block copolymers of the present invention, possessing a random coil conformation, are particularly useful for encapsulation of hydrophobic molecules when compared to similar block copolymers possessing a helical segment. Without wishing to be bound to any particular theory, it is believed that provided block copolymers having a coil-coil conformation allow for efficient packing and loading of hydrophobic moieties within the micelle core, while the steric demands of a rod-coil conformation for a helix-containing block copolymer results in less effective encapsulation.

In certain embodiments, the PEG block possesses a molecular weight of approx. 10,000 Da (225 repeat units). In other embodiments, the PEG block possesses a molecular weight of approx. 12,000 Da (270 repeat units). In yet other embodiments, the PEG block possesses a molecular weight of approx. 8,000 Da (180 repeat units). In certain embodiments, the PEG block possesses a molecular weight of approx. 20,000 Da (450 repeat units). Without wishing to be bound by theory, it is believed that this particular PEG chain length imparts adequate water-solubility to the micelles and provides relatively long in vivo circulation times.

In certain embodiments, the present invention provides a micelle, having an anthracycline encapsulated therein, comprising a multiblock copolymer of formula I:

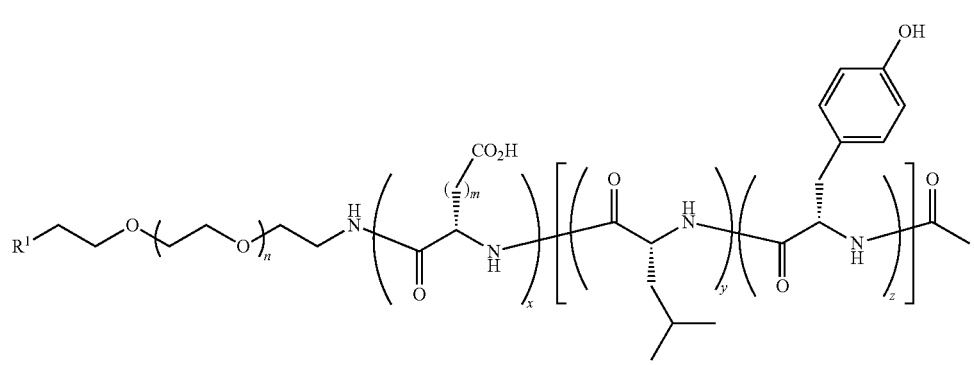

wherein:
R¹ is —OCH₃, —N₃, or

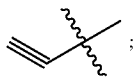 [SMILES: *C#C]

n is 110 to 450;
m is 1 or 2;
x is 3 to 50;
y is 5 to 50; and
z is 5 to 50.

In certain embodiments, the present invention provides a micelle, having an anthracycline encapsulated therein, comprising a multiblock copolymer of formula I:

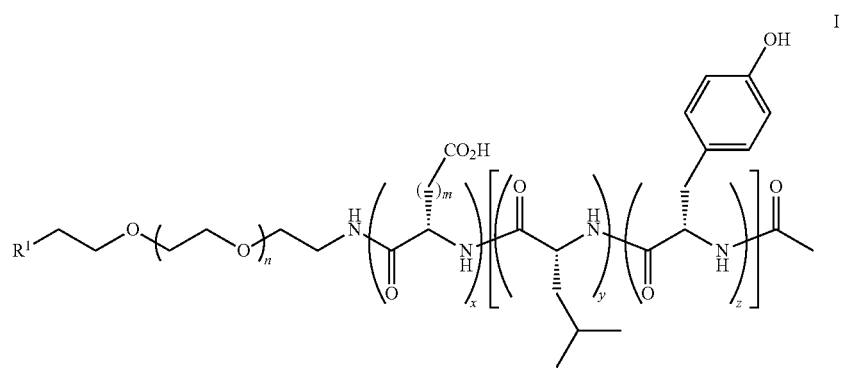

wherein:
R¹ is —N₃;
n is about 270;
m is 1 or 2;
x is about 10;
y is about 20; and
z is about 20.

As defined generally above, the n group of formula I is 110-450. In certain embodiments, the present invention provides compounds of formula I, as described above, wherein n is about 225. In other embodiments, n is about 270. In other embodiments, n is about 350. In other embodiments, n is about 110. In other embodiments, n is about 450. In other embodiments, n is selected from 110±10, 180±10, 225±10, 275±10, 315±10, or 450±10.

As defined generally above, the m group of formula I is 1 or 2. In some embodiments, m is 1 thereby forming a poly(aspartic acid) block. In some embodiments, m is 2 thereby forming a poly(glutamic acid) block.

In certain embodiments, the x group of formula I is about 3 to about 50. In certain embodiments, the x group of formula I is about 10. In other embodiments, x is about 20. According to yet another embodiment, x is about 15. In other embodiments, x is about 5. In other embodiments, x is selected from 5±3, 10±3, 10±5, 15±5, or 20±5.

In certain embodiments, the y group of formula I is about 5 to about 50. In certain embodiments, the y group of formula I is about 10. In other embodiments, y is about 20. According to yet another embodiment, y is about 15. In other embodiments, y is about 30. In other embodiments, y is selected from 10±3, 15±3, 17±3, 20±5, or 30±5.

In certain embodiments, the z group of formula I is about 5 to about 50. In certain embodiments, the z group of formula I is about 10. In other embodiments, z is about 20. According to yet another embodiment, z is about 15. In other embodiments, z is about 30. In other embodiments, z is selected from 10±3, 15±3, 17±3, 20±5, or 30±5.

In some embodiments, the R¹ group of a compound of formula I is —N₃ suitable for Click chemistry, and therefore useful for conjugating said compound to biological systems or macromolecules such as proteins, viruses, and cells, to name but a few. The Click reaction is known to proceed quickly and selectively under physiological conditions. In contrast, most conjugation reactions are carried out using the primary amine functionality on proteins (e.g. lysine or protein end-group). Because most proteins contain a multitude of lysines and arginines, such conjugation occurs uncontrollably at multiple sites on the protein. This is particularly problematic when lysines or arginines are located around the active site of an enzyme or other biomolecule. Thus, another embodiment of the present invention provides a method of conjugating the azide end group of a compound of formula I to a macromolecule via Click chemistry. Yet another embodiment of the present invention provides a macromolecule conjugated to a compound of formula I via the R¹ azide group.

In certain embodiments, the present invention provides a micelle, having an anthracycline encapsulated therein, comprising a multiblock copolymer of formula II:

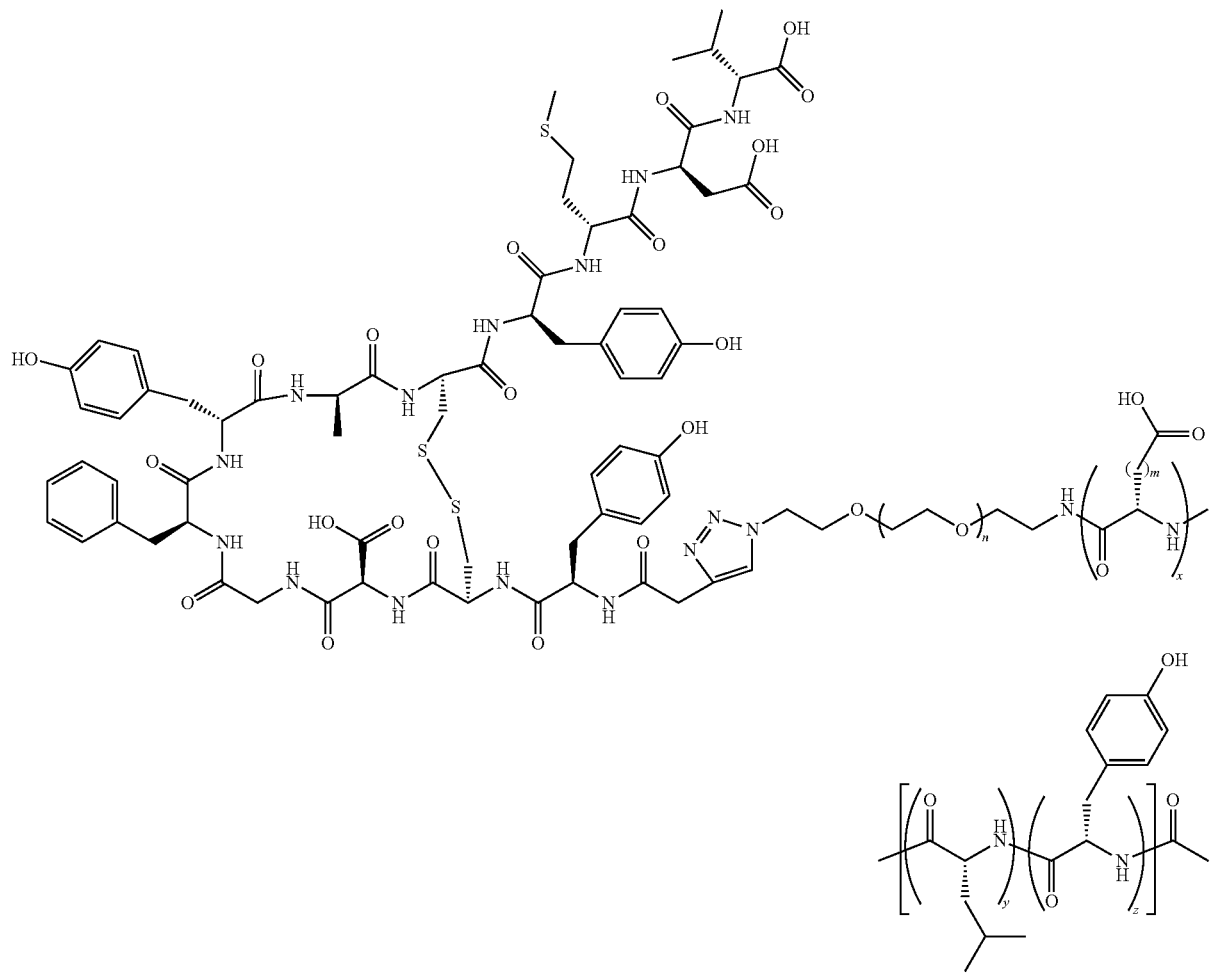

wherein:
n is 110 to 450;
m is 1 or 2;
x is 3 to 50;
y is 5 to 50; and
z is 5 to 50.

As defined generally above, the n group of formula II is 110-450. In certain embodiments, the present invention provides compounds of formula II, as described above, wherein n is about 225. In other embodiments, n is about 270. In other embodiments, n is about 350. In other embodiments, n is about 110. In other embodiments, n is about 450. In other embodiments, n is selected from 110±10, 180±10, 225±10, 275±10, 315±10, or 450±10.

In certain embodiments, the x group of formula II is about 3 to about 50. In certain embodiments, the x group of formula II is about 10. In other embodiments, x is about 20. According to yet another embodiment, x is about 15. In other embodiments, x is about 5. In other embodiments, x is selected from 5±3, 10±3, 10±5, 15±5, or 20±5.

In certain embodiments, the y group of formula II is about 5 to about 50. In certain embodiments, the y group of formula II is about 10. In other embodiments, y is about 20. According to yet another embodiment, y is about 15. In other embodiments, y is about 30. In other embodiments, y is selected from 10±3, 15±3, 17±3, 20±5, or 30±5.

In certain embodiments, the z group of formula II is about 5 to about 50. In certain embodiments, the z group of formula II is about 10. In other embodiments, z is about 20. According to yet another embodiment, z is about 15. In other embodiments, z is about 30. In other embodiments, z is selected from 10±3, 15±3, 17±3, 20±5, or 30±5.

In some embodiments, the present invention provides a micelle, having an anthracycline encapsulated therein, comprising a multiblock copolymer of formula II, wherein n is about 270, x is about 10, y is about 20, and z is about 20.

In certain embodiments, the present invention provides a micelle, having an anthracycline encapsulated therein, comprising a multiblock copolymer of formula I and a multiblock copolymer of formula II, wherein each of formula I and formula II are as defined above and described herein.

In some embodiments, the present invention provides a micelle, having an anthracycline encapsulated therein, comprising a multiblock copolymer of formula I and a multiblock copolymer of formula II, wherein each of formula I and formula II are as defined above and described herein, wherein the ratio of Formula I to Formula II is between about 1000:1 and about 1:1. In other embodiments, the ratio is about 1000:1, about 100:1, about 50:1, about 33:1, about 25:1, about 20:1, about 10:1, about 5:1, or about 4:1. In yet other embodiments, the ratio is between about 100:1 and about 25:1.

In certain embodiments, the present invention provides a micelle, having an anthracycline encapsulated therein, comprising a multiblock copolymer of formula III:

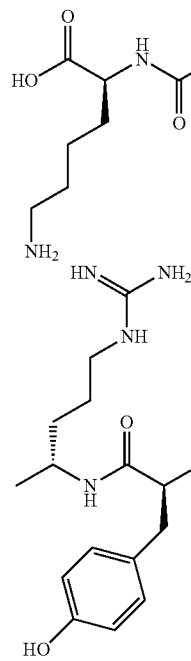
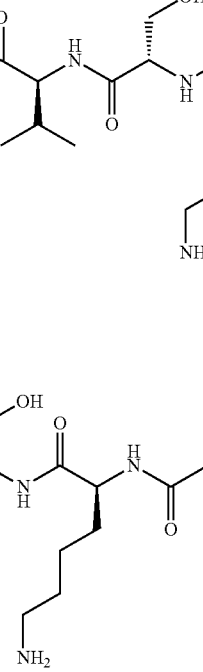
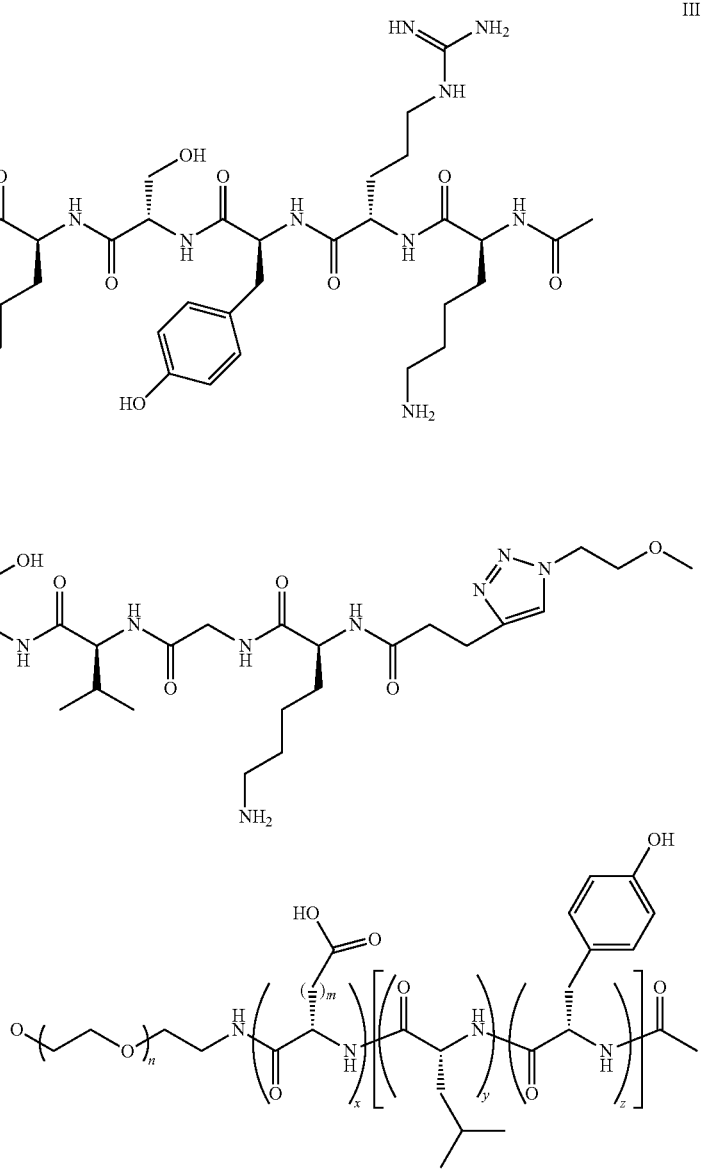

III wherein:
n is 110 to 450;
x is 3 to 50;
y is 5 to 50; and
z is 5 to 50.

As defined generally above, the n group of formula III is 110-450. In certain embodiments, the present invention provides compounds of formula III, as described above, wherein n is about 225. In other embodiments, n is about 270. In other embodiments, n is about 350. In other embodiments, n is about 110. In other embodiments, n is about 450. In other embodiments, n is selected from 110±10, 180±10, 225±10, 275±10, 315±10, or 450±10.

In certain embodiments, the x group of formula III is about 3 to about 50. In certain embodiments, the x group of formula III is about 10. In other embodiments, x is about 20. According to yet another embodiment, x is about 15. In other embodiments, x is about 5. In other embodiments, x is selected from 5±3, 10±3, 10±5, 15±5, or 20±5.

In certain embodiments, the y group of formula III is about 5 to about 50. In certain embodiments, the y group of formula III is about 10. In other embodiments, y is about 20. According to yet another embodiment, y is about 15. In other embodiments, y is about 30. In other embodiments, y is selected from 10±3, 15±3, 17±3, 20±5, or 30±5.

In certain embodiments, the z group of formula III is about 5 to about 50. In certain embodiments, the z group of formula III is about 10. In other embodiments, z is about 20. According to yet another embodiment, z is about 15. In other embodiments, z is about 30. In other embodiments, z is selected from 10±3, 15±3, 17±3, 20±5, or 30±5.

In certain embodiments, the present invention provides a micelle, having an anthracycline encapsulated therein, comprising a multiblock copolymer of formula III wherein wherein n is about 270, x is about 10, y is about 20, and z is about 20.

In some embodiments, the present invention provides a micelle, having an anthracycline encapsulated therein, comprising a multiblock copolymer of formula I and a multiblock copolymer of formula III, wherein each of formula I and formula III are as defined above and described herein, wherein the ratio of Formula I to Formula III is between about 1000:1 and about 1:1. In other embodiments, the ratio is about 1000:1, about 100:1, about 50:1, about 33:1, about 25:1, about 20:1, about 10:1, about 5:1, or about 4:1. In yet other embodiments, the ratio is between about 100:1 and about 25:1.

In certain embodiments, the present invention provides a micelle, having an anthracycline encapsulated therein, comprising a multiblock copolymer of formula IV:

embodiments, x is about 5. In other embodiments, x is selected from 5±3, 10±3, 10±5, 15±5, or 20±5.

In certain embodiments, the y group of formula IV is about 5 to about 50. In certain embodiments, the y group of formula IV is about 10. In other embodiments, y is about 20. According to yet another embodiment, y is about 15. In other embodiments, y is about 30. In other embodiments, y is selected from 10±3, 15±3, 17±3, 20±5, or 30±5.

In certain embodiments, the z group of formula IV is about 5 to about 50. In certain embodiments, the z group of formula IV is about 10. In other embodiments, z is about 20. According to yet another embodiment, z is about 15. In other embodiments, z is about 30. In other embodiments, z is selected from 10±3, 15±3, 17±3, 20±5, or 30±5.

In certain embodiments, the present invention provides a micelle, having an anthracycline encapsulated therein, com-

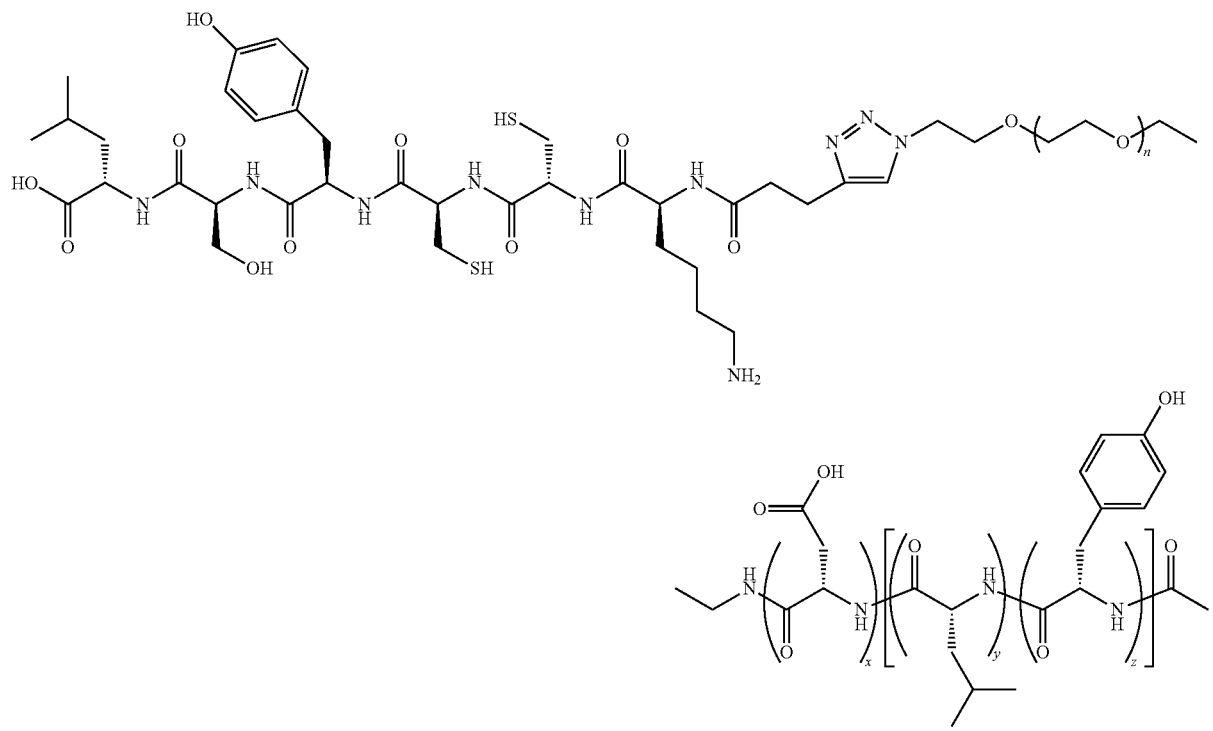

IV wherein:
n is 110 to 450;
x is 3 to 50;
y is 5 to 50; and
z is 5 to 50.

As defined generally above, the n group of formula IV is 110-450. In certain embodiments, the present invention provides compounds of formula IV, as described above, wherein n is about 225. In other embodiments, n is about 270. In other embodiments, n is about 350. In other embodiments, n is about 110. In other embodiments, n is about 450. In other embodiments, n is selected from 110±10, 180±10, 225±10, 275±10, 315±10, or 450±10.

In certain embodiments, the x group of formula IV is about 3 to about 50. In certain embodiments, the x group of formula IV is about 10. In other embodiments, x is about 20. According to yet another embodiment, x is about 15. In other prising a multiblock copolymer of formula IV wherein wherein n is about 270, x is about 10, y is about 20, and z is about 20.

In some embodiments, the present invention provides a micelle, having an anthracycline encapsulated therein, comprising a multiblock copolymer of formula I and a multiblock copolymer of formula IV, wherein each of formula I and formula IV are as defined above and described herein, wherein the ratio of Formula I to Formula IV is between about 1000:1 and about 1:1. In other embodiments, the ratio is about 1000:1, about 100:1, about 50:1, about 33:1, about 25:1, about 20:1, about 10:1, about 5:1, or about 4:1. In yet other embodiments, the ratio is between about 100:1 and about 25:1.

In certain embodiments, the present invention provides a micelle, having an anthracycline encapsulated therein, comprising a multiblock copolymer of formula V:

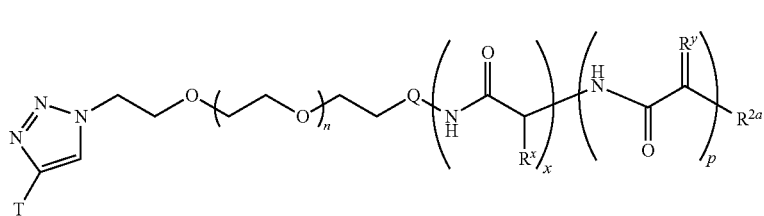

wherein:

n is 10-2500;
x is 0 to 1000;
p is 2 to 1000;
$R^x$ is a natural or unnatural amino acid side-chain group that is capable of crosslinking;
$R^y$ forms a hydrophobic D,L-mixed poly(amino acid) block;
Q is a valence bond or a bivalent, saturated or unsaturated, straight or branched $C_{1-12}$ hydrocarbon chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:
-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;
$R^{2a}$ is a mono-protected amine, a di-protected amine, —N($R^4$)$_2$, —NR$^4$C(O)R$^4$, —NR$^4$C(O)N($R^4$)$_2$, —NR$^4$C(O)OR$^4$, or —NR$^4$SO$_2$R$^4$;
each $R^4$ is independently hydrogen or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety, or:
two $R^4$ on the same nitrogen atom are taken together with said nitrogen atom to form an optionally substituted 4-7 membered saturated, partially unsaturated, or aryl ring having 1-4 heteroatoms independently selected from nitrogen, oxygen, or sulfur, and T is a targeting group moiety.

In certain embodiments, the p group of formula V is about 5 to about 500. In certain embodiments, the p group of formula V is about 10 to about 250. In other embodiments, p is about 10 to about 50. According to yet another embodiment, p is about 15 to about 40. In other embodiments, p is about 20 to about 40. According to yet another embodiment, p is about 50 to about 75. According to other embodiments, x and p are independently about 10 to about 100.

In some embodiments, x is 0. In certain embodiments, x is 5-50. In other embodiments, x is 5-25. In certain embodiments, p is 5-50. In other embodiments, p is 5-10. In other embodiments, p is 10-20. In certain embodiments, x and p add up to about 30 to about 60. In still other embodiments, x is 1-20 repeat units and p is 10-50 repeat units. In certain embodiments, the x group of formula V is about 3 to about 50.

In certain embodiments, the x group of formula V is about 10. In other embodiments, x is about 20. According to yet another embodiment, x is about 15. In other embodiments, x is about 5. In other embodiments, x is selected from 5±3, 10±3, 10±5, 15±5, or 20±5.

As defined generally above, the Q group of formula V is a valence bond or a bivalent, saturated or unsaturated, straight or branched $C_{1-12}$ hydrocarbon chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur. In certain embodiments, Q is a valence bond. In other embodiments, Q is a bivalent, saturated $C_{1-12}$ alkylene chain, wherein 0-6 methylene units of Q are independently replaced by -Cy-, —O—, —NH—, —S—, —OC(O)—, —C(O)O—, or —C(O)—, wherein -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur.

In certain embodiments, the Q group of formula V is -Cy- (i.e. a $C_1$ alkylene chain wherein the methylene unit is replaced by -Cy-), wherein -Cy- is an optionally substituted 5-8 membered bivalent, saturated, partially unsaturated, or aryl ring having 0-4 heteroatoms independently selected from nitrogen, oxygen, or sulfur. According to one aspect of the present invention, -Cy- is an optionally substituted bivalent aryl group. According to another aspect of the present invention, -Cy- is an optionally substituted bivalent phenyl group. In other embodiments, -Cy- is an optionally substituted 5-8 membered bivalent, saturated carbocyclic ring. In still other embodiments, -Cy- is an optionally substituted 5-8 membered bivalent, saturated heterocyclic ring having 1-2 heteroatoms independently selected from nitrogen, oxygen, or sulfur. Exemplary -Cy- groups include bivalent rings selected from phenyl, pyridyl, pyrimidinyl, cyclohexyl, cyclopentyl, or cyclopropyl.

In certain embodiments, the $R^x$ group of formula V is a crosslinkable amino acid side-chain group. Such crosslinkable amino acid side-chain groups include tyrosine, serine, cysteine, threonine, aspartic acid (also known as aspartate, when charged), glutamic acid (also known as glutamate, when charged), asparagine, histidine, lysine, arginine, glutamine, or a benzimidazole-functionalized amino acid.

As defined above, the $R^x$ group of formula V is a natural or unnatural amino acid side-chain group capable of forming cross-links. It will be appreciated that a variety of amino acid side-chain functional groups are capable of such cross-linking, including, but not limited to, carboxylate, hydroxyl, thiol, and amino groups. Examples of $R^x$ moieties having functional groups capable of forming cross-links include a glutamic acid side-chain, —$CH_2C(O)OH$, an aspartic acid side-chain, —$CH_2CH_2C(O)OH$, a cystein side-chain, —$CH_2SH$, a serine side-chain, —$CH_2OH$, an aldehyde containing side-chain, —$CH_2C(O)H$, a lysine side-chain, —$(CH_2)_4NH_2$, an arginine side-chain, —$(CH_2)_3NHC(=NH)NH_2$, a histidine side-chain, —$CH_2$-imidazol-4-yl, a aspartic acid (histamine amide) side chain —$C(O)NH$—$CH_2$—$CH_2$-imidazol-4-yl, or a glutamic acid (histamine amide) side chain —$CH_2C(O)NH$—$CH_2$—$CH_2$-imidazol-4-yl. In some embodiments, $R^x$ is a glutamic acid side chain. In other embodiments, $R^x$ is an aspartic acid side chain. In still other embodiments, $R^x$ is a histidine side-chain.

As defined above, the $R^y$ group of formula V forms a hydrophobic D,L-mixed amino acid block. Such hydrophobic amino acid side-chain groups include a suitably protected tyrosine side-chain, a suitably protected serine side-chain, a suitably protected threonine side-chain, phenylalanine, alanine, valine, leucine, tryptophan, proline, benzyl and alkyl glutamates, or benzyl and alkyl aspartates or mixtures thereof. One of ordinary skill in the art would recognize that protection of a polar or hydrophilic amino acid side-chain can render that amino acid nonpolar. For example, a suitably protected tyrosine hydroxyl group can render that tyrosine nonpolar and hydrophobic by virtue of protecting the hydroxyl group. Suitable protecting groups for the hydroxyl, amino, and thiol, and carboylate functional groups of $R^x$ and $R^y$ are as described herein.

In other embodiments, the $R^y$ group of formula V consists of a mixture of D-hydrophobic and L-hydrophilic amino acid side-chain groups such that the overall poly(amino acid) block comprising $R^y$ is hydrophobic and is a mixture of D- and L-configured amino acids. Such mixtures of amino acid side-chain groups include L-tyrosine and D-leucine, L-tyrosine and D-phenylalanine, L-serine and D-phenylalanine, L-aspartic acid and D-phenylalanine, L-glutamic acid and D-phenylalanine, L-tyrosine and D-benzyl glutamate, L-tyrosine and D-benzyl aspartate, L-serine and D-benzyl glutamate, L-serine and D-benzyl aspartate, L-aspartic acid and D-benzyl glutamate, L-aspartic acid and D-benzyl aspartate, L-glutamic acid and D-benzyl glutamate, L-glutamic acid and D-benzyl aspartate, L-aspartic acid and D-leucine, and L-glutamic acid and D-leucine. Ratios (D-hydrophobic to L-hydrophilic) of such amino acid combinations can range between 5-95 mol %.

In certain embodiments, the $R^y$ group of formula V consists of a mixture of D-hydrophobic and L-hydrophobic amino acids. Such mixtures include D-benzyl glutamate and L-benzyl glutamate, D-benzyl aspartate and L-benzyl aspartate, D-benzyl aspartate and L-benzyl glutamate, or D-benzyl glutamate and L-benzyl aspartate.

As defined generally above, the $R^{2a}$ group of formula V is a mono-protected amine, a di-protected amine, —$NHR^4$, —$N(R^4)_2$, —$NHC(O)R^4$, —$NR^4C(O)R^4$, —$NHC(O)OR^4$, —$NHC(O)N(R^4)_2$, —$NR^4C(O)NHR^4$, —$NR^4C(O)N(R^4)_2$, —$NHC(O)OR^4$, —$NR^4C(O)OR^4$, —$NHSO_2R^4$, or —$NR^4SO_2R^4$, wherein each $R^4$ is independently an optionally substituted group selected from aliphatic, a 5-8 membered saturated, partially unsaturated, or aryl ring having 0-4 heteroatoms independently selected from nitrogen, oxygen, or sulfur, an 8-10-membered saturated, partially unsaturated, or aryl bicyclic ring having 0-5 heteroatoms independently selected from nitrogen, oxygen, or sulfur, or a detectable moiety, or two $R^4$ on the same nitrogen atom are taken together with said nitrogen atom to form an optionally substituted 4-7 membered saturated, partially unsaturated, or aryl ring having 1-4 heteroatoms independently selected from nitrogen, oxygen, or sulfur.

In certain embodiments, the $R^{2a}$ group of formula V is —$NHR^4$ or —$N(R^4)_2$ wherein each $R^4$ is an optionally substituted aliphatic group. One exemplary $R^4$ group is 5-norbornen-2-yl-methyl. According to yet another aspect of the present invention, the $R^{2a}$ group of formula I is —$NHR^4$ wherein $R^4$ is a $C_{1-6}$ aliphatic group substituted with $N_3$. Examples include —$CH_2N_3$. In some embodiments, $R^4$ is an optionally substituted $C_{1-6}$ alkyl group. Examples include methyl, ethyl, propyl, butyl, pentyl, hexyl, 2-(tetrahydropyran-2-yloxy)ethyl, pyridin-2-yldisulfanylmethyl, methyldisulfanylmethyl, (4-acetylenylphenyl)methyl, 3-(methoxycarbonyl)-prop-2-ynyl, methoxycarbonylmethyl, 2-(N-methyl-N-(4-acetylenylphenyl)carbonylamino)-ethyl, 2-phthalimidoethyl, 4-bromobenzyl, 4-chlorobenzyl, 4-fluorobenzyl, 4-iodobenzyl, 4-propargyloxybenzyl, 2-nitrobenzyl, 4-(bis-4-acetylenylbenzyl)aminomethyl-benzyl, 4-propargyloxy-benzyl, 4-dipropargylamino-benzyl, 4-(2-propargyloxy-ethyldisulfanyl)benzyl, 2-propargyloxy-ethyl, 2-prop argyldisulfanyl-ethyl, 4-propargyloxy-butyl, 2-(N-methyl-N-propargylamino)ethyl, and 2-(2-dipropargylaminoethoxy)-ethyl. In other embodiments, $R^4$ is an optionally substituted $C_{2-6}$ alkenyl group. Examples include vinyl, allyl, crotyl, 2-propenyl, and but-3-enyl. When $R^4$ group is a substituted aliphatic group, suitable substituents on $R^4$ include $N_3$, CN, and halogen. In certain embodiments, $R^4$ is —$CH_2CN$, —$CH_2CH_2CN$, —$CH_2CH(OCH_3)_2$, 4-(bisbenzyloxymethyl)phenylmethyl, and the like.

According to another aspect of the present invention, the $R^{2a}$ group of formula V is —$NHR^4$ wherein $R^4$ is an optionally substituted $C_{2-6}$ alkynyl group. Examples include —$CC\equiv CH$, —$CH_2C\equiv CH$, —$CH_2C\equiv CCH_3$, and —$CH_2CH_2C\equiv CH$.

In certain embodiments, the $R^{2a}$ group of formula V is —$NHR^4$ wherein $R^4$ is an optionally substituted 5-8-membered aryl ring. In certain embodiments, $R^4$ is optionally substituted phenyl or optionally substituted pyridyl. Examples include phenyl, 4-t-butoxycarbonylaminophenyl, 4-azidomethylphenyl, 4-propargyloxyphenyl, 2-pyridyl, 3-pyridyl, and 4-pyridyl. In certain embodiments, $R^{2a}$ is 4-t-butoxycarbonylaminophenylamino, 4-azidomethylphenamino, or 4-prop argyloxyphenylamino.

In certain embodiments, the $R^{2a}$ group of formula V is —$NHR^4$ wherein $R^4$ is an optionally substituted phenyl ring. Suitable substituents on the $R^4$ phenyl ring include halogen; —$(CH_2)_{0-4}R^\circ$; —$(CH_2)_{0-4}OR^\circ$; —$(CH_2)_{0-4}CH(OR^\circ)_2$; —$(CH_2)_{0-4}SR^\circ$; —$(CH_2)_{0-4}Ph$, which may be substituted with $R^\circ$; —$(CH_2)_{0-4}O(CH_2)_{0-1}Ph$ which may be substituted with $R^\circ$; —$CH=CHPh$, which may be substituted with $R^\circ$; —$NO_2$; —$CN$; —$N_3$; —$(CH_2)_{0-4}N(R^\circ)_2$; —$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)SR^\circ$; —$(CH_2)_{0-4}C(O)OSiR^\circ_3$; —$(CH_2)_{0-4}OC(O)R^\circ$; —$(CH_2)_{0-4}SC(O)R^\circ$; —$(CH_2)_{0-4}C(O)NR^\circ_2$; —$C(S)NR^\circ_2$; —$(CH_2)_{0-4}OC(O)NR^\circ_2$; —$C(O)N(OR^\circ)R^\circ$; —$C(O)C(O)R^\circ$; —$C(O)CH_2C(O)R^\circ$; —$C(NOR^\circ)R^\circ$; —$(CH_2)_{0-4}S\ SR^\circ$; —$(CH_2)_{0-4}S(O)_2R^\circ$; —$(CH_2)_{0-4}S(O)_2OR^\circ$; —$(CH_2)_{0-4}OS(O)_2R^\circ$; —$S(O)_2NR^\circ_2$; —$(CH_2)_{0-4}S(O)R^\circ$; —$N(R^\circ)S(O)_2NR^\circ_2$; —$N(R^\circ)S(O)_2R^\circ$; —$N(OR^\circ)R^\circ$; —$C(NH)NR^\circ_2$; —$P(O)_2R^\circ$; —$P(O)R^\circ_2$; —$OP(O)R^\circ_2$; $SiR^\circ_3$; wherein each independent occurrence of $R^\circ$ is as defined herein supra. In other embodiments, the $R^{2a}$ group of formula I is —$NHR^4$ wherein $R^4$ is phenyl substituted with one or more optionally substituted $C_{1-6}$ aliphatic groups. In still other embodiments, $R^4$ is phenyl substituted with vinyl, allyl, acetylenyl, —$CH_2N_3$, —$CH_2CH_2N_3$, —$CH_2C\equiv CCH_3$, or —$CH_2C\equiv CH$.

In certain embodiments, the $R^{2a}$ group of formula V is —NHR$^4$ wherein R$^4$ is phenyl substituted with N$_3$, N(R$^o$)$_2$, CO$_2$R$^o$, or C(O)R$^o$ wherein each R$^o$ is independently as defined herein supra.

In certain embodiments, the $R^{2a}$ group of formula V is —N(R$^4$)$_2$ wherein each R$^4$ is independently an optionally substituted group selected from aliphatic, phenyl, naphthyl, a 5-6 membered aryl ring having 1-4 heteroatoms independently selected from nitrogen, oxygen, or sulfur, or a 8-10 membered bicyclic aryl ring having 1-5 heteroatoms independently selected from nitrogen, oxygen, or sulfur, or a detectable moiety.

In other embodiments, the $R^{2a}$ group of formula V is —N(R$^4$)$_2$ wherein the two R$^4$ groups are taken together with said nitrogen atom to form an optionally substituted 4-7 membered saturated, partially unsaturated, or aryl ring having 1-4 heteroatoms independently selected from nitrogen, oxygen, or sulfur. According to another embodiment, the two R$^4$ groups are taken together to form a 5-6-membered saturated or partially unsaturated ring having one nitrogen wherein said ring is substituted with one or two oxo groups. Such $R^{2a}$ groups include, but are not limited to, phthalimide, maleimide and succinimide.

In certain embodiments, the $R^{2a}$ group of formula V is a mono-protected or di-protected amino group. In certain embodiments $R^{2a}$ is a mono-protected amine. In certain embodiments $R^{2a}$ is a mono-protected amine selected from aralkylamines, carbamates, allyl amines, or amides. Exemplary mono-protected amino moieties include t-butyloxycarbonylamino, ethyloxycarbonylamino, methyloxycarbonylamino, trichloroethyloxy-carbonylamino, allyloxycarbonylamino, benzyloxocarbonylamino, allylamino, benzylamino, fluorenylmethylcarbonyl, formamido, acetamido, chloroacetamido, dichloroacetamido, trichloroacetamido, phenylacetamido, trifluoroacetamido, benzamido, and t-butyldiphenylsilylamino. In other embodiments $R^{2a}$ is a di-protected amine. Exemplary di-protected amino moieties include di-benzylamino, di-allylamino, phthalimide, maleimido, succinimido, pyrrolo, 2,2,5,5-tetramethyl-[1,2,5]azadisilolidino, and azido. In certain embodiments, the $R^{2a}$ moiety is phthalimido. In other embodiments, the $R^{2a}$ moiety is mono- or di-benzylamino or mono- or di-allylamino.

As defined generally above, the T group of formula V is a targeting group moiety. Targeting groups are well known in the art and include those described in International application publication number WO 2008/134731, published Nov. 6, 2008, the entirety of which is hereby incorporated by reference. In some embodiments, the T targeting group is a moiety selected from folate, a Her-2 binding peptide, a urokinase-type plasminogen activator receptor (uPAR) antagonist, a CXCR4 chemokine receptor antagonist, a GRP78 peptide antagonist, an RGD peptide, an RGD cyclic peptide, a luteinizing hormone-releasing hormone (LHRH) antagonist peptide, an aminopeptidase targeting peptide, a brain homing peptide, a kidney homing peptide, a heart homing peptide, a gut homing peptide, an integrin homing peptide, an angiogencid tumor endothelium homing peptide, an ovary homing peptide, a uterus homing peptide, a sperm homing peptide, a microglia homing peptide, a synovium homing peptide, a urothelium homing peptide, a prostate homing peptide, a lung homing peptide, a skin homing peptide, a retina homing peptide, a pancreas homing peptide, a liver homing peptide, a lymph node homing peptide, an adrenal gland homing peptide, a thyroid homing peptide, a bladder homing peptide, a breast homing peptide, a neuroblastoma homing peptide, a lymphona homing peptide, a muscle homing peptide, a wound vasculature homing peptide, an adipose tissue homing peptide, a virus binding peptide, or a fusogenic peptide. Such targeting groups are well known in the art and are described in detail in WO 2008/134731.

In some embodiments, the T targeting group is a moiety selected from a tumor homing group, a prostate specific membrane antigen homing peptide, an aminopeptidate N homing peptide, a Her-2 homing peptide, a colon cancer homing peptide, a VEGFR1 homing peptide, or a CXCR4 homing peptide.

In certain embodiments, the present invention provides a micelle, having an anthracycline encapsulated therein, comprising a multiblock copolymer of formula V, as defined above and described herein.

In some embodiments, the present invention provides a micelle, having an anthracycline encapsulated therein, comprising a multiblock copolymer of formula I and a multiblock copolymer of formula V, wherein each of formula I and formula V are as defined above and described herein, wherein the ratio of Formula I to Formula V is between about 1000:1 and about 1:1. In other embodiments, the ratio is about 1000:1, about 100:1, about 50:1, about 33:1, about 25:1, about 20:1, about 10:1, about 5:1, or about 4:1. In yet other embodiments, the ratio is between about 100:1 and about 25:1.

In certain embodiments, the present invention provides a micelle, having an anthracycline encapsulated therein, comprising a multiblock copolymer of formula VI:

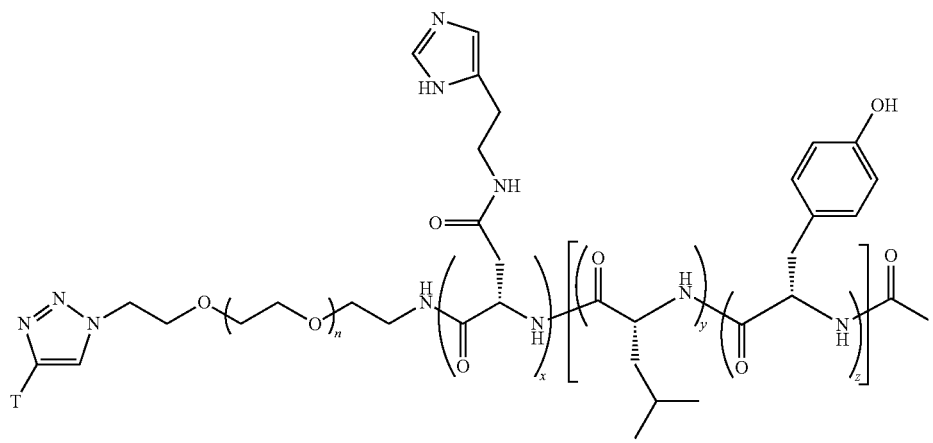

VI wherein:
T is a targeting group moiety;
n is 110 to 450;
x is 3 to 50;
y is 5 to 50;
z is 5 to 50.

As defined generally above, the n group of formula VI is 110-450. In certain embodiments, the present invention provides compounds of formula VI, as described above, wherein n is about 225. In other embodiments, n is about 270. In other embodiments, n is about 350. In other embodiments, n is about 110. In other embodiments, n is about 450. In other embodiments, n is selected from 110±10, 180±10, 225±10, 275±10, 315±10, or 450±10.

In certain embodiments, the x group of formula VI is about 3 to about 50. In certain embodiments, the x group of formula VI is about 10. In other embodiments, x is about 20. According to yet another embodiment, x is about 15. In other embodiments, x is about 5. In other embodiments, x is selected from 5±3, 10±3, 10±5, 15±5, or 20±5.

In certain embodiments, the y group of formula VI is about 5 to about 50. In certain embodiments, the y group of formula VI is about 10. In other embodiments, y is about 20. According to yet another embodiment, y is about 15. In other embodiments, y is about 30. In other embodiments, y is selected from 10±3, 15±3, 17±3, 20±5, or 30±5.

In certain embodiments, the z group of formula VI is about 5 to about 50. In certain embodiments, the z group of formula VI is about 10. In other embodiments, z is about 20. According to yet another embodiment, z is about 15. In other embodiments, z is about 30. In other embodiments, z is selected from 10±3, 15±3, 17±3, 20±5, or 30±5.

In some embodiments, the T targeting group moiety of formula VI is a moiety selected from folate, a Her-2 binding peptide, a urokinase-type plasminogen activator receptor (uPAR) antagonist, a CXCR4 chemokine receptor antagonist, a GRP78 peptide antagonist, an RGD peptide, an RGD cyclic peptide, a luteinizing hormone-releasing hormone (LHRH) antagonist peptide, an aminopeptidase targeting peptide, a brain homing peptide, a kidney homing peptide, a heart homing peptide, a gut homing peptide, an integrin homing peptide, an angiogencid tumor endothelium homing peptide, an ovary homing peptide, a uterus homing peptide, a sperm homing peptide, a microglia homing peptide, a synovium homing peptide, a urothelium homing peptide, a prostate homing peptide, a lung homing peptide, a skin homing peptide, a retina homing peptide, a pancreas homing peptide, a liver homing peptide, a lymph node homing peptide, an adrenal gland homing peptide, a thyroid homing peptide, a bladder homing peptide, a breast homing peptide, a neuroblastoma homing peptide, a lymphona homing peptide, a muscle homing peptide, a wound vasculature homing peptide, an adipose tissue homing peptide, a virus binding peptide, or a fusogenic peptide. Such targeting groups are well known in the art and are described in detail in WO 2008/134731.

In some embodiments, the T targeting group is a moiety selected from a tumor homing group, a prostate specific membrane antigen homing peptide, an aminopeptidate N homing peptide, a Her-2 homing peptide, a breast cancer homing peptide, a VEGFR1 homing peptide, or a CXCR4 homing peptide.

In certain embodiments, the present invention provides a micelle, having an anthracycline encapsulated therein, comprising a multiblock copolymer of formula VI, as defined above and described herein.

In certain embodiments, the present invention provides a micelle, having an anthracycline encapsulated therein, comprising a multiblock copolymer of formula VII:

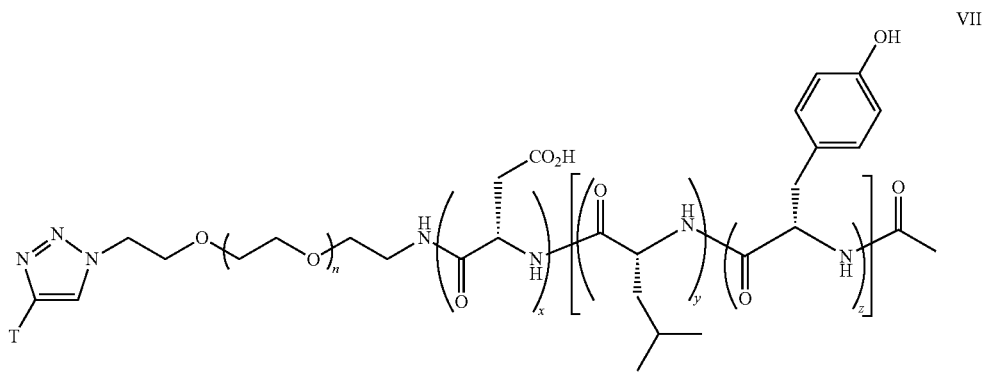

wherein:
T is a targeting group moiety;
n is 110 to 450;
m is 1 or 2;
x is 3 to 50;
y is 5 to 50; and
z is 5 to 50.

As defined generally above, the n group of formula VII is 110-450. In certain embodiments, the present invention provides compounds of formula VII, as described above, wherein n is about 225. In other embodiments, n is about 270. In other embodiments, n is about 350. In other embodiments, n is about 110. In other embodiments, n is about 450. In other embodiments, n is selected from 110±10, 180±10, 225±10, 275±10, 315±10, or 450±10.

As defined generally above, the m group of formula VII is 1 or 2. In some embodiments, m is 1 thereby forming a poly(aspartic acid) block. In some embodiments, m is 2 thereby forming a poly(glutamic acid) block.

In certain embodiments, the x group of formula VII is about 3 to about 50. In certain embodiments, the x group of formula VII is about 10. In other embodiments, x is about 20. According to yet another embodiment, x is about 15. In other embodiments, x is about 5. In other embodiments, x is selected from 5±3, 10±3, 10±5, 15±5, or 20±5.

In certain embodiments, the y group of formula VII is about 5 to about 50. In certain embodiments, the y group of formula VII is about 10. In other embodiments, y is about 20. According to yet another embodiment, y is about 15. In other embodiments, y is about 30. In other embodiments, y is selected from 10±3, 15±3, 17±3, 20±5, or 30±5.

In certain embodiments, the z group of formula VII is about 5 to about 50. In certain embodiments, the z group of formula VII is about 10. In other embodiments, z is about 20. According to yet another embodiment, z is about 15. In other embodiments, z is about 30. In other embodiments, z is selected from 10±3, 15±3, 17±3, 20±5, or 30±5.

In certain embodiments, the present invention provides a multiblock copolymer of formula VII wherein n is about 270, x is about 10, y is about 20, and z is about 20.

In some embodiments, the T targeting group moiety of formula VII is a moiety selected from folate, a Her-2 binding peptide, a urokinase-type plasminogen activator receptor (uPAR) antagonist, a CXCR4 chemokine receptor antagonist, a GRP78 peptide antagonist, an RGD peptide, an RGD cyclic peptide, a luteinizing hormone-releasing hormone (LHRH) antagonist peptide, an aminopeptidase targeting peptide, a brain homing peptide, a kidney homing peptide, a heart homing peptide, a gut homing peptide, an integrin homing peptide, an angiogencid tumor endothelium homing peptide, an ovary homing peptide, a uterus homing peptide, a sperm homing peptide, a microglia homing peptide, a synovium homing peptide, a urothelium homing peptide, a prostate homing peptide, a lung homing peptide, a skin homing peptide, a retina homing peptide, a pancreas homing peptide, a liver homing peptide, a lymph node homing peptide, an adrenal gland homing peptide, a thyroid homing peptide, a bladder homing peptide, a breast homing peptide, a neuroblastoma homing peptide, a lymphona homing peptide, a muscle homing peptide, a wound vasculature homing peptide, an adipose tissue homing peptide, a virus binding peptide, or a fusogenic peptide. Such targeting groups are well known in the art and are described in detail in WO 2008/134731.

In some embodiments, the T targeting group is a moiety selected from a tumor homing group, a prostate specific membrane antigen homing peptide, an aminopeptidate N homing peptide, a Her-2 homing peptide, a breast cancer homing peptide, a VEGFR1 homing peptide, or a CXCR4 homing peptide.

In certain embodiments, the present invention provides a micelle, having an anthracycline encapsulated therein, comprising a multiblock copolymer of formula VII, as defined above and described herein.

In some embodiments, the present invention provides a micelle, having an anthracycline encapsulated therein, comprising a multiblock copolymer of formula I and a multiblock copolymer of formula VII, wherein each of formula I and formula VII are as defined above and described herein, wherein the ratio of Formula I to Formula VII is between about 1000:1 and about 1:1. In other embodiments, the ratio is about 1000:1, about 100:1, about 50:1, about 33:1, about 25:1, about 20:1, about 10:1, about 5:1, or about 4:1. In yet other embodiments, the ratio is between about 100:1 and about 25:1.

In another embodiment, the present invention provides a micelle, having an anthracycline encapsulated therein, comprising a multiblock copolymer of formula I, and two or more multiblock copolymers selected from any of formula II, formula III, formula V, formula VI, or formula VII.

In certain embodiments, the present invention provides a micelle, having an anthracycline encapsulated therein, comprising a multiblock copolymer of formula VIII:

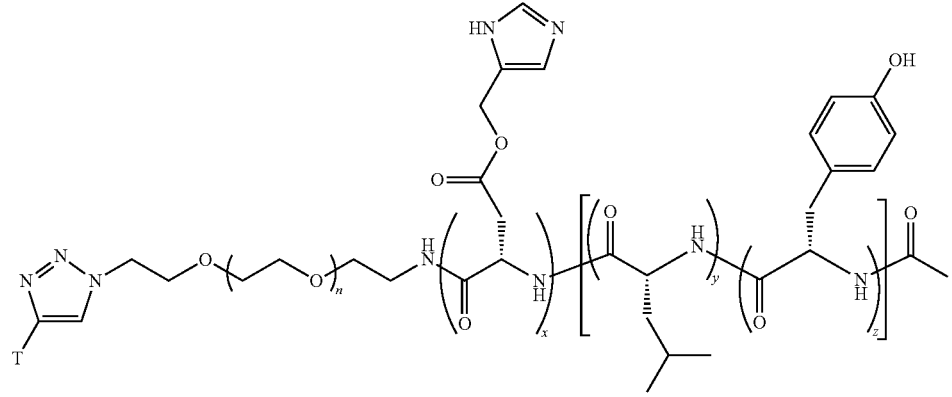

VIII wherein:

T is a targeting group moeity;

n is 110 to 450;

x is 3 to 50;

y is 5 to 50;

z is 5 to 50.

As defined generally above, the n group of formula VIII is 110-450. In certain embodiments, the present invention provides compounds of formula VIII, as described above, wherein n is about 225. In other embodiments, n is about 270. In other embodiments, n is about 350. In other embodiments, n is about 110. In other embodiments, n is about 450. In other embodiments, n is selected from 110±10, 180±10, 225±10, 275±10, 315±10, or 450±10.

In certain embodiments, the x group of formula VIII is about 3 to about 50. In certain embodiments, the x group of formula VIII is about 10. In other embodiments, x is about 20. According to yet another embodiment, x is about 15. In other embodiments, x is about 5. In other embodiments, x is selected from 5±3, 10±3, 10±5, 15±5, or 20±5.

In certain embodiments, the y group of formula VIII is about 5 to about 50. In certain embodiments, the y group of formula VIII is about 10. In other embodiments, y is about 20. According to yet another embodiment, y is about 15. In other embodiments, y is about 30. In other embodiments, y is selected from 10±3, 15±3, 17±3, 20±5, or 30±5.

In certain embodiments, the z group of formula VIII is about 5 to about 50. In certain embodiments, the z group of formula VIII is about 10. In other embodiments, z is about 20. According to yet another embodiment, z is about 15. In other embodiments, z is about 30. In other embodiments, z is selected from 10±3, 15±3, 17±3, 20±5, or 30±5.

In some embodiments, the T targeting group moiety of formula VIII is a moiety selected from folate, a Her-2 binding peptide, a urokinase-type plasminogen activator receptor (uPAR) antagonist, a CXCR4 chemokine receptor antagonist, a GRP78 peptide antagonist, an RGD peptide, an RGD cyclic peptide, a luteinizing hormone-releasing hormone (LHRH) antagonist peptide, an aminopeptidase targeting peptide, a brain homing peptide, a kidney homing peptide, a heart homing peptide, a gut homing peptide, an integrin homing peptide, an angiogencid tumor endothelium homing peptide, an ovary homing peptide, a uterus homing peptide, a sperm homing peptide, a microglia homing peptide, a synovium homing peptide, a urothelium homing peptide, a prostate homing peptide, a lung homing peptide, a skin homing peptide, a retina homing peptide, a pancreas homing peptide, a liver homing peptide, a lymph node homing peptide, an adrenal gland homing peptide, a thyroid homing peptide, a bladder homing peptide, a breast homing peptide, a neuroblastoma homing peptide, a lymphona homing peptide, a muscle homing peptide, a wound vasculature homing peptide, an adipose tissue homing peptide, a virus binding peptide, or a fusogenic peptide. Such targeting groups are well known in the art and are described in detail in WO 2008/134731.

In some embodiments, the T targeting group is a moiety selected from a tumor homing group, a prostate specific membrane antigen homing peptide, an aminopeptidate N homing peptide, a Her-2 homing peptide, a breast cancer homing peptide, a VEGFR1 homing peptide, or a CXCR4 homing peptide.

In certain embodiments, the present invention provides a micelle, having an anthracycline encapsulated therein, comprising a multiblock copolymer of formula VIII, as defined above and described herein.

In certain embodiments, the present invention provides an anthracycline loaded micelle comprising a multiblock copolymer, wherein said micelle has a drug-loaded inner core, a crosslinked outer core, and a hydrophilic shell, wherein the multiblock copolymer is of formula IX:

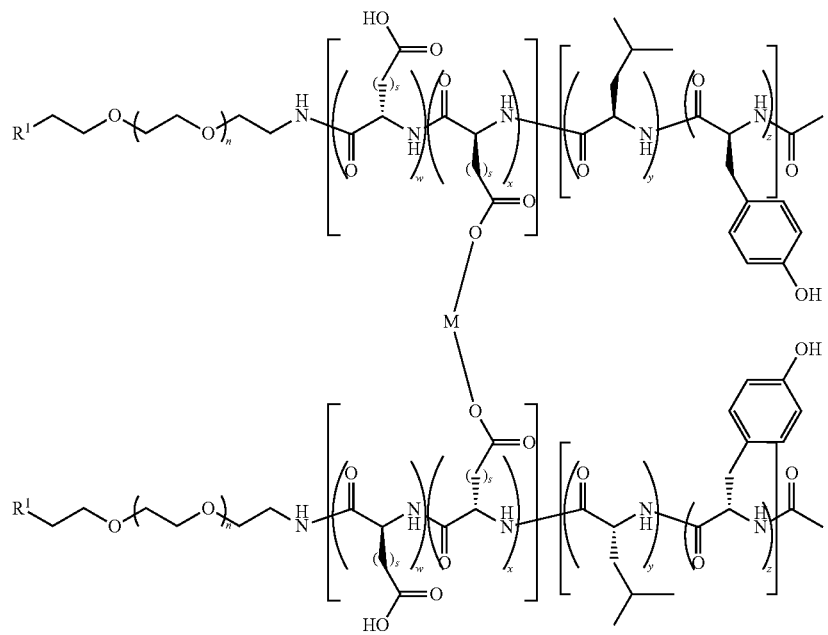

wherein:
each n is independently 10-2500;
each s is independently 1 or 2
each w is independently 0-30;
each x is independently 1-30;
each y is independently 5-50;
each z is independently 5-50;
M is Zn, Fe, Co, or Ni; and
each $R^1$ is independently —$N_3$—$OCH_3$ or

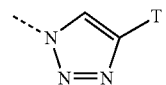

wherein T is a targeting group moiety.

As defined generally above, each n group of formula IX is independently 110-450. In certain embodiments, the present invention provides compounds of formula IX, as described above, wherein n is about 225. In other embodiments, n is about 270. In other embodiments, n is about 350. In other embodiments, n is about 110. In other embodiments, n is about 450. In other embodiments, n is selected from 110±10, 180±10, 225±10, 275±10, 315±10, or 450±10.

In certain embodiments, each w group of formula IX is independently about 0 to about 30. In certain embodiments, the w group of formula IX is about 10. In other embodiments, w is about 20. In some embodiments, w is 0. In yet other embodiments, w is a range from 0 to 10. According to yet another embodiment, w is about 15. In other embodiments, w is about 5. In other embodiments, w is selected from 5±3, 10±3, 10±5, 15±5, or 20±5.

In certain embodiments, each x group of formula IX is independently about 1 to about 30. In certain embodiments, the x group of formula IX is about 10. In other embodiments, x is about 20. According to yet another embodiment, x is about 15. In other embodiments, x is about 5. In other embodiments, x is selected from 3±2, 5±3, 10±3, 10±5, 15±5, or 20±5.

In certain embodiments, each y group of formula IX is independently about 5 to about 50. In certain embodiments, the y group of formula IX is about 10. In other embodiments, y is about 20. According to yet another embodiment, y is about 15. In other embodiments, y is about 30. In other embodiments, y is selected from 10±3, 15±3, 17±3, 20±5, or 30±5.

In certain embodiments, each z group of formula IX is independently about 5 to about 50. In certain embodiments, the z group of formula IX is about 10. In other embodiments, z is about 20. According to yet another embodiment, z is about 15. In other embodiments, z is about 30. In other embodiments, z is selected from 10±3, 15±3, 17±3, 20±5, or 30±5.

In some embodiments, each T targeting group moiety of formula IX is independently a moiety selected from folate, a Her-2 binding peptide, a urokinase-type plasminogen activator receptor (uPAR) antagonist, a CXCR4 chemokine receptor antagonist, a GRP78 peptide antagonist, an RGD peptide, an RGD cyclic peptide, a luteinizing hormone-releasing hormone (LHRH) antagonist peptide, an aminopeptidase targeting peptide, a brain homing peptide, a kidney homing peptide, a heart homing peptide, a gut homing peptide, an integrin homing peptide, an angiogencid tumor endothelium homing peptide, an ovary homing peptide, a uterus homing peptide, a sperm homing peptide, a microglia homing peptide, a synovium homing peptide, a urothelium homing peptide, a prostate homing peptide, a lung homing peptide, a skin homing peptide, a retina homing peptide, a pancreas homing peptide, a liver homing peptide, a lymph node homing peptide, an adrenal gland homing peptide, a thyroid homing peptide, a bladder homing peptide, a breast homing peptide, a neuroblastoma homing peptide, a lymphona homing peptide, a muscle homing peptide, a wound vasculature homing peptide, an adipose tissue homing peptide, a virus binding peptide, or a fusogenic peptide. Such targeting groups are well known in the art and are described in detail in WO 2008/134731.

In some embodiments, the T targeting group is a moiety selected from a tumor homing group, a prostate specific membrane antigen homing peptide, an aminopeptidate N homing peptide, a Her-2 homing peptide, a breast cancer homing peptide, a VEGFR1 homing peptide, or a CXCR4 homing peptide.

In certain embodiments, the present invention provides a micelle, having an anthracycline encapsulated therein, comprising a multiblock copolymer of formula VIII, as defined above and described herein.

In certain embodiments, the present invention provides an anthracycline loaded micelle comprising a multiblock copolymer, wherein said micelle has a drug-loaded inner core, a crosslinked outer core, and a hydrophilic shell, wherein the multiblock copolymer is of formula X:

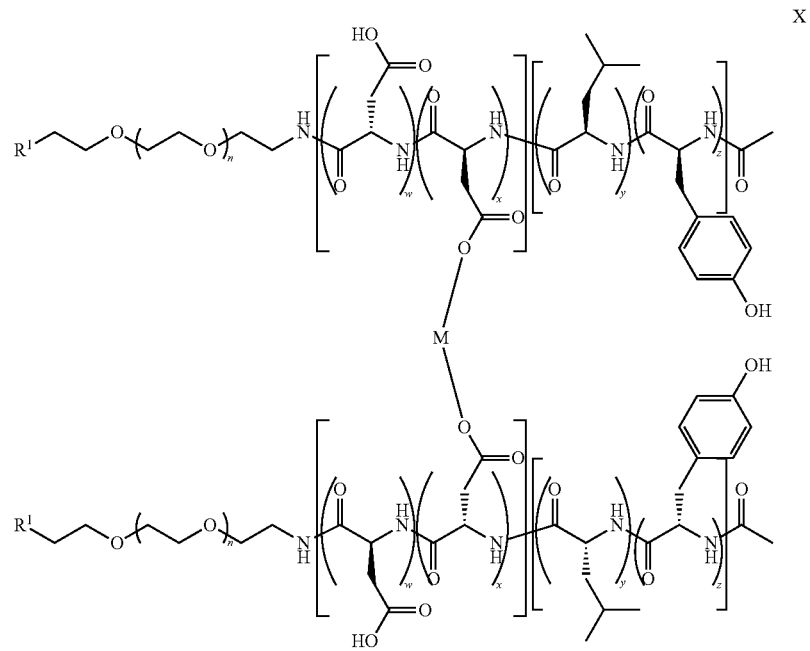

wherein:

each n is independently 110 to 450;

each w is independently 0-20;

each x is independently 1-20;

each y is independently 5 to 50;

each z is independently 5 to 50.

M is Zn, Fe, Co, or Ni; and each $R^1$ is independently —$N_3$—$OCH_3$ or

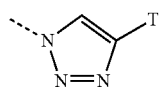

wherein T is a targeting group moiety.

As defined generally above, each n group of formula X is independently 110-450. In certain embodiments, the present invention provides compounds of formula X, as described above, wherein n is about 225. In other embodiments, n is about 270. In other embodiments, n is about 350. In other embodiments, n is about 110. In other embodiments, n is about 450. In other embodiments, n is selected from 110±10, 180±10, 225±10, 275±10, 315±10, or 450±10.

In certain embodiments, each w group of formula X is independently about 0 to about 30. In certain embodiments, the w group of formula X is about 10. In other embodiments, w is about 20. In some embodiments, w is 0. In yet other embodiments, w is a range from 0 to 10. According to yet another embodiment, w is about 15. In other embodiments, w is about 5. In other embodiments, w is selected from 5±3, 10±3, 10±5, 15±5, or 20±5.

In certain embodiments, each x group of formula X is independently about 1 to about 30. In certain embodiments, the x group of formula X is about 10. In other embodiments, x is about 20. According to yet another embodiment, x is about 15. In other embodiments, x is about 5. In other embodiments, x is selected from 3±2, 5±3, 10±3, 10±5, 15±5, or 20±5.

In certain embodiments, each y group of formula X is independently about 5 to about 50. In certain embodiments, the y group of formula X is about 10. In other embodiments, y is about 20. According to yet another embodiment, y is about 15. In other embodiments, y is about 30. In other embodiments, y is selected from 10±3, 15±3, 17±3, 20±5, or 30±5.

In certain embodiments, each z group of formula X is independently about 5 to about 50. In certain embodiments, the z group of formula X is about 10. In other embodiments, z is about 20. According to yet another embodiment, z is about 15. In other embodiments, z is about 30. In other embodiments, z is selected from 10±3, 15±3, 17±3, 20±5, or 30±5.

In some embodiments, each T targeting group moiety of formula X is independently a moiety selected from folate, a Her-2 binding peptide, a urokinase-type plasminogen activator receptor (uPAR) antagonist, a CXCR4 chemokine receptor antagonist, a GRP78 peptide antagonist, an RGD peptide, an RGD cyclic peptide, a luteinizing hormone-releasing hormone (LHRH) antagonist peptide, an aminopeptidase targeting peptide, a brain homing peptide, a kidney homing peptide, a heart homing peptide, a gut homing peptide, an integrin homing peptide, an angiogencid tumor endothelium homing peptide, an ovary homing peptide, a uterus homing peptide, a sperm homing peptide, a microglia homing peptide, a synovium homing peptide, a urothelium homing peptide, a prostate homing peptide, a lung homing peptide, a skin homing peptide, a retina homing peptide, a pancreas homing peptide, a liver homing peptide, a lymph node homing peptide, an adrenal gland homing peptide, a thyroid homing peptide, a bladder homing peptide, a breast homing peptide, a neuroblastoma homing peptide, a lymphona homing peptide, a muscle homing peptide, a wound vasculature homing peptide, an adipose tissue homing peptide, a virus binding peptide, or a fusogenic peptide. Such targeting groups are well known in the art and are described in detail in WO 2008/134731.

In some embodiments, the T targeting group is a moiety selected from a tumor homing group, a prostate specific membrane antigen homing peptide, an aminopeptidate N homing peptide, a Her-2 homing peptide, a breast cancer homing peptide, a VEGFR1 homing peptide, or a CXCR4 homing peptide.

In certain embodiments, the present invention provides a micelle, having an anthracycline encapsulated therein, comprising a multiblock copolymer of formula XI:

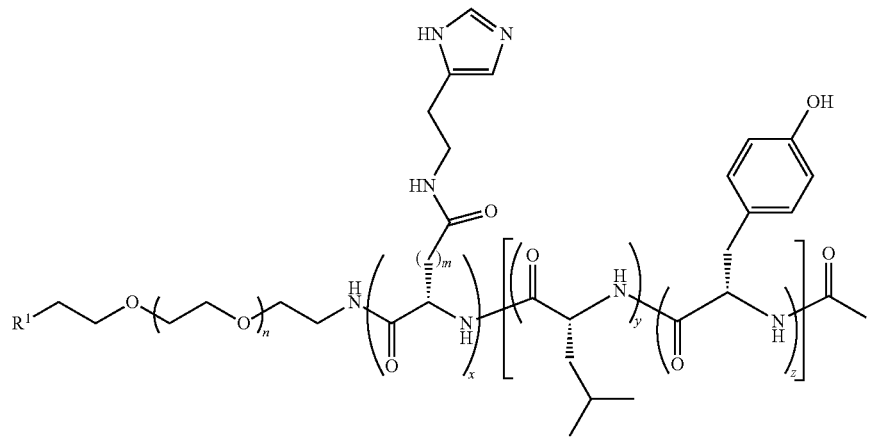

wherein:
$R^1$ is —$OCH_3$, —$N_3$, or

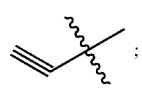

m is 1 or 2
n is 110 to 450;
x is 3 to 50;
y is 5 to 50;
z is 5 to 50.

As defined generally above, the n group of formula XI is 110-450. In certain embodiments, the present invention provides compounds of formula XI, as described above, wherein n is about 225. In other embodiments, n is about 270. In other embodiments, n is about 350. In other embodiments, n is about 110. In other embodiments, n is about 450. In other embodiments, n is selected from 110±10, 180±10, 225±10, 275±10, 315±10, or 450±10.

In certain embodiments, the x group of formula XI is about 3 to about 50. In certain embodiments, the x group of formula XI is about 10. In other embodiments, x is about 20. According to yet another embodiment, x is about 15. In other embodiments, x is about 5. In other embodiments, x is selected from 5±3, 10±3, 10±5, 15±5, or 20±5.

In certain embodiments, the y group of formula XI is about 5 to about 50. In certain embodiments, the y group of formula XI is about 10. In other embodiments, y is about 20. According to yet another embodiment, y is about 15. In other embodiments, y is about 30. In other embodiments, y is selected from 10±3, 15±3, 17±3, 20±5, or 30±5.

In certain embodiments, the z group of formula XI is about 5 to about 50. In certain embodiments, the z group of formula XI is about 10. In other embodiments, z is about 20. According to yet another embodiment, z is about 15. In other embodiments, z is about 30. In other embodiments, z is selected from 10±3, 15±3, 17±3, 20±5, or 30±5.

In some embodiments, the present invention provides a micelle, having an anthracycline encapsulated therein, comprising a multiblock copolymer of formula XI and a multiblock copolymer of formula VI, wherein each of formula XI and formula VI are as defined above and described herein, wherein the ratio of Formula XI to Formula VI is between about 1000:1 and about 1:1. In other embodiments, the ratio is about 1000:1, about 100:1, about 50:1, about 33:1, about 25:1, about 20:1, about 10:1, about 5:1, or about 4:1. In yet other embodiments, the ratio is between about 100:1 and about 25:1.

In certain embodiments, the present invention provides an anthracycline loaded micelle comprising a multiblock copolymer, wherein said micelle has a drug-loaded inner core, a crosslinked outer core, and a hydrophilic shell, wherein the multiblock copolymer is of formula XII:

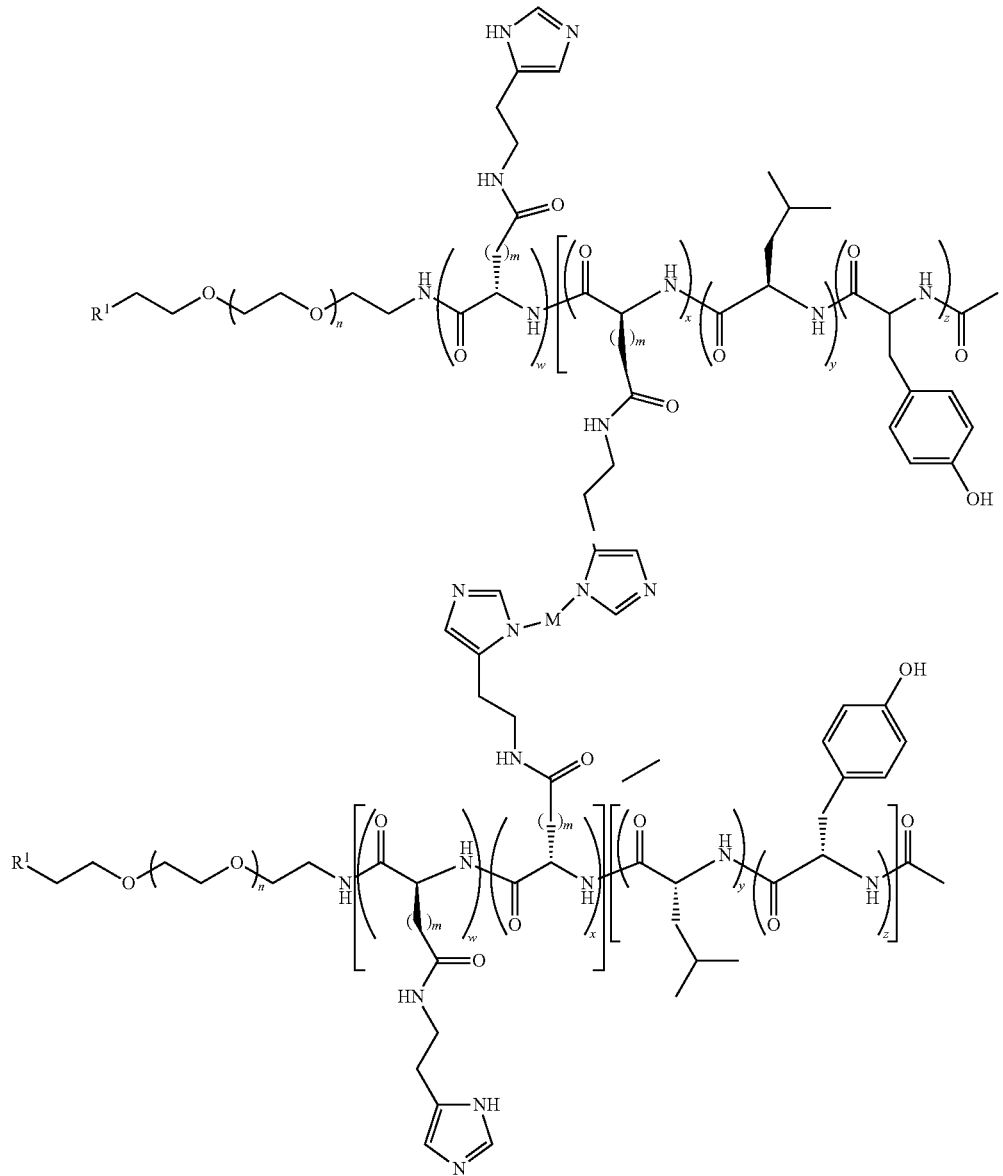

XII wherein:
each n is independently 110 to 450;
each m is independently 1 or 2;
each w is independently 0-20;
each x is independently 1-20;
each y is independently 5 to 50;
each z is independently 5 to 50.
M is Zn, Fe, Co, or Ni; and
each $R^1$ is independently —$N_3$, —$OCH_3$ or

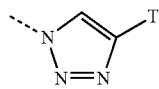

wherein T is a targeting group moiety.

As defined generally above, each n group of formula XII is independently 110-450. In certain embodiments, the present invention provides compounds of formula XII, as described above, wherein n is about 225. In other embodiments, n is about 270. In other embodiments, n is about 350. In other embodiments, n is about 110. In other embodiments, n is about 450. In other embodiments, n is selected from 110±10, 180±10, 225±10, 275±10, 315±10, or 450±10.

In certain embodiments, each x group of formula XII is independently about 1 to about 30. In certain embodiments, the x group of formula X is about 10. In other embodiments, x is about 20. According to yet another embodiment, x is about 15. In other embodiments, x is about 5. In other embodiments, x is selected from 3±2, 5±3, 10±3, 10±5, 15±5, or 20±5.

In certain embodiments, each y group of formula XII is independently about 5 to about 50. In certain embodiments, the y group of formula XII is about 10. In other embodiments, y is about 20. According to yet another embodiment, y is about 15. In other embodiments, y is about 30. In other embodiments, y is selected from 10±3, 15±3, 17±3, 20±5, or 30±5.

In certain embodiments, each z group of formula XII is independently about 5 to about 50. In certain embodiments, the z group of formula XII is about 10. In other embodiments, z is about 20. According to yet another embodiment, z is about 15. In other embodiments, z is about 30. In other embodiments, z is selected from 10±3, 15±3, 17±3, 20±5, or 30±5.

In some embodiments, each T targeting group moiety of formula XII is independently a moiety selected from folate, a Her-2 binding peptide, a urokinase-type plasminogen activator receptor (uPAR) antagonist, a CXCR4 chemokine receptor antagonist, a GRP78 peptide antagonist, an RGD peptide, an RGD cyclic peptide, a luteinizing hormone-releasing hormone (LHRH) antagonist peptide, an aminopeptidase targeting peptide, a brain homing peptide, a kidney homing peptide, a heart homing peptide, a gut homing peptide, an integrin homing peptide, an angiogencid tumor endothelium homing peptide, an ovary homing peptide, a uterus homing peptide, a sperm homing peptide, a microglia homing peptide, a synovium homing peptide, a urothelium homing peptide, a prostate homing peptide, a lung homing peptide, a skin homing peptide, a retina homing peptide, a pancreas homing peptide, a liver homing peptide, a lymph node homing peptide, an adrenal gland homing peptide, a thyroid homing peptide, a bladder homing peptide, a breast homing peptide, a neuroblastoma homing peptide, a lymphona homing peptide, a muscle homing peptide, a wound vasculature homing peptide, an adipose tissue homing peptide, a virus binding peptide, or a fusogenic peptide. Such targeting groups are well known in the art and are described in detail in WO 2008/134731.

In some embodiments, the T targeting group is a moiety selected from a tumor homing group, a prostate specific membrane antigen homing peptide, an aminopeptidate N homing peptide, a Her-2 homing peptide, a breast cancer homing peptide, a VEGFR1 homing peptide, or a CXCR4 homing peptide.

4. General Methods for Providing Compounds of the Present Invention

Bifunctional PEG's are prepared according to U.S. Patent Application Publication Numbers 2006/0240092, 2006/0172914, 2006/0142506, and 2008/0035243, and Published PCT Applications WO07/127,473, WO07/127,440, and WO06/86325, the entirety of each of which is hereby incorporated by reference.

Multiblock copolymers of the present invention are prepared by methods known to one of ordinary skill in the art and those described in detail in U.S. patent application Ser. No. 11/325,020 filed Jan. 4, 2006 and published as US 20060172914 on Aug. 3, 2006, the entirety of which is hereby incorporated herein by reference. Generally, such multiblock copolymers are prepared by sequentially polymerizing one or more cyclic amino acid monomers onto a hydrophilic polymer having a terminal amine salt wherein said polymerization is initiated by said amine salt. In certain embodiments, said polymerization occurs by ring-opening polymerization of the cyclic amino acid monomers. In other embodiments, the cyclic amino acid monomer is an amino acid NCA, lactam, or imide. Details of preparing exemplary multiblock copolymers of the present invention are set forth in the Exemplification, infra.

Methods of preparing micelles are known to one of ordinary skill in the art. Micelles can be prepared by a number of different dissolution methods. In the direct dissolution method, the block copolymer is added directly to an aqueous medium with or without heating and micelles are spontaneously formed up dissolution. The dialysis method is often used when micelles are formed from poorly aqueous soluble copolymers. The copolymer is dissolved in a water miscible organic solvent such as N-methylpyrollidinone, dimethylformamide, dimethylsulfoxide, tetrahydrofuran, or dimethylacetamide, and this solution is then dialyzed against water or another aqueous medium. During dialysis, micelle formation is induced and the organic solvent is removed. Alternatively, the block copolymer can be dissolved in a water miscible organic solvent such as N-methylpyrollidinone, dimethylformamide, dimethylsulfoxide, tetrahydrofuran, or dimethylacetamide and added dropwise to water or another aqueous medium. The micelles can then be isolated by filtration or lyophilization.

Emulsification methods can also be employed for micelle formation. For example, the block copolymer is dissolved in a water-immiscible, volatile solvent (e.g. dichloromethane) and added to water with vigorous agitation. As the solvent is removed by evaporation, micelles spontaneously form. Prepared micelles can then be filtered and isolated by lyophilization.

Micelles can be prepared by a number of different dissolution methods. In the direct dissolution method, the block copolymer is added directly to an aqueous medium, with or without heating, and micelles are spontaneously formed up dissolution. The dialysis method is often used when micelles are formed from poorly aqueous soluble copolymers. The copolymer is dissolved in a water miscible organic solvent such as N-methylpyrollidinone, dimethylformamide, dimethylsulfoxide, tetrahydrofuran, or dimethylacetamide, and this solution is then dialyzed against water or another aqueous medium. During dialysis, micelle formation is induced and the organic solvent is removed. Alternatively, the block copolymer can be dissolved in a water miscible organic solvent such as N-methylpyrollidinone, dimethylformamide, dimethylsulfoxide, tetrahydrofuran, or dimethylacetamide and added dropwise to water or another aqueous medium. The micelles can then be isolated by filtration or lyophilization.

Crosslinking Chemistries

In addition to advances in polymer micelle technology, significant efforts have been made in the development of stimuli-responsive polymeric materials that can respond to environmental pH changes. See Chatterjee, J.; Haik, Y.; Chen, C. J. *J. App. Polym. Sci.* 2004, 91, 3337-3341; Du, J. Z.; Armes, S. P. *J. Am. Chem. Soc.* 2005, 127, 12800-12801; and Twaites, B. R.; de las Heras Alarcon, C.; Cunliffe, D.; Lavigne, M.; Pennadam, S.; Smith, J. R.; Gorecki, D. C.; Alexander, C. *J. Control. Release* 2004, 97, 551-566. This is of importance for sensitive protein and nucleic acid-based drugs where escape from acidic intracellular compartments (i.e. endosome and lysosome) and cytoplasmic release are required to achieve therapeutic value. See Murthy, N.; Campbell, J.; Fausto, N.; Hoffman, A. S.; Stayton, P. S. *J. Control. Release* 2003, 89, 365-374; El-Sayed, M. E. H.; Hoffman, A. S.; Stayton, P. S. *J. Control. Release* 2005, 104, 417-427; and Liu, Y.; Wenning, L.; Lynch, M.; Reineke, T. *J. Am. Chem. Soc.* 2004, 126, 7422-7423. Acid-sensitive delivery systems that can successfully escape the endosome and transport small-molecule chemotherapeutic drugs into the cytoplasm are also of interest since these carriers can bypass many of the cellular mechanisms responsible for multi-drug resistance. In some of these cases, the polymers are designed to respond to the significant pH gradient between the blood (pH 7.4) and the late-early endosome (pH ~5.0-6.0).

In contrast to shell-crosslinked micelles, the crosslinking of multiblock copolymer micelles in accordance with the present invention is accomplished without large dilution volumes because micelle-micelle coupling does not occur. Such crosslinking will enhance post-administration circulation time leading to more efficient passive drug targeting by the EPR effect and improved active targeting using cancer-specific targeting groups. In addition, stimuli-responsive crosslinking may offer another targeting mechanism to isolate the release of the chemotherapy drug exclusively within the tumor tissue and cancer cell cytoplasm.

Crosslinking reactions designed for drug delivery preferably meet a certain set of requirements to be deemed safe and useful for in vivo applications. For example, in other embodiments, the crosslinking reaction would utilize non-cytotoxic reagents, would be insensitive to water, would not alter the drug to be delivered, and in the case of cancer therapy, would be reversible at pH levels commonly encountered in tumor tissue (pH ~6.8) or acidic organelles in cancer cells (pH ~5.0-6.0).

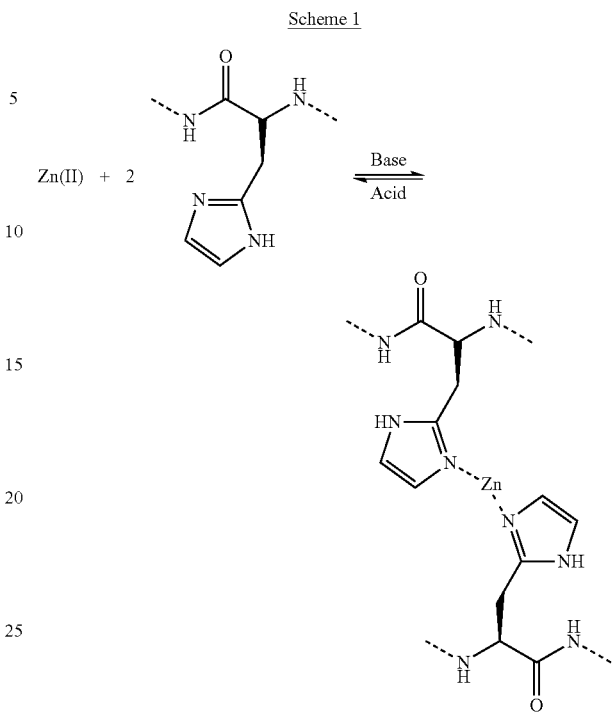

Scheme 1

Scheme 1 above illustrates the reaction of an aqueous zinc (II) ion (e.g. from zinc chloride or zinc acetate) with two equivalents of an appropriate imidazole (e.g. histidine) to form a zinc-histidine complex. This reaction occurs rapidly in a slightly basic pH environment and is reversible upon acidification to pH less than 6. (Tezcan, et. al. *J. Am. Chem. Soc.* 2007, 129, 13347-13375.)

In certain embodiments, the -M- moiety of formula II is zinc. In certain embodiments, the crosslinking utilizes zinc-mediated coupling of carboxylic acids, a highly selective and pH-sensitive reaction that is performed in water. This reaction, which is widely used in cough lozenge applications, involves the association of zinc ions with carboxylic acids at basic pH. See Bakar, N. K. A.; Taylor, D. M.; Williams, D. R. *Chem. Spec. Bioavail.* 1999, 11, 95-101; and Eby, G. A. *J. Antimicrob. Chemo.* 1997, 40, 483-493. These zinc-carboxylate bonds readily dissociate in the presence of acid.

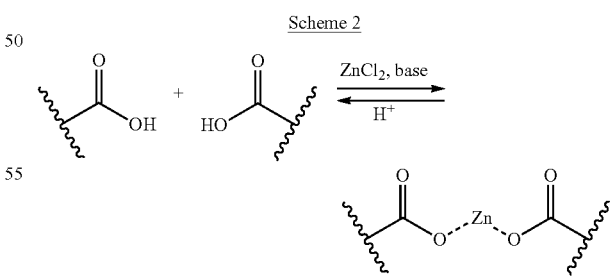

Scheme 2

Scheme 2 above illustrates the reaction of an aqueous zinc ion (e.g. from zinc chloride) with two equivalents of an appropriate carboxylic acid to form the zinc dicarboxylate. This reaction occurs rapidly and irreversibly in a slightly basic pH environment but upon acidification, is reversible within a tunable range of pH 2.0-6.8 to reform $ZnX_2$, where X is the conjugate base. One of ordinary skill in the art will recognize that a variety of natural and unnatural amino acid side-chains have a carboxylic acid moeity that can be crosslinked by zinc or another suitable metal.

The choice of zinc as a crosslinking metal is advantageous for effective micelle crosslinking Zinc chloride and the zinc lactate by-product are generally recognized as non-toxic, and other safety concerns are not anticipated. Pharmaceutical grade zinc chloride is commonly used in mouthwash and as a chlorophyll stabilizer in vegetables while zinc lactate is used as an additive in toothpaste and drug preparation. The reaction is reversible within a tunable pH range, selective toward carboxylic acids, and should not alter the encapsulated chemotherapy agents. While zinc has been chosen as an exemplary metal for micelle crosslinking, it should be noted that many other metals undergo acid sensitive coupling with carboxylic acids. These metals include calcium, iron and aluminum, to name but a few. One or more of these metals can be substituted for zinc.

In one embodiment, drug-loaded micelles possessing carboxylic acid functionality in the outer core are crosslinked by addition of zinc chloride to the micelle solution. Surprisingly, it was found that the efficiency of this reaction is greatly improved when performed in the presence of TRIS (tris(hydroxymethyl)aminomethane) buffer. In certain embodiments, drug-loaded micelles possessing carboxylic acid functionality in the outer core are crosslinked by dissolving the micelles in TRIS buffer solution containing zinc chloride. In yet other embodiments, drug-loaded micelles possessing carboxylic acid functionality in the outer core are crosslinked by dissolving the micelles in 20 mM TRIS buffer solution (at pH 7.4) containing 5 mM zinc chloride.

In one embodiment, drug-loaded micelles possessing imidazole functionality in the outer core are crosslinked by addition of zinc chloride to the micelle solution. In certain embodiments, drug-loaded micelles possessing imidazole functionality in the outer core are crosslinked by dissolving the micelles in TRIS buffer solution containing zinc chloride. In yet other embodiments, drug-loaded micelles possessing imidazole acid functionality in the outer core are crosslinked by dissolving the micelles in 20 mM TRIS buffer solution (at pH 7.4) containing 5 mM zinc chloride.

In another embodiment, the -M- moiety of formula X is iron. In certain embodiments, the crosslinking utilizes iron-mediated coupling of carboxylic acids. The interaction between iron and carboxylic acids in biological systems is well known in the art. See Silver, "Chemistry of Iron" 1993. Without wishing to be bound to any particular theory, it is believed that the carboxylic acid will function as a ligand in the carboxylate form (i.e. high pH) but will readily disassociate when the proton ion concentration is sufficiently high (i.e. low pH). (Scheme 3) In some embodiments, the iron moiety is $Fe^{2+}$. In some embodiments, the iron moiety is $Fe^{3+}$.

Scheme 3

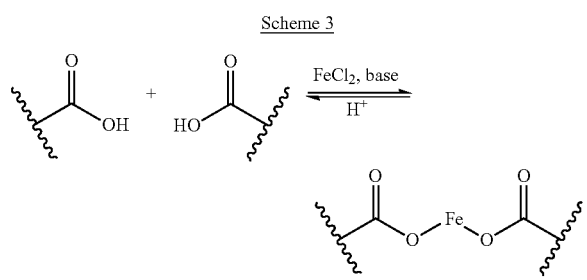

In one embodiment, drug-loaded micelles possessing carboxylic acid functionality in the outer core are crosslinked by addition of iron (II) chloride to the micelle solution. In another embodiment, drug-loaded micelles possessing carboxylic acid functionality in the outer core are crosslinked by addition of iron (III) chloride to the micelle. In certain embodiments, drug-loaded micelles possessing carboxylic acid functionality in the outer core are crosslinked by dissolving the micelles in TRIS buffer solution containing iron (II) chloride. In yet other embodiments, drug-loaded micelles possessing carboxylic acid functionality in the outer core are crosslinked by dissolving the micelles in TRIS buffer solution containing iron (III) chloride.

In certain embodiments, anthracycline-loaded micelles possessing carboxylic acid functionality in the outer core are crosslinked by addition of iron (II) chloride to the micelle solution, followed by adjustment of the pH to 7-8. In other embodiments, anthracycline-loaded micelles possessing carboxylic acid functionality in the outer core are crosslinked by addition of iron (III) chloride to the micelle solution, followed by adjustment of the pH to 7-8.

5. Uses, Methods, and Compositions

Compositions

As described herein, micelles of the present invention having an anthracycline encapsulated therein are useful for treating cancer. According to one embodiment, the present invention relates to the treatment of colorectal cancer. In another embodiment, the present invention relates to the treatment of pancreatic cancer. According to another embodiment, the present invention relates to a method of treating breast cancer. In another embodiment, the present invention relates to the treatment of prostate cancer. According to another embodiment, the present invention relates to a method of treating a cancer selected from ovary, cervix, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, adenoma, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, large intestine, rectum, brain and central nervous system, and leukemia, comprising administering a micelle in accordance with the present invention having an anthracycline encapsulated therein.

P-glycoprotein (Pgp, also called multidrug resistance protein) is found in the plasma membrane of higher eukaryotes where it is responsible for ATP hydrolysis-driven export of hydrophobic molecules. In animals, Pgp plays an important role in excretion of and protection from environmental toxins; when expressed in the plasma membrane of cancer cells, it can lead to failure of chemotherapy by preventing the hydrophobic chemotherapeutic drugs from reaching their targets inside cells. Indeed, Pgp is known to transport hydrophobic chemotherapeutic drugs out of tumor cells. According to one aspect, the present invention provides a method for delivering a an anthracycline to a cancer cell while preventing, or lessening, Pgp excretion of that chemotherapeutic drug, comprising administering a drug-loaded micelle comprising a multi-block polymer of the present invention loaded with an anthracycline.

Compositions

According to another embodiment, the invention provides a composition comprising a micelle of this invention or a pharmaceutically acceptable derivative thereof and a pharmaceutically acceptable carrier, adjuvant, or vehicle. In certain embodiments, the composition of this invention is formulated for administration to a patient in need of such composition. In other embodiments, the composition of this invention is formulated for oral administration to a patient.

The term "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4}\,alkyl)_4$ salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added. In certain embodiments, pharmaceutically acceptable compositions of the present invention are enterically coated.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In certain embodiments, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the drug can be administered to a patient receiving these compositions.

It will be appreciated that dosages typically employed for the encapsulated drug are contemplated by the present invention. In certain embodiments, a patient is administered a drug-loaded micelle of the present invention wherein the dosage of the drug is equivalent to what is typically administered for that drug. In other embodiments, a patient is administered a drug-loaded micelle of the present invention wherein the dosage of the drug is lower than is typically administered for that drug.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

In order that the invention described herein may be more fully understood, the following examples are set forth. It will be understood that these examples are for illustrative purposes only and are not to be construed as limiting this invention in any manner.

EXEMPLIFICATION

Preparation of Multiblock Copolymers and Drug Loaded Micelles of the Present Invention As described generally above, multiblock copolymers of the present invention are prepared using the heterobifunctional PEGs described herein and in U.S. patent application Ser. No. 11/256,735, filed Oct. 24, 2005, published as WO2006/047419 on May 4, 2006 and published as US 20060142506 on Jun. 29, 2006, the entirety of which is hereby incorporated herein by reference. The preparation of multiblock polymers in accordance with the present invention is accomplished by methods known in the art, including those described in detail in U.S. patent application Ser. No. 11/325,020, filed Jan. 4, 2006, published as WO2006/74202 on Jul. 13, 2006 and published as US 20060172914 on Aug. 3, 2006, the entirety of which is hereby incorporated herein by reference.

In each of the Examples below, where an amino acid, or corresponding NCA, is designated "D", then that amino acid, or corresponding NCA, is of the D-configuration. Where no such designation is recited, then that amino acid, or corresponding NCA, is of the L-configuration.

Particle size distribution was determined by dynamic light scattering. Lyopholyzed polymers were dissolved at 5 mg/mL in phosphate buffered saline at pH 7.4 and equilibrated overnight. Each sample was analyzed in a PSS NICOMP 380 with a 690 nm laser at a 90 degree angle or in a Wyatt Dynapro with a 658 nm laser. DLS sizing data was recorded from the volume weighted Gaussian distribution (Nicomp) or Regularization fit (DynaPro).

Example 1

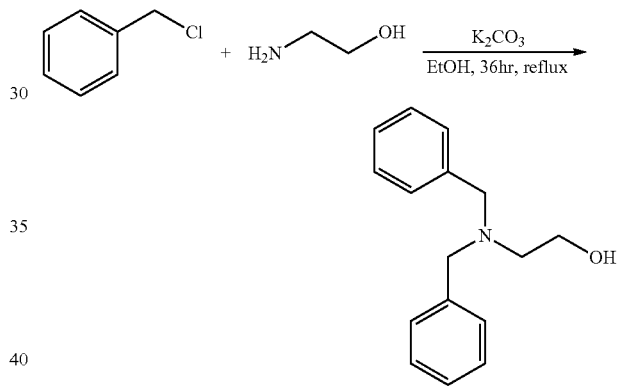

Dibenzylamino Ethanol

Benzyl chloride (278.5 g, 2.2 mol), ethanol amine (60 mL, 1 mol), potassium carbonate (283.1 g, 2.05 mol) and ethanol (2 L) were mixed together in a 3 L 3-neck flask, fitted with an overhead stirrer, a condenser and a glass plug. The apparatus was heated up to reflux for 36 hr, after which the insoluble solid was filtered through a medium frit. The filtrate was recovered and ethanol was removed by rotary evaporation. The viscous liquid was redissolved in ether, the solid suspension removed by filtration and extracted twice against water. The ether solution was kept and the aqueous layer was extracted twice with dichloromethane (2×400 mL). The fraction were recombined, dried over MgSO$_4$, stirred over carbon black for 15 min and filtered through a celite pad. Dichloromethane was removed and the solid was redissolved into a minimal amount of ether (combined volume of 300 mL with the first ether fraction, 300 mL). Hexanes (1700 mL) was added and the solution was heated up gently till complete dissolution of the product. The solution was then cooled down gently, placed in the fridge (+4° C.) overnight and white crystals were obtained. The recrystallization was done a second time. 166.63 g, 69% yield. $^1$H NMR (d$_6$-DMSO) δ 7.39-7.24 (10H), 4.42 (1H), 3.60 (4H), 3.52 (2H), 2.52 (2H).

Example 2

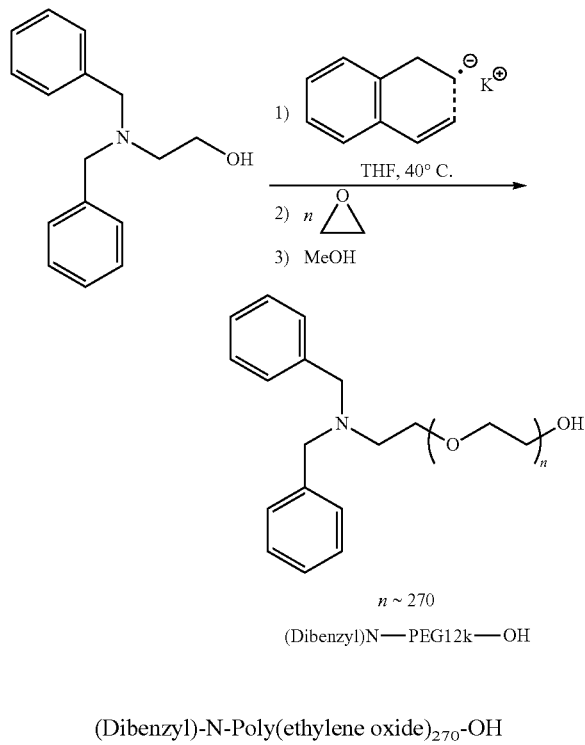

n ~ 270

(Dibenzyl)N—PEG12k—OH (Dibenzyl)-N-Poly(ethylene oxide)$_{270}$-OH

Potassium is freshly cut under dry hexanes to remove all oxide. Potassium (3.13 g, 80 mmol) is weighed in a tared vial containing dry hexanes, then transferred with tweezers to a Schlenk flask with an Argon purge. The flask is then evacuated and any residual hexanes is allowed to evaporate, then the flask backfilled with Argon. Separately, recrystallized, sublimed naphthalene (12.30 g, 100 mmol) is added to a 250 mL round bottom flask. The flask and its contents are dried under vacuum for 15 minutes, then backfilled with Argon. Dry THF (200 mL) is then added to the Schlenk flask containing the potassium, and dry THF (200 mL) is added to the flask containing the naphthalene. Once the naphthalene is completely dissolved in the THF, the entire solution is transferred to the Schlenk flask. A green color begins to appear within 1 minute of the naphthalene solution addition. The solution is stirred overnight to allow for complete reaction, yielding ~400 mL of a 0.2 M potassium naphtalenide solution. The solution is used within 48 hours of preparation. Any unused solution is quenched by the addition of isopropyl alcohol.

The glassware was assembled while still warm. Vacuum was then applied to the assembly and the ethylene oxide line to about 10 mTorr. The setup was backfilled with argon. 2-Dibenzylamino ethanol from Example 1 (3.741 g, 40.4 mmol) was introduced via the sidearm of the jacketed flask under argon overpressure. Two vacuum/argon backfill cycles were applied to the whole setup. THF line was connected to the 14/20 side-arm and vacuum was applied to the whole setup. At this stage, the addition funnel was closed and left under vacuum. THF (4 L) was introduced via the side-arm in the round bottom flask under an argon overpressure. An aliquot of the THF added to the reaction vessel was collected and analyzed by Karl-Fisher colorometric titration to ensure water content of the THF is less than 6 ppm. Next, 2-dibenzylamino ethanol was converted to potassium 2-dibenzylamino ethoxide via addition of potassium naphthalenide (200 mL). Ethylene oxide (500 ml, 10.44 mol) was condensed under vacuum at −30° C. into the jacketed addition funnel, while the alkoxide solution was cooled to 10° C. Once the appropriate amount of ethylene oxide was condensed, the flow of ethylene oxide was stopped, and the liquid ethylene oxide added directly to the cooled alkoxide solution. After complete ethylene oxide addition, the addition funnel was closed and the reaction flask backfilled with argon. While stirring, the following temperature ramp was applied to the reaction: 12 hrs at 20° C., 1 hr from 20° C. to 40° C. and 3 days at 40° C. The reaction went from a light green tint to a golden yellow color. Upon termination with an excess methanol, the solution color changed to light green. The solution was precipitated into ether and isolated by filtration. 459 g, 99% yield was recovered after drying in a vacuum oven overnight. $^1$H NMR (d6-DMSO) δ 7.4-7.2 (10H), 4.55 (1H), 3.83-3.21 (910H) ppm.

Example 3

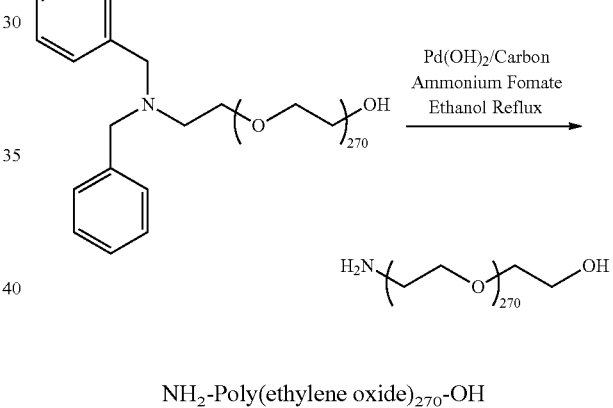

NH$_2$-Poly(ethylene oxide)$_{270}$-OH (Dibenzyl)-N-poly(ethylene oxide)$_{270}$-OH from Example 2 (455 g, 39.56 mmol) was split into two equal amounts and was introduced into two 2 L flasks. A separate batch of (dibenzyl)-N-poly(ethylene oxide)$_{270}$-OH (273 g, 23.74 mmol) was added to a third 2 L flask. The following steps were repeated for each flask. The following steps were repeated for each flask. (Dibenzyl)-N-poly(ethylene oxide)$_{270}$-OH (~225 g), Pd(OH)$_2$/C (32 g, 45.6 mmol), ammonium formate (80 g, 1.27 mol) and ethanol (1.2 L) were mixed together in a 2 L flask. The reaction was heated to 80° C. while stirring for 24 hrs. The reaction was cooled to room temperature and filtered through a triple layer Celite/MgSO$_4$/Celite pad. The MgSO$_4$ powder is fine enough that very little Pd(OH)$_2$/C permeates through the pad. Celite helps prevent the MgSO$_4$ layer from cracking. At this stage, the three filtrates were combined, precipitated into ~30 L of ether and filtered through a medium glass frit. The wet polymer was then dissolved into 4 L of water, 1 L of brine and 400 mL of saturated K$_2$CO$_3$ solution. The pH was checked to be ~11 by pH paper. The aqueous solution was introduced into a 12 L extraction funnel, rinsed once with 4 L of ether and extracted 4 times with dichloromethane (6 L, 6 L, 6 L, 2 L). Dichloromethane fractions were recombined, dried over MgSO₄ (3 kg), filtered, concentrated to ~3 L by rotary evaporation and precipitated into diethyl ether (30 L). 555 g, 75% yield of the title compound was recovered after filtration and evaporation to dryness in a vacuum oven. ¹H NMR (d6-DMSO) 4.55 (1H), 3.83-3.21 (910H), 2.96 (2H) ppm.

Example 4

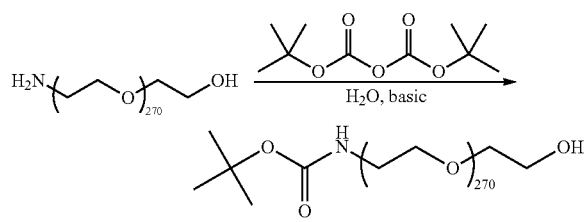

Boc-NH-Poly(ethylene oxide)$_{270}$-OH

NH$_2$-Poly(ethylene oxide)$_{270}$-OH (555 g, 48.26 mmol) from Example 3 was dissolved into 4 L of DI water. A saturated solution of K$_2$CO$_3$ (120 mL) was added, to keep the pH basic (pH ~11 with pH paper). Di-tert-butyl dicarbonate (105 g, 0.48 mol) was added to the aqueous solution of NH$_2$-poly(ethylene oxide)$_{270}$-OH and allowed to stir at room temperature overnight. At this stage, a 5 mL aliquot of the reaction was extracted with 10 mL of dichloromethane and the dichloromethane extract precipitated into ether. A ¹H NMR was run to ensure completion of the reaction. Thereafter, the aqueous solution was placed into a 12 L extraction funnel, was rinsed once with ether (4 L) and extracted three times with dichloromethane (6 L, 6 L and 6 L). The organic fractions were recombined, dried over MgSO₄ (3 kg), filtered, concentrated to ~4 L and precipitated into 30 L of ether. The white powder was filtered and dried overnight in a vacuum oven, giving 539 g of the title compound in 97% yield. ¹H NMR (d$_6$-DMSO) δ 6.75 (1H), 4.55 (1H), 3.83-3.21 (910H), 3.06 (2H), 1.37 (9H) ppm.

Example 5

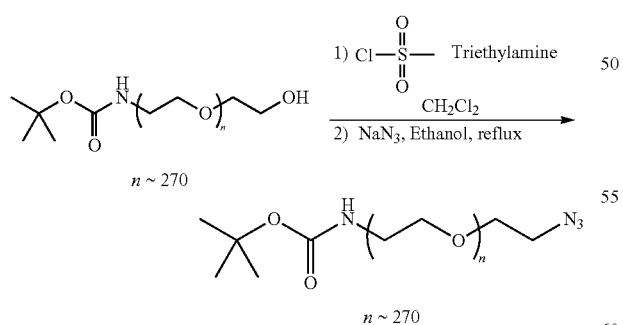

Boc-NH-Poly(ethylene oxide)$_{270}$-N$_3$

Boc-NH-Poly(ethylene oxide)$_{270}$-OH (539 g, 49.9 mmol) from Example 4 was placed into a 6 L jacketed flask and dried by azeotropic distillation from toluene (3 L). It was then dissolved into 3 L of dry dichloromethane under inert atmosphere. The solution was cooled to 0° C., methanesulfonyl chloride (10.9 mL, 140.8 mmol) was added followed by triethylamine (13.1 mL, 94 mmol). The reaction was allowed to warm to room temperature and proceeded overnight under inert atmosphere. The solution was evaporated to dryness by rotary evaporation and used as-is for the next step.

NaN$_3$ (30.5 g, 470 mmol) and 3 L of ethanol were added to the flask containing the polymer. The solution was heated to 80° C. and allowed to react overnight. It was then evaporated to dryness by rotary evaporation (bath temperature of 55° C.) and dissolved in 2 L of dichloromethane. The latter solution was the filtered through a Büchner funnel fitted with a Whatman paper #1 to remove most of the salts. The solution was concentrated down to ~1 L by rotary evaporation. The product was purified by silica gel flash column chromatography using a 8 in. diameter column with a coarse frit. About 7 L of dry silica gel were used. The column was packed with 1:99 MeOH/CH$_2$Cl$_2$ and the product was loaded and eluted onto the column by pulling vacuum from the bottom of the column. The elution profile was the following: 1:99 MeOH/CH$_2$Cl$_2$ for 1 column volume (CV), 3:97 MeOH/CH$_2$Cl$_2$ for 2 CV and 10:90 MeOH/CH$_2$Cl$_2$ for 6 CV. The different polymer-containing fractions were recombined (~40 L of dichloromethane), concentrated by rotary evaporation and precipitated into a 10-fold excess of diethyl ether. The title compound was recovered by filtration as a white powder and dried overnight in vacuo, giving 446.4 g, 82% yield. ¹H NMR (d$_6$-DMSO) δ 6.75 (1H), 3.83-3.21 (910H), 3.06 (2H), 1.37 (9H) ppm. $M_n$ (MALDI-TOF)=11,554 g/mol. PDI (DMF GPC)=1.04

Example 6

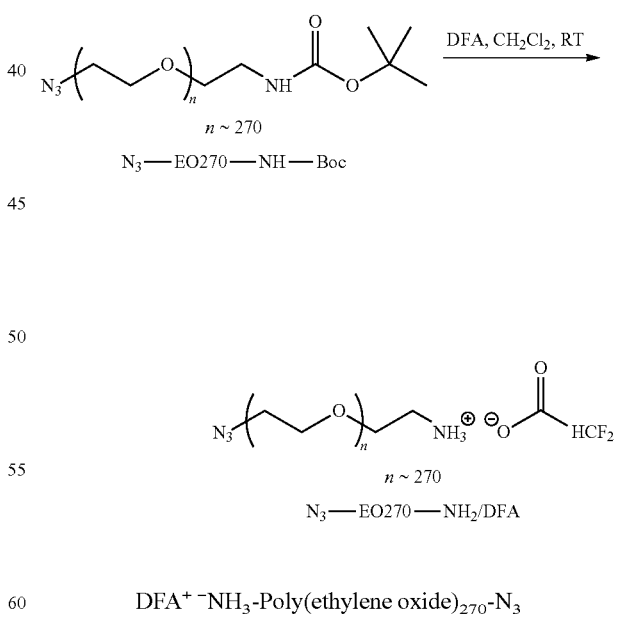

DFA$^+$ $^-$NH$_3$-Poly(ethylene oxide)$_{270}$-N$_3$

Boc-NH-Poly(ethylene oxide)$_{270}$-N$_3$ (313 g, 27.2 mmol) from Example 5 was weighed into a 2 L beaker, 600 mL of DFA, 600 mL of dichloromethane were added. The solution was stirred at room temperature for 32 hr and the polymer was recovered by two consecutive precipitation in ether (2×30 L). The white powder was dried overnight in a vacuum oven to afford the title compound. (306 g, 98% yield). ¹H NMR (d₆-DMSO) δ 7.67 (3H), 6.13 (1H), 3.82-3.00 (1060H), 2.99 (2H).

Example 7

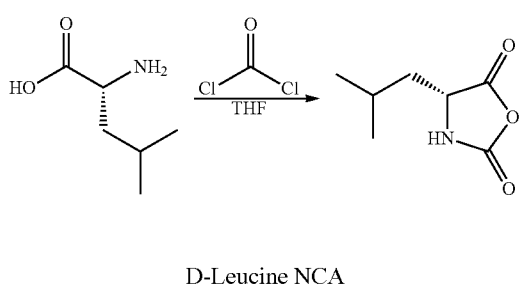

D-Leucine NCA

H-D-Leu-OH (100 g, 0.76 mol) was suspended in 1 L of anhydrous THF and heated to 50° C. while stirring heavily. Phosgene (20% in toluene) (500 mL, 1 mol) was added the amino acid suspension. After 1 h 20 min, the amino acid dissolved, forming a clear solution. The solution was concentrated on the rotovap, transferred to a beaker, and hexane was added to precipitate the product. The white solid was isolated by filtration and dissolved in toluene (~700 mL) with a small amount of THF (~60 mL). The solution was filtered over a bed of Celite to remove any insoluble material. An excess of hexane (~4 L) was added to the filtrate to precipitate the product. The NCA was isolated by filtration and dried in vacuo. (91 g, 79% yield) D-Leu NCA was isolated as a white, crystalline solid. ¹H NMR (d₆-DMSO) δ 9.13 (1H), 4.44 (1H), 1.74 (1H), 1.55 (2H), 0.90 (6H) ppm.

Example 8

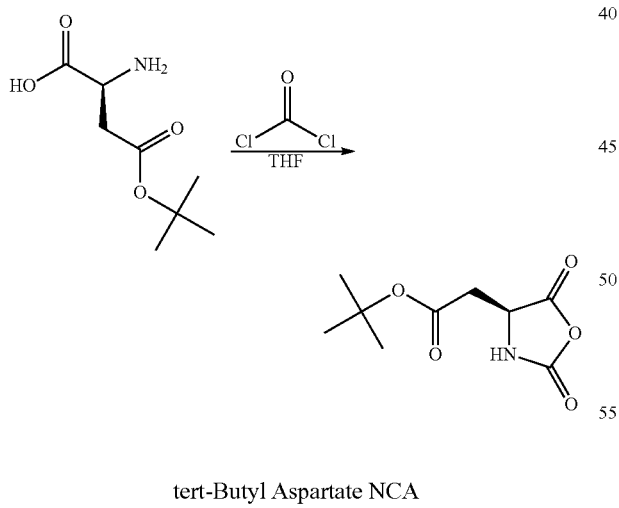

tert-Butyl Aspartate NCA

H-Asp(OBu)-OH (120 g, 0.63 mol) was suspended in 1.2 L of anhydrous THF and heated to 50° C. while stirring heavily. Phosgene (20% in toluene) (500 mL, 1 mol) was added the amino acid suspension. After 1 h 30 min, the amino acid dissolved, forming a clear solution. The solution was concentrated on the rotovap, transferred to a beaker, and hexane was added to precipitate the product. The white solid was isolated by filtration and dissolved in anhydrous THF. The solution was filtered over a bed of Celite to remove any insoluble material. An excess of hexane was added to precipitate the product. The NCA was isolated by filtration and dried in vacuo. 93 g (68%) of Asp(OBu) NCA was isolated as a white, crystalline solid. ¹H NMR (d₆-DMSO) δ 8.99 (1H), 4.61 (1H), 2.93 (1H), 2.69 (1H), 1.38 (9H) ppm.

Example 9

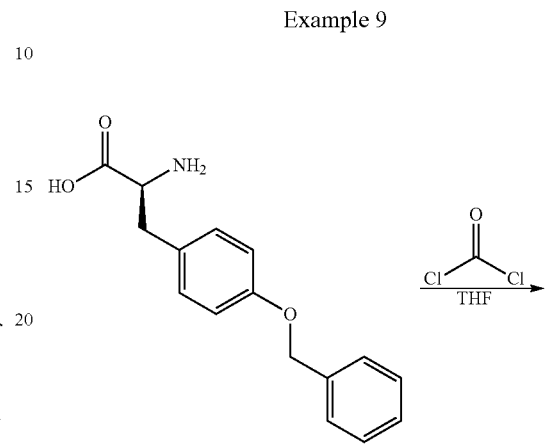

Benzyl Tyrosine NCA

H-Tyr(OBzl)-OH (140 g, 0.52 mol) was suspended in 1.5 L of anhydrous THF and heated to 50° C. while stirring heavily. Phosgene (20% in toluene) (500 mL, 1 mol) was added the amino acid suspension via cannulation. The amino acid dissolved over the course of approx. 1 h 30, forming a pale yellow solution. The solution was first filtered through a Buchner fitted with a Whatman paper #1 to remove any particles still in suspension. Then, the solution was concentrated by rotary evaporation, transferred to a beaker, and hexane was added to precipitate the product. The off-white solid was isolated by filtration and dissolved in anhydrous THF (~600 mL). The solution was filtered over a bed of Celite to remove any insoluble material. An excess of hexane (~6 L) was added to the filtrate to precipitate the product. The NCA was isolated by filtration and dried in vacuo. 114.05 g, 74.3% of Tyr(OBzl) NCA was isolated as a off-white powder. ¹H NMR (d₆-DMSO) δ 9.07 (1H), 7.49-7.29 (5H), 7.12-7.07 (2H), 6.98-6.94 (2H), 5.06 (2H), 4.74 (1H), 3.05-2.88 (2H) ppm.

Example 10
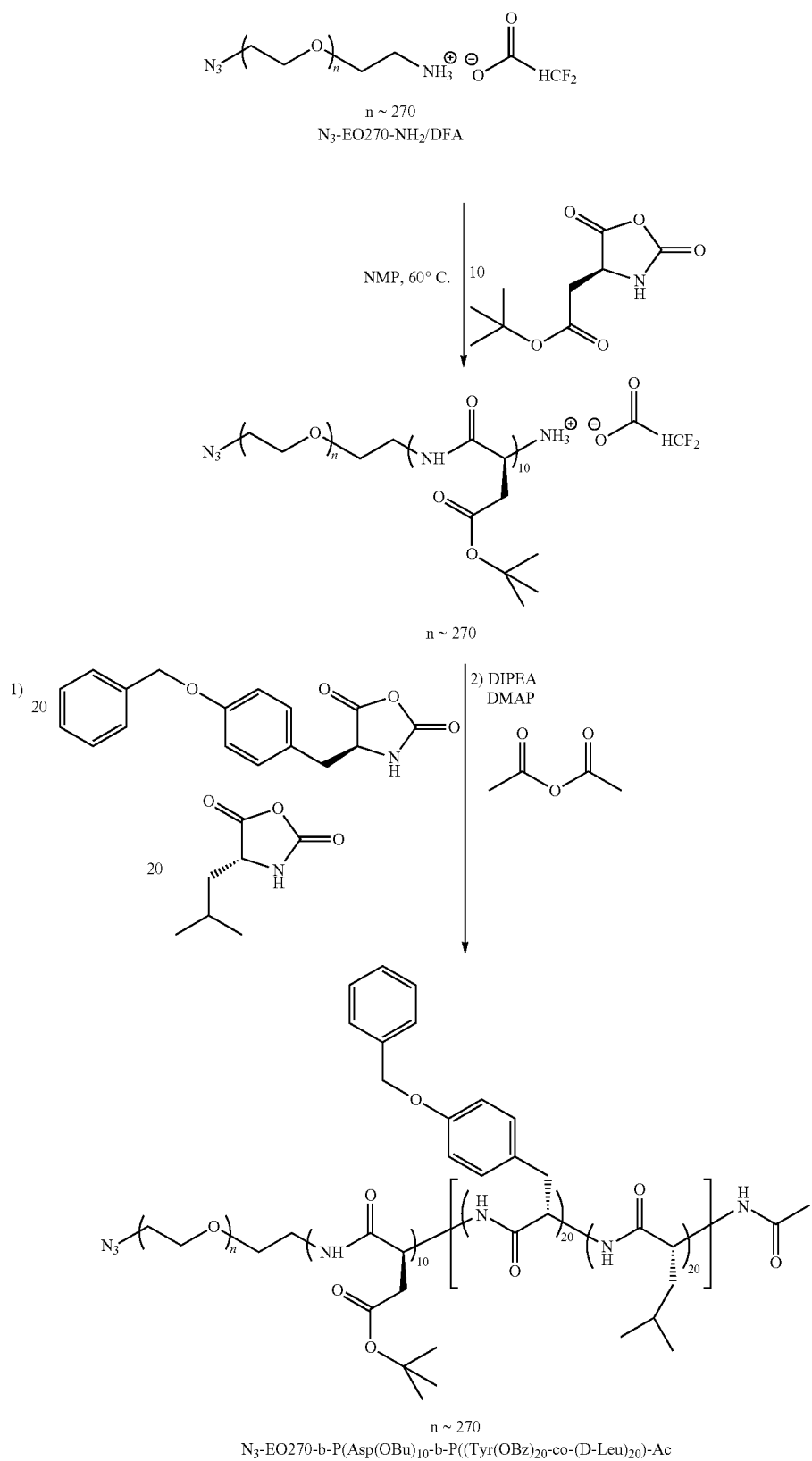

N$_3$-Poly(ethylene oxide)$_{270}$-b-Poly(Asp(OBu)$_{10}$)-b-Poly(dLeu$_{20}$-co-Tyr(OBzl)$_{20}$)-Ac

Step A:

DFA$^-$ $^+$NH$_3$-Poly(ethylene oxide)$_{270}$-N$_3$ (294 g, 25.6 mmol) from Example 6 was weighed into an oven-dried, 6 L jacketed round-bottom flask, dissolved in toluene (2 L), and dried by azeotropic distillation. After distillation, the polymer was left under vacuum overnight before adding the NCA. Asp(OBu) NCA (55 g, 256 mmol) from Example 8 was added to the flask, the flask was evacuated under reduced pressure, and subsequently backfilled with nitrogen gas. Dry N-methylpyrrolidone (NMP) (1.8 L) was introduced by cannula and the solution was heated to 60° C. The reaction mixture was allowed to stir for 48 hours at 60° C. under nitrogen gas.

Step B:

D-Leu NCA (82 g, 0.522 mol) (Example 7) and Tyr (OBzl) NCA (155 g, 0.522 mol) (Example 9) were dissolved under nitrogen gas into 360 ml of NMP into an oven-dried, round bottom flask and the mixture was subsequently cannulated to the polymerization reaction via a syringe. The solution was allowed to stir at 60° C. for another three days and 12 hrs at which point the reaction was complete (by HPLC). The solution was cooled to room temperature and 25 mL were precipitated into 1 L of ether.

Step C: Diisopropylethylamine (DIPEA) (50 mL), dimethylaminopyridine (DMAP) (5 g), and acetic anhydride (50 mL) were added to the rest of the solution. Stirring was continued overnight at room temperature. The polymer was precipitated into diethyl ether (50 L) and isolated by filtration. The title product was isolated by filtration and dried in vacuo to give the block copolymer as an off-white powder (426 g, Yield=73%). $^1$H NMR (d$_6$-DMSO) δ 8.43-7.62 (50H), 7.35 (100H), 7.1 (40H), 6.82 (40H), 4.96 (40H), 4.63-3.99 (50H), 3.74-3.2 (1500H), 3.06-2.6 (60H), 1.36 (90H), 1.27-0.47 (180).

Example 11

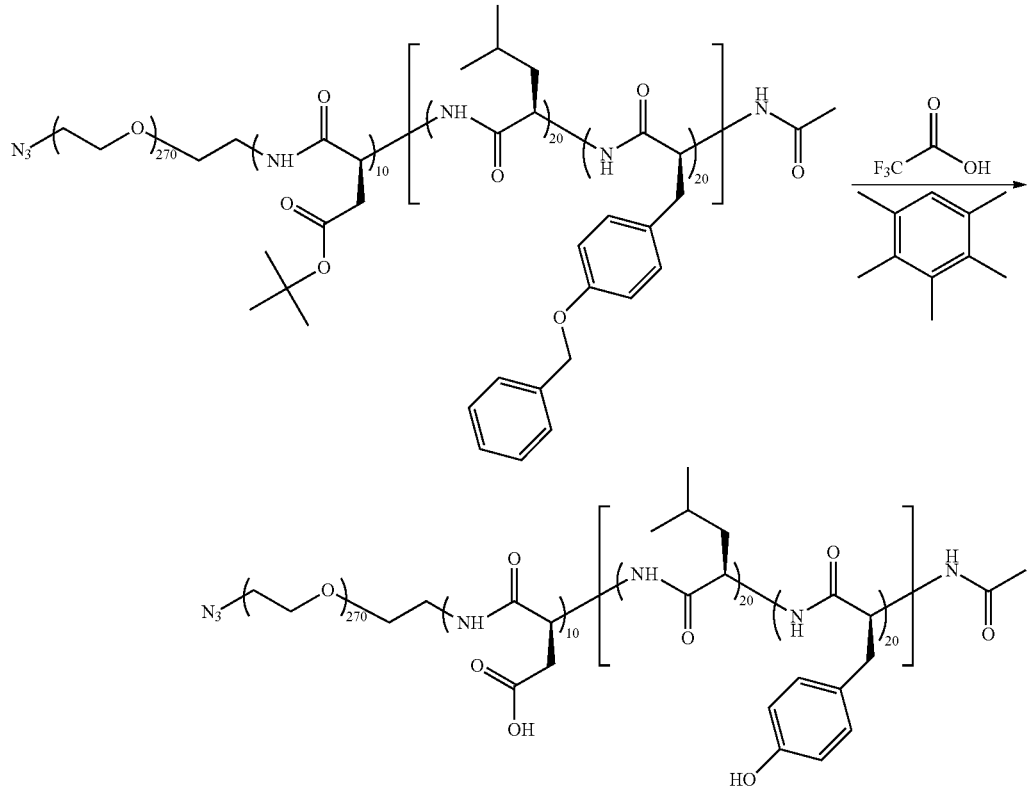

N$_3$-Poly(ethylene oxide)$_{270}$-b-Poly(Asp$_{10}$)-b-Poly(dLeu$_{20}$-co-Tyr$_{20}$)-Ac N$_3$-Poly(ethylene oxide)$_{270}$-b-Poly(Asp(OBu)$_{10}$)-b-Poly(dLeu$_{20}$-co-Tyr(OBzl)$_{20}$)-Ac (420 g, 20.5 mmol) from Example 10 was dissolved into 3 L of a solution of pentamethyl benzene (PMB, 0.5M) in trifluoroacetic acid (TFA). The reaction was allowed to stir for five hours at room temperature. The solution was precipitated into diethyl ether (50 L) and the solid was recovered by filtration through a 2 L medium frit. The polymer was redissolved into 4 L of dichloromethane and precipitated into diethyl ether (~50 L). The polymer was redissolved one more time into a 50:50 dichloromethane:isopropanol mixture and diethyl ether was poured on the top of the solution (~50 L). The title compound was obtained as an off-white polymer after drying the product overnight in vacuo (309.3 g, 83% yield). $^1$H NMR (d$_6$-DMSO) δ 12.2 (2H), 9.1 (13H), 8.51-7.71 (49H), 6.96 (29H), 6.59 (26H), 4.69-3.96 (59H), 3.81-3.25 (1040H), 3.06-2.65 (45H), 1.0-0.43 (139). $^{13}$C NMR (d$_6$-DMSO) δ 171.9, 171, 170.5, 170.3, 155.9, 130.6, 129.6, 127.9 115.3, 114.3, 70.7, 69.8, 54.5, 51.5, 50, 49.8, 49.4, 36.9, 36, 24.3, 23.3, 22.3, 21.2. IR (ATR) 3290, 2882, 1733, 1658, 1342, 1102, 962 cm$^{-1}$. M$_n$ (MALDI-TOF)=17,300 g/mol. PDI (DMF GPC)=1.1

Example 12

Synthesis of N$_3$-EO270-b-Poly(Asp$_{10}$)-b-Poly(dLeu$_{20}$-co-Tyr(OBzl)$_{20}$)-Ac

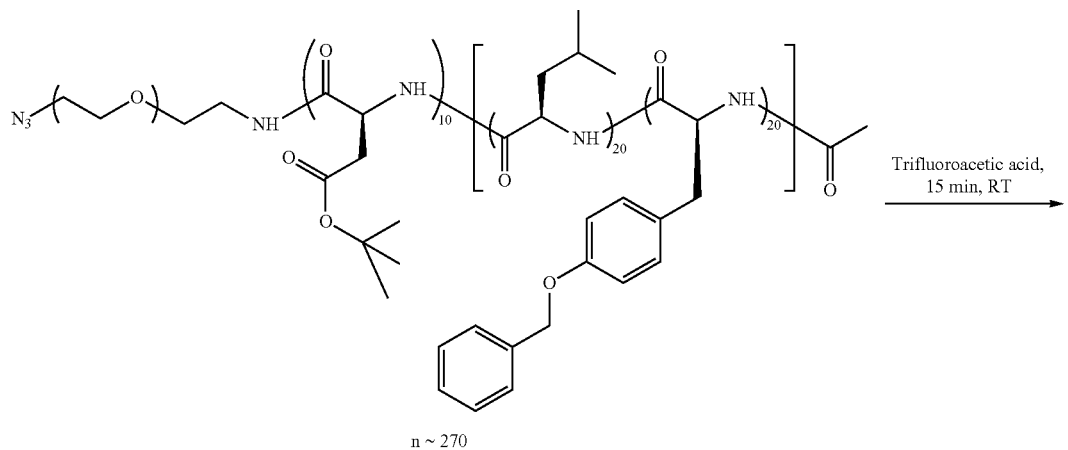

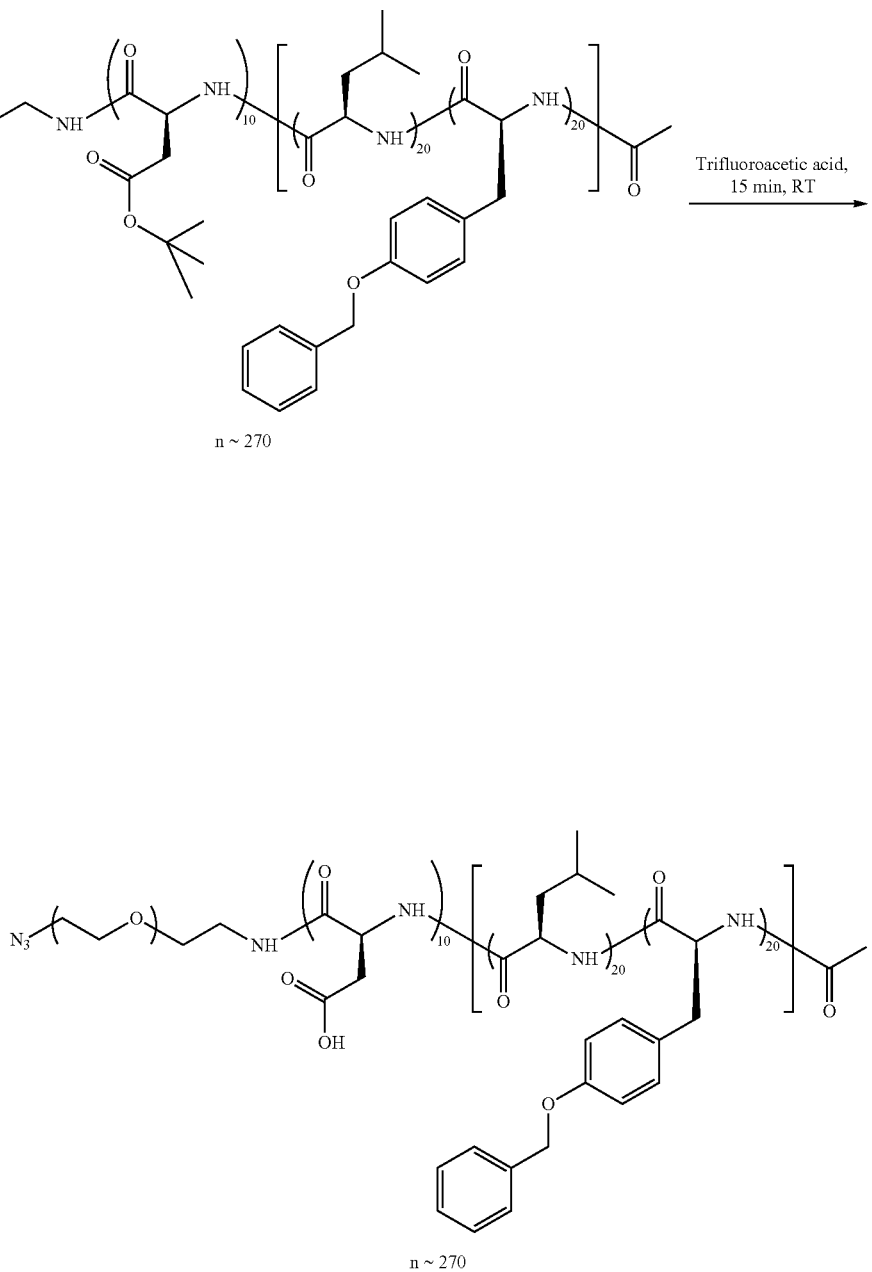

N$_3$-EO270-b-Poly(Asp(OBu)$_{10}$)-b-Poly(dLeu$_{20}$-co-Tyr(OBzl)$_{20}$)-Ac (6 g, 0.26 mmol) was weighed out into a beaker and TFA (60 mL) and dichloromethane (30 mL) were added. The solution was stirred at room temperature for 1 hr before being precipitated twice into cold ether (1 L). The product was recovered by filtration as an off-white powder (4.75 g, 79% yield). $^1$H NMR (d$_6$-DMSO) δ 12.49-12.30 (5H), 8.46-7.75 (28H), 7.49-7.23 (64H), 7.22-7.01 (23H), 6.93-6.72 (22H), 5.10-4.86 (22H), 4.67-4.02 (25H), 3.72-3.23 (1040H), 3.11-2.61 (29H), 1.72-0.42 (86H) ppm.

Example 13

Synthesis of $N_3$-EO270-b-Poly($His_{10}$)-b-Poly($dLeu_{20}$-co-Tyr(OBzl)$_{20}$)-Ac

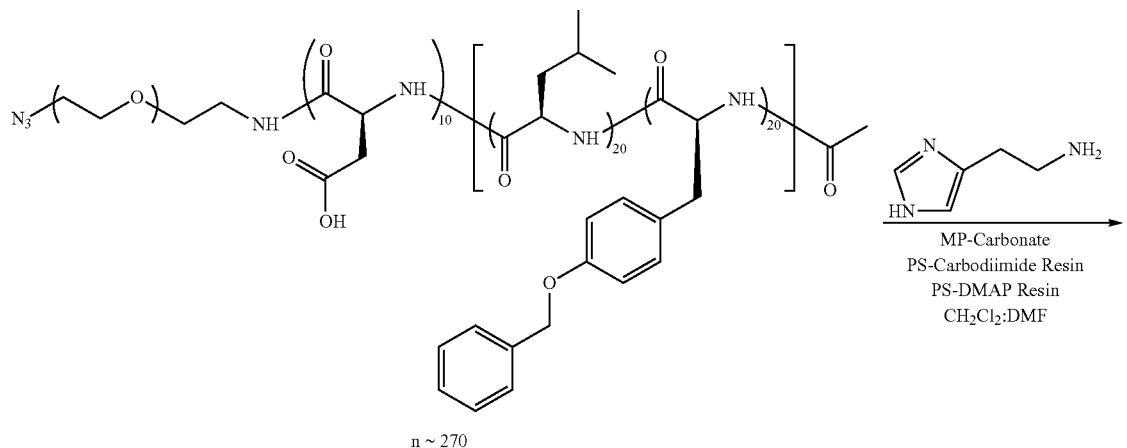

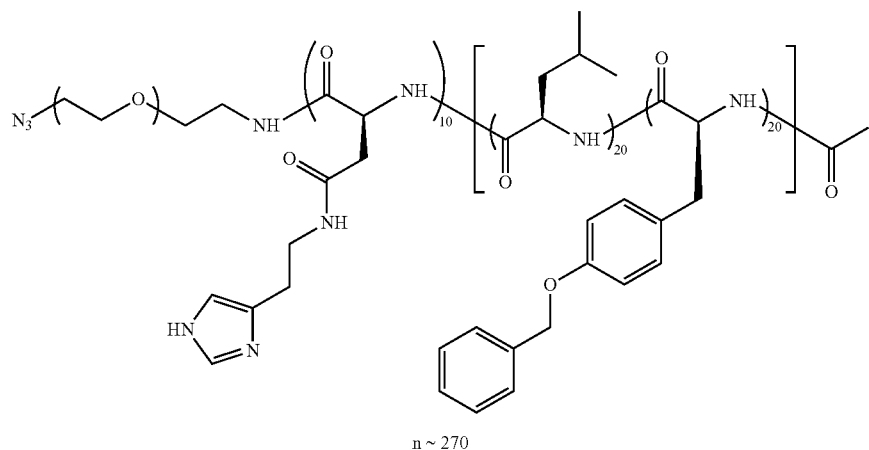

Histamine dihydrochloride (0.41 g, 2.23 mmol) was dissolved into DMF (dry, 10 mL). MP-carbonated resin was added (2.76 mmol/g, 2.42 g, 6.68 mmol) to the solution and was stirred for 2 hours at room temperature. The reaction solution was filtered through a Whatman paper #1 and the liquid was added to a 100 mL flask containing $N_3$-EO270-b-Poly($Asp_{10}$)-b-Poly($dLeu_{20}$-co-Tyr(OBzl)$_{20}$)-Ac (1.5 g, 75 µmmol), PS-DMAP (1.47 mmol/g, 0.51 g, 0.75 mmol), PS-Carbodiimide (1.33 mmol/g, 1.69 g, 2.25 mmol, and $CH_2Cl_2$ (10 mL). The reaction was left under nitrogen at room temperature overnight. It was then filtered through a Whatman paper #1 and the solution was put into a 3500 molecular weight cut-off dialysis bag. The solution was dialyzed three times against MeOH, three times against water and freeze-dried. A white powder was obtained (1.34 g, 78.7% yield). $^1$H NMR ($d_6$-DMSO) δ 8.48-7.72 (28H), 7.61 (3H), 7.45-7.23 (64H), 7.22-7.00 (25H), 6.95 (3H), 5.06-4.83 (24H), 4.61-4.02 (37H), 3.80-3.14 (1040H), 3.09-2.59 (37H), 1.80-0.44 (73H).

Example 14

Synthesis of $N_3$-EO270-b-Poly($His_{10}$)-b-Poly($dLeu_{20}$-co-$Tyr_{20}$)-Ac

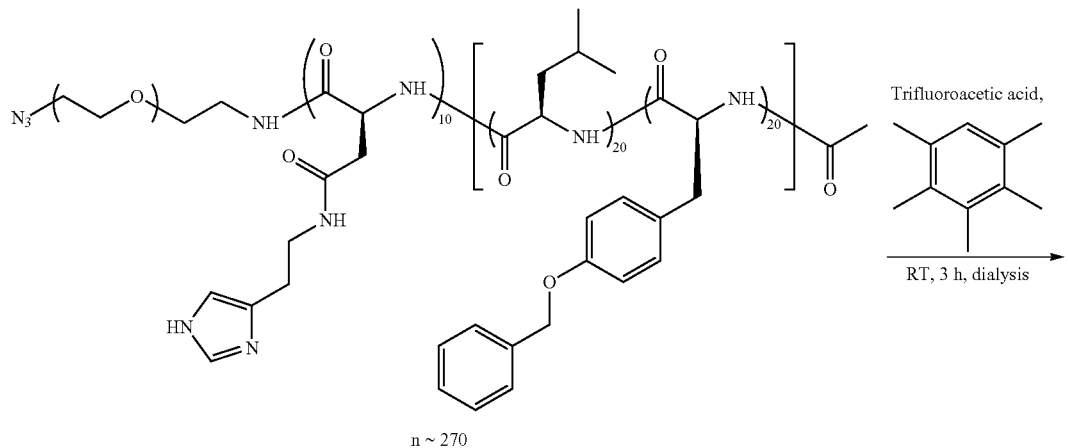

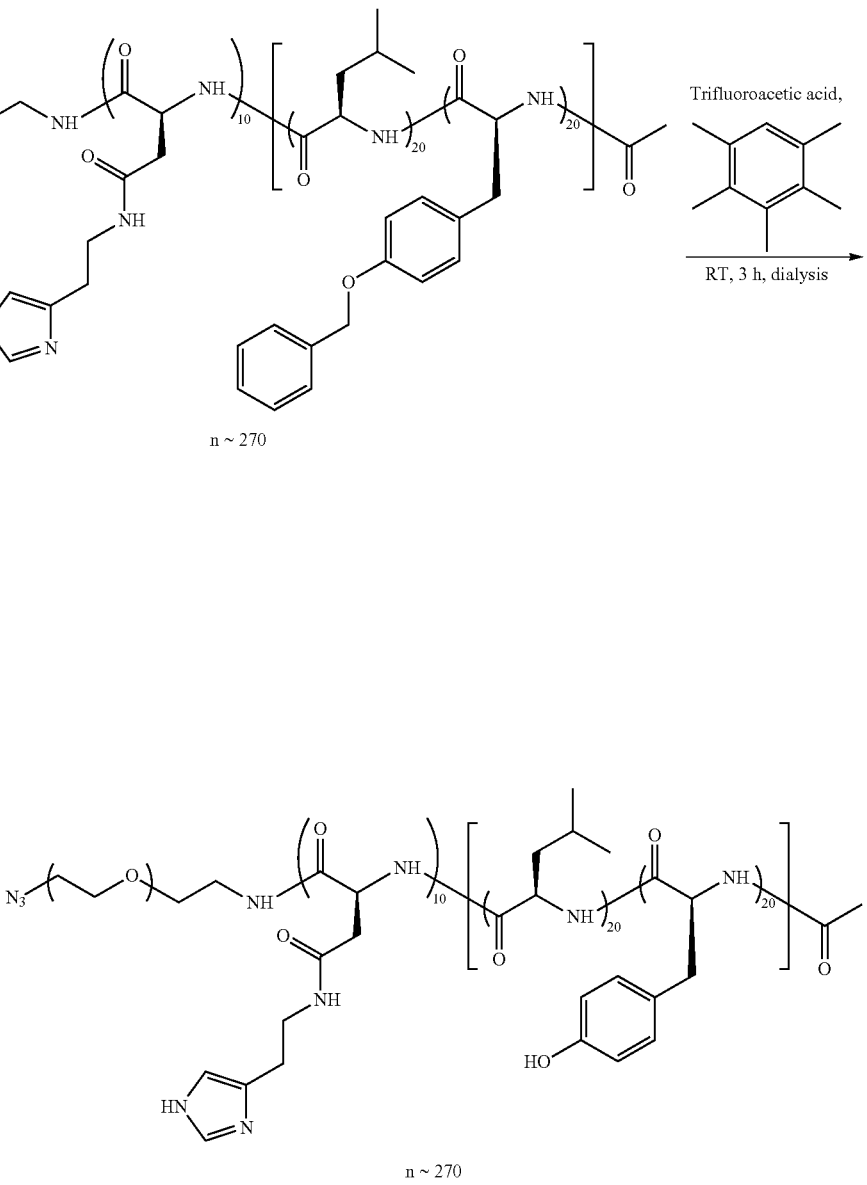

$N_3$-EO270-b-Poly($His_{10}$)-b-Poly($dLeu_{20}$-co-Tyr(OBzl)$_{20}$)-Ac (1 g, 44 μmmol) was mixed with 20 mL of a 0.5M pentamethylbenzene in TFA solution. The reaction was left under stirring at room temperature for 3 h and was then placed into a 3500 molecular weight cut-off dialysis bag. The solution was dialyzed three times against MeOH, three times against water and freeze-dried. A white powder was obtained (0.5 g, 57% yield). $^1$H NMR ($d_6$-DMSO) δ 9.25-9.00 (9H), 8.46-7.51 (30H), 7.26-6.86 (26H), 6.73-6.46 (24H), 4.66-4.01 (36H), 3.86-3.07 (1040H), 3.07-2.57 (31H), 1.92-0.5 (84H) ppm. $^{13}$C NMR ($d_6$-DMSO) δ 172.0, 171.0, 170.7, 155.9, 130.2, 129.9, 127.9, 127.7, 114.7, 114.6, 70.09, 54.9, 51.7, 51.3, 50.0, 360, 23.8, 22.9, 22.4, 21.6 ppm.

Example 15
Synthesis of N₃-EO270-b-Poly(His₁₀)-b-Poly(dLeu₂₀-co-Tyr(OBzl)₂₀)-Ac
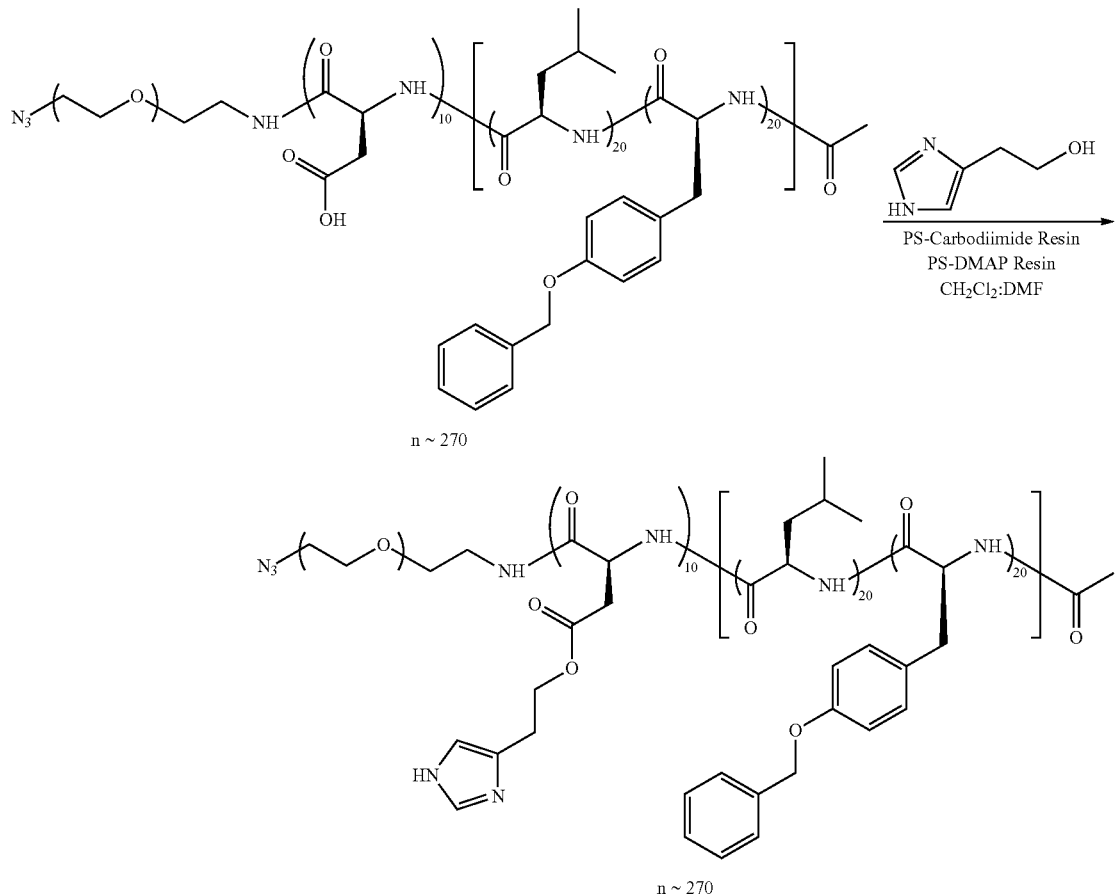
Example 16
Synthesis of N₃-EO270-b-Poly(His₁₀)-b-Poly(dLeu₂₀-co-Tyr₂₀)-Ac
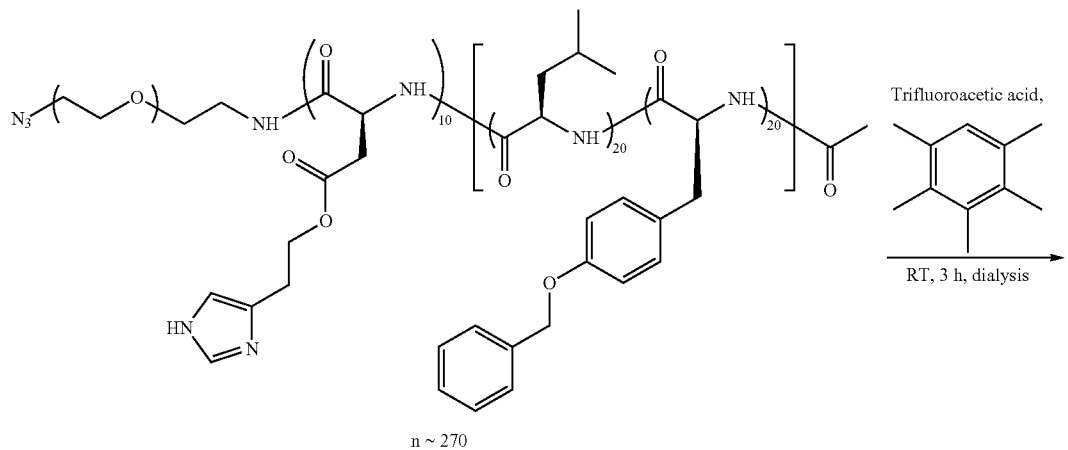

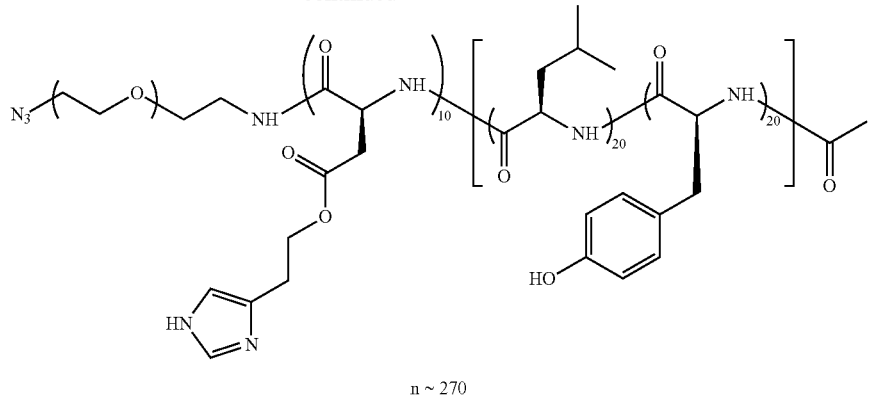
n ~ 270
Example 17
Click of CXCR4-Alkyne onto N$_3$-EO270-b-Poly(Asp$_{10}$)-b-Poly(dLeu$_{20}$-co-Tyr(OBzl)$_{20}$)-Ac
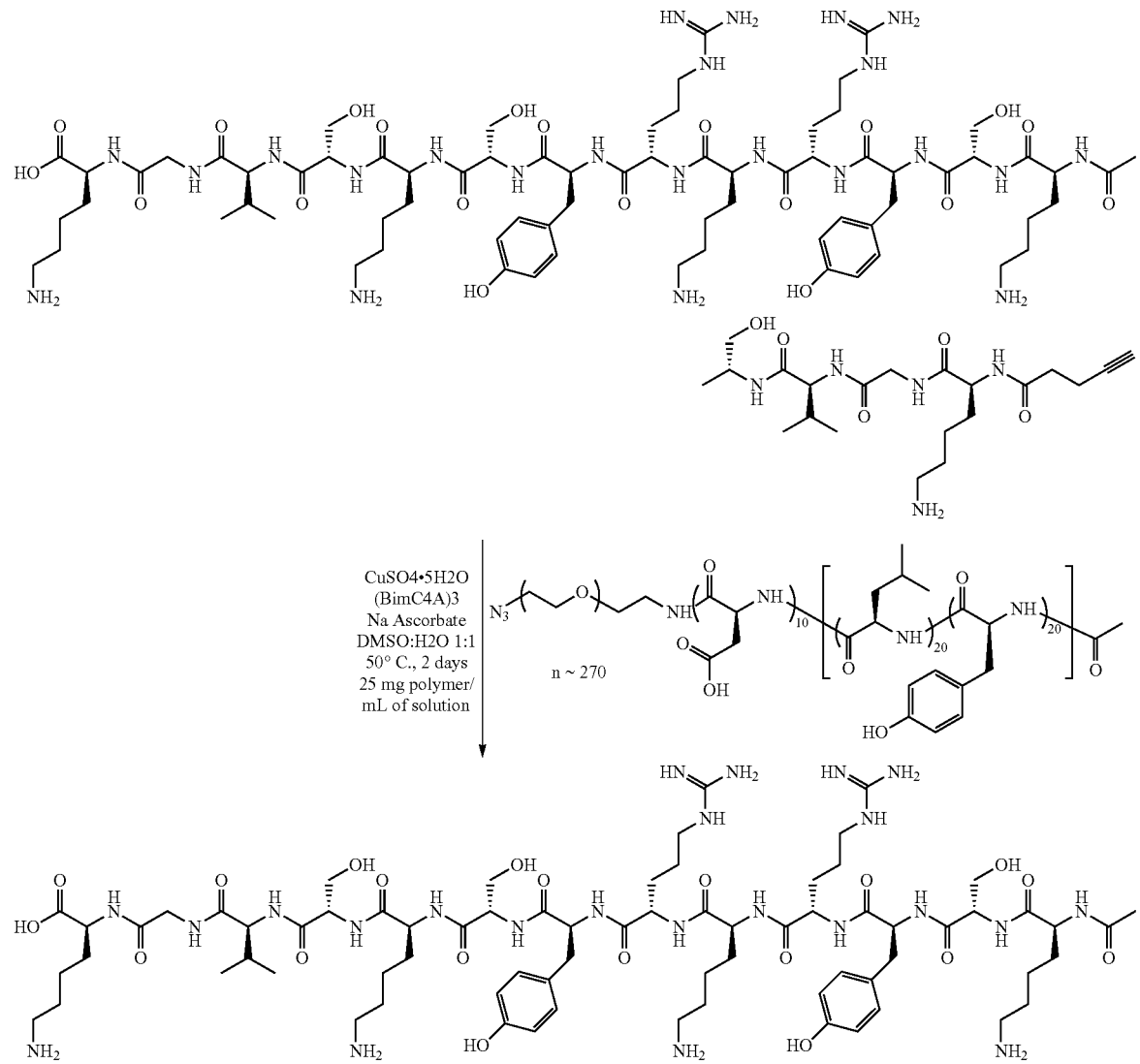

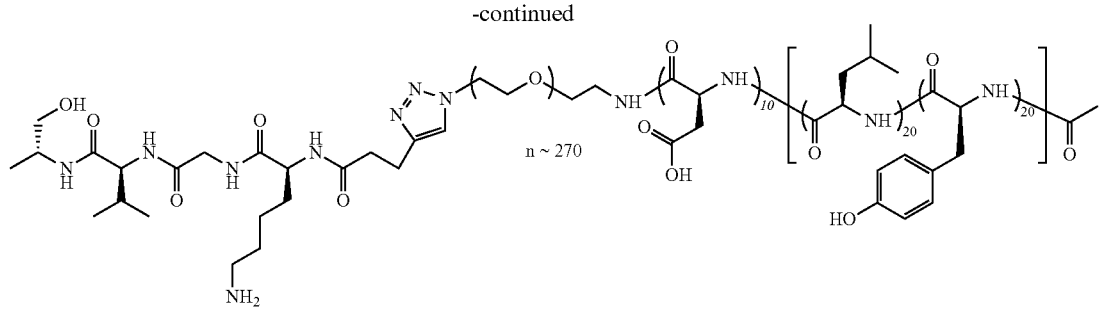
Example 18
Click of CXCR4-Alkyne onto N₃-EO270-b-Poly(Asp(His)₁₀)-b-Poly(dLeu₂₀-co-Tyr(OBzl)₂₀)-Ac
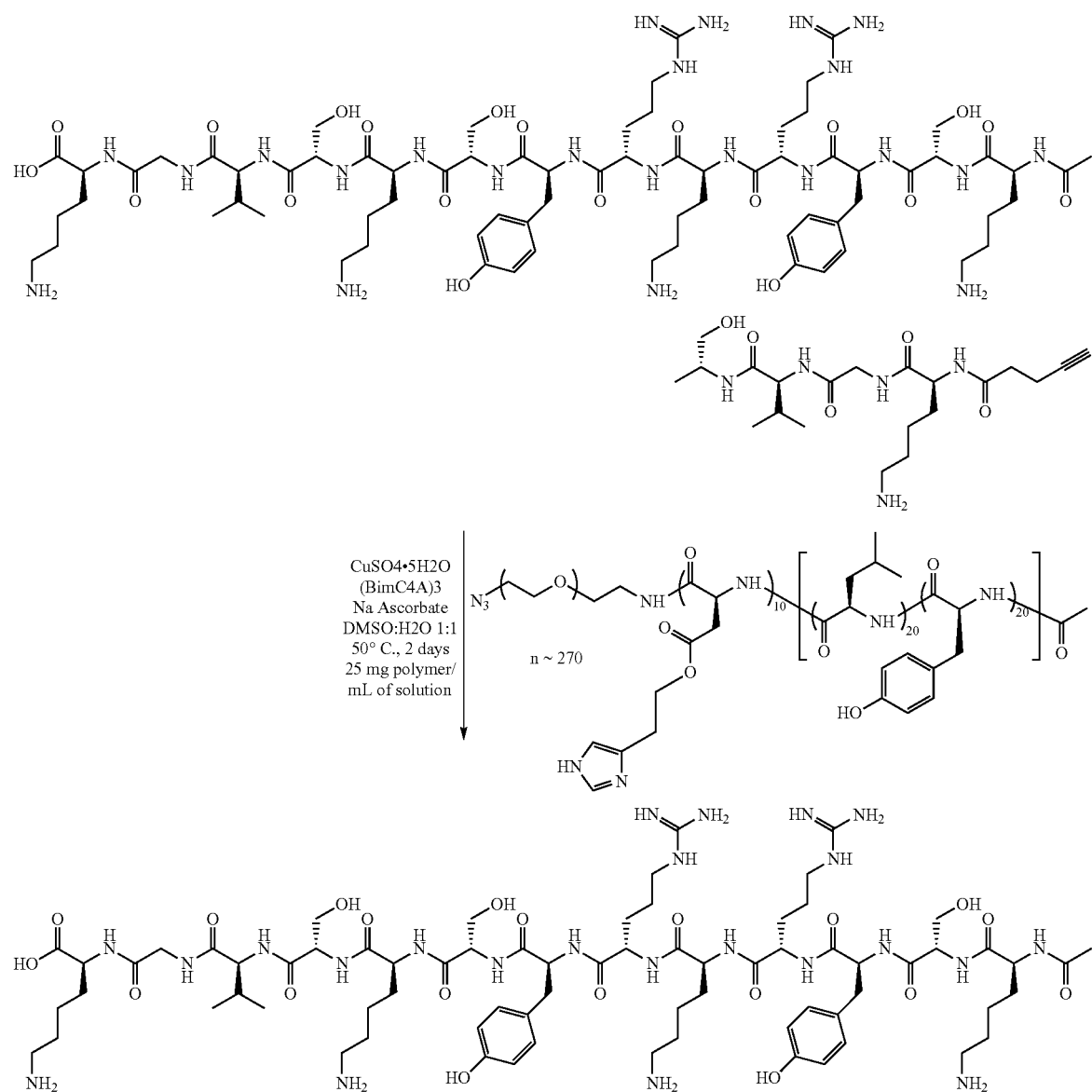

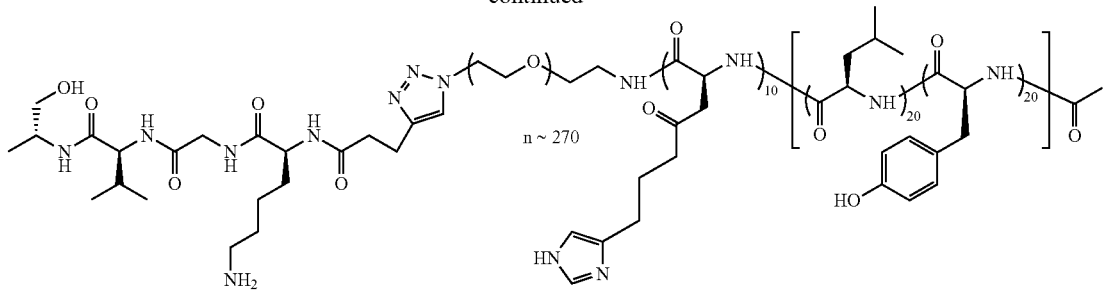
Example 19
Click of HER2Fantin-Alkyne onto $N_3$-EO270-b-Poly(Asp$_{10}$)-b-Poly(dLeu$_{20}$-co-Tyr(OBzl)$_{20}$)-Ac

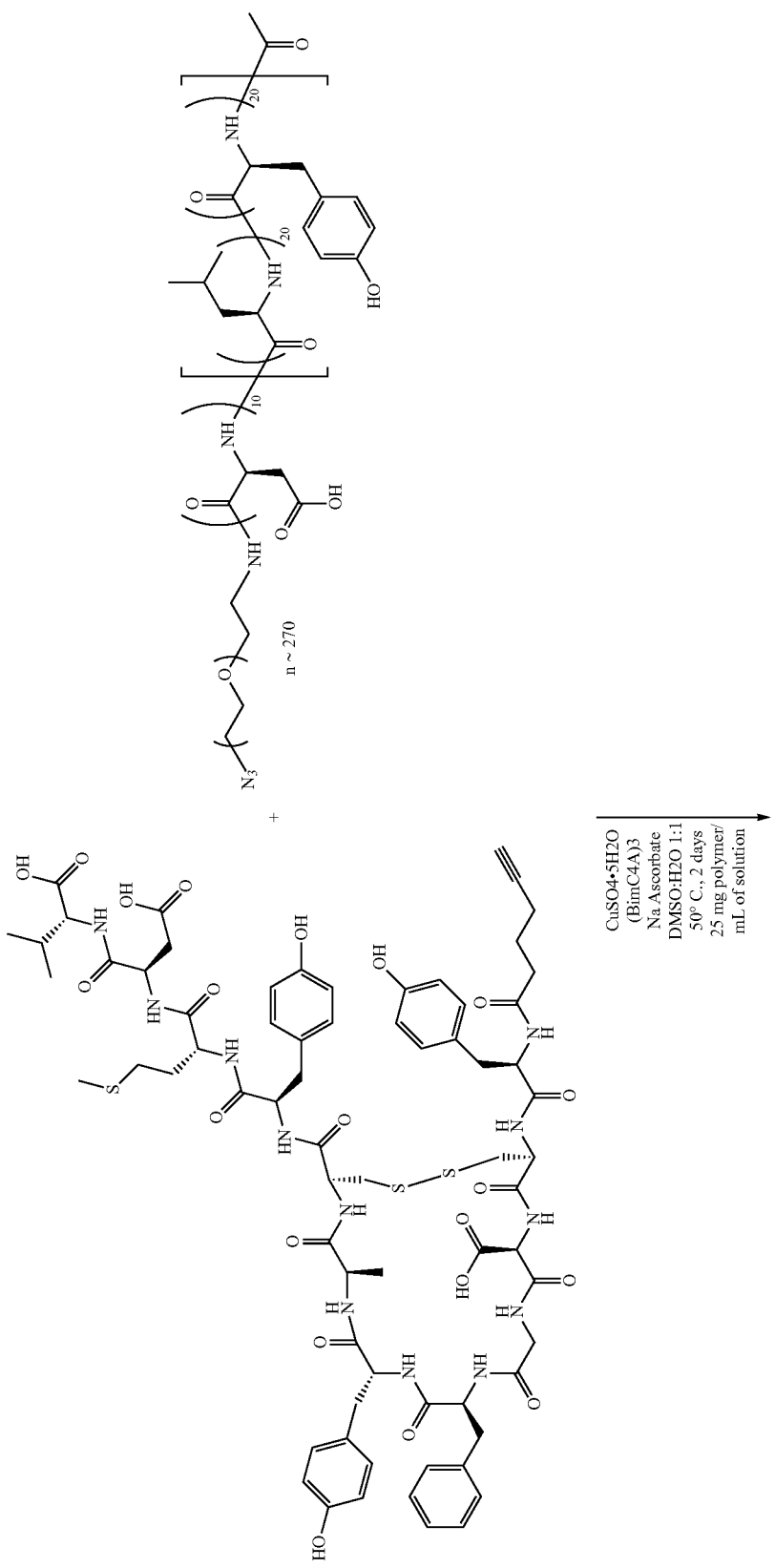

-continued
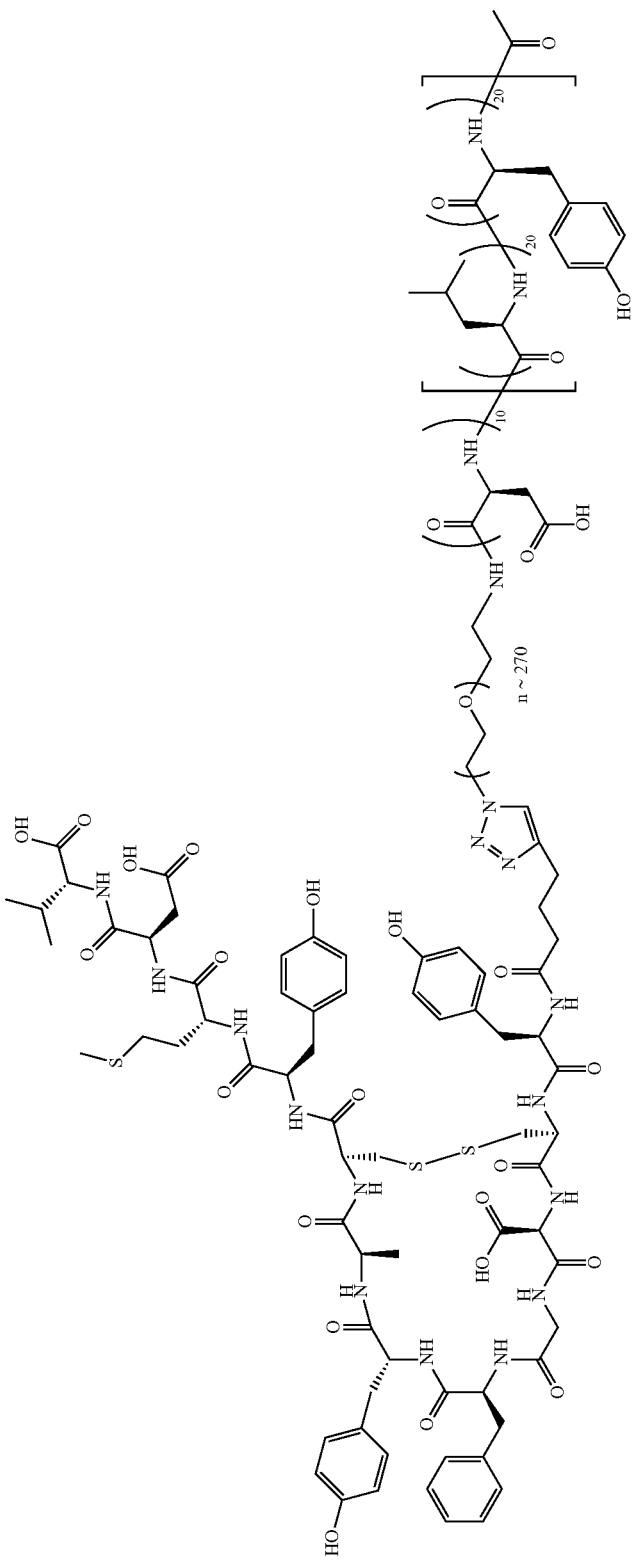

Example 20

Click of HER2Fantin-Alkyne onto $N_3$-EO270-b-Poly(Asp(His)$_{10}$)-b-Poly(dLeu$_{20}$-co-Tyr(OBzl)$_{20}$)-Ac

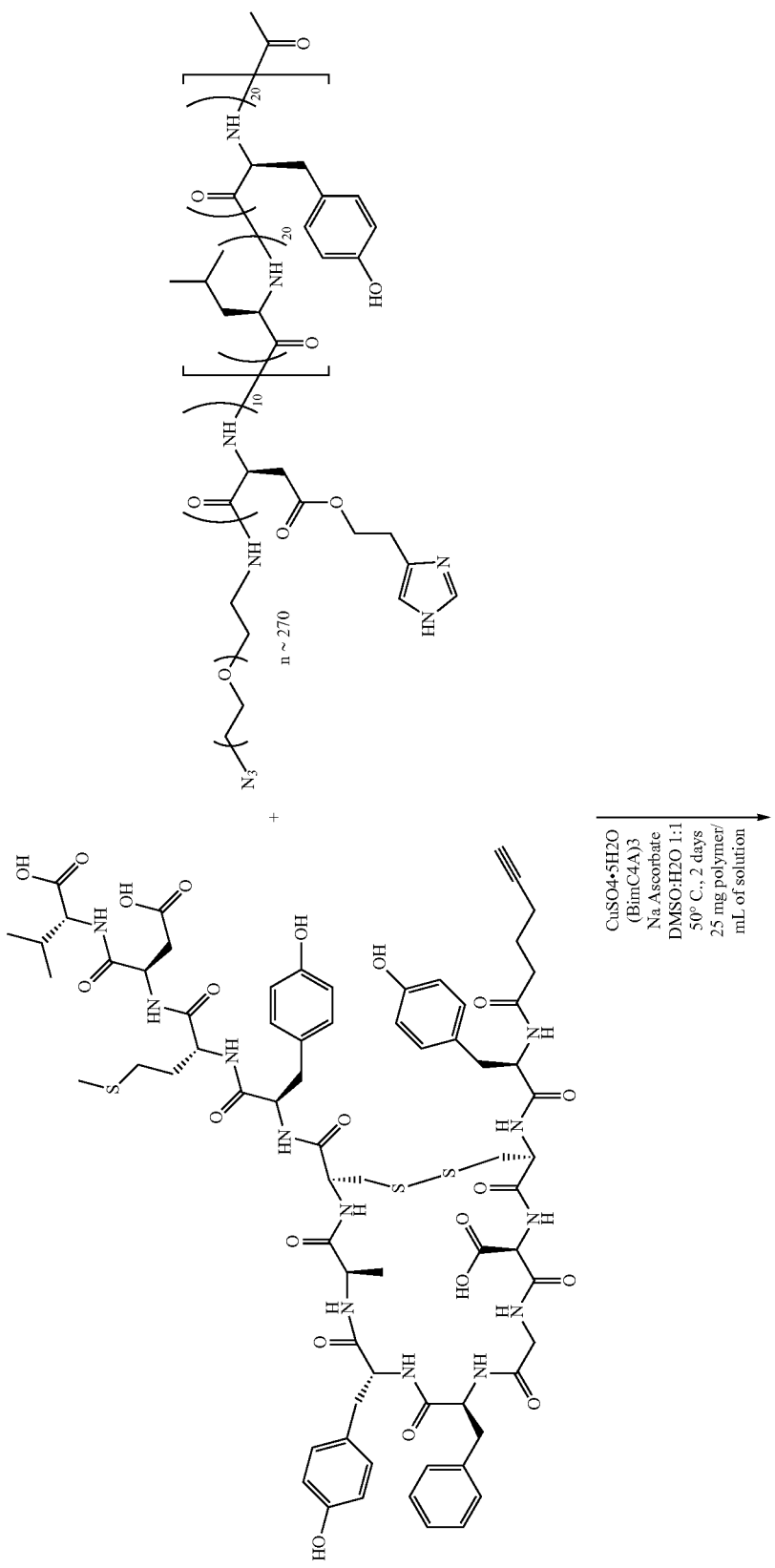

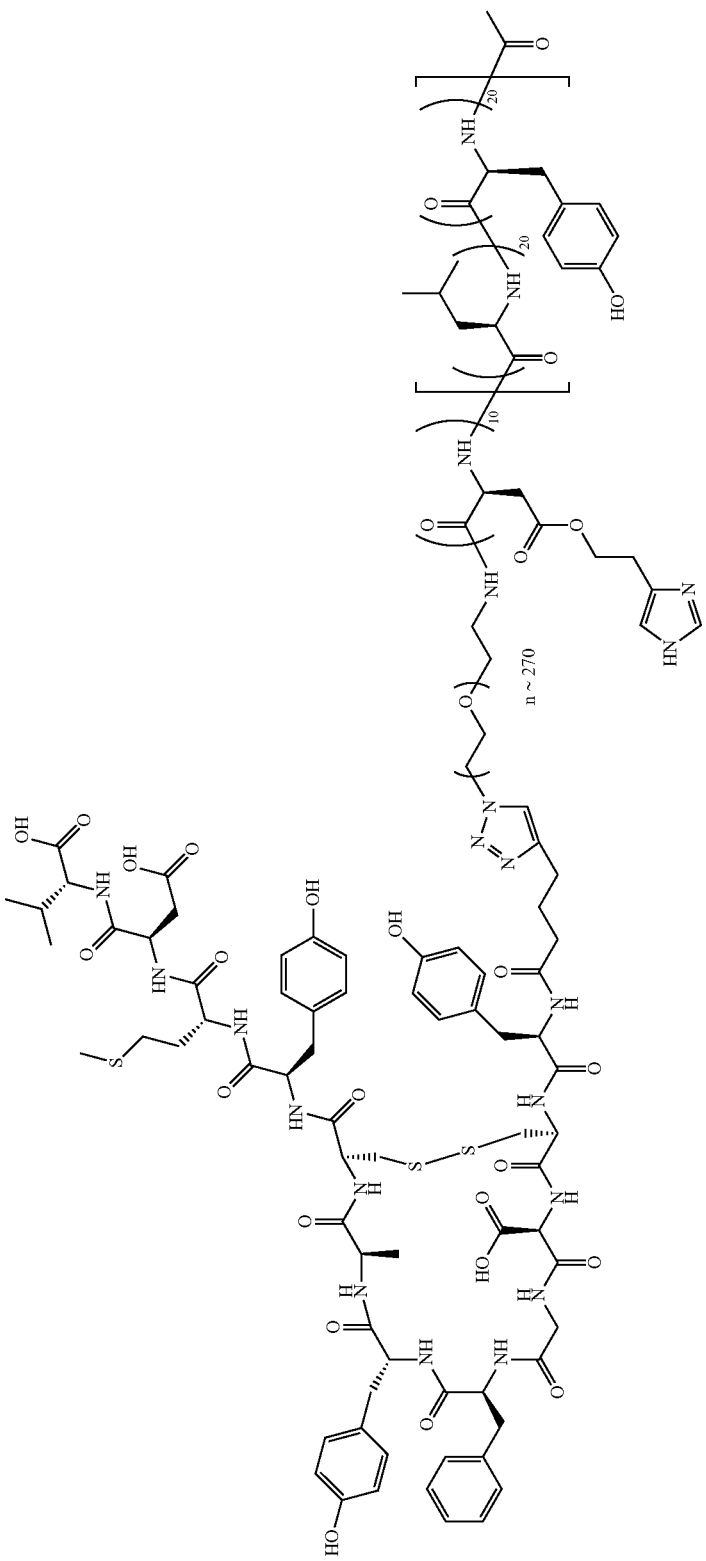

Example 21

Click of HER 2-Alkyne onto $N_3$-EO270-b-Poly(Asp(OBu)$_{10}$)-b-Poly(dLeu$_{20}$-co-Tyr(OBzl)$_{20}$)-Ac

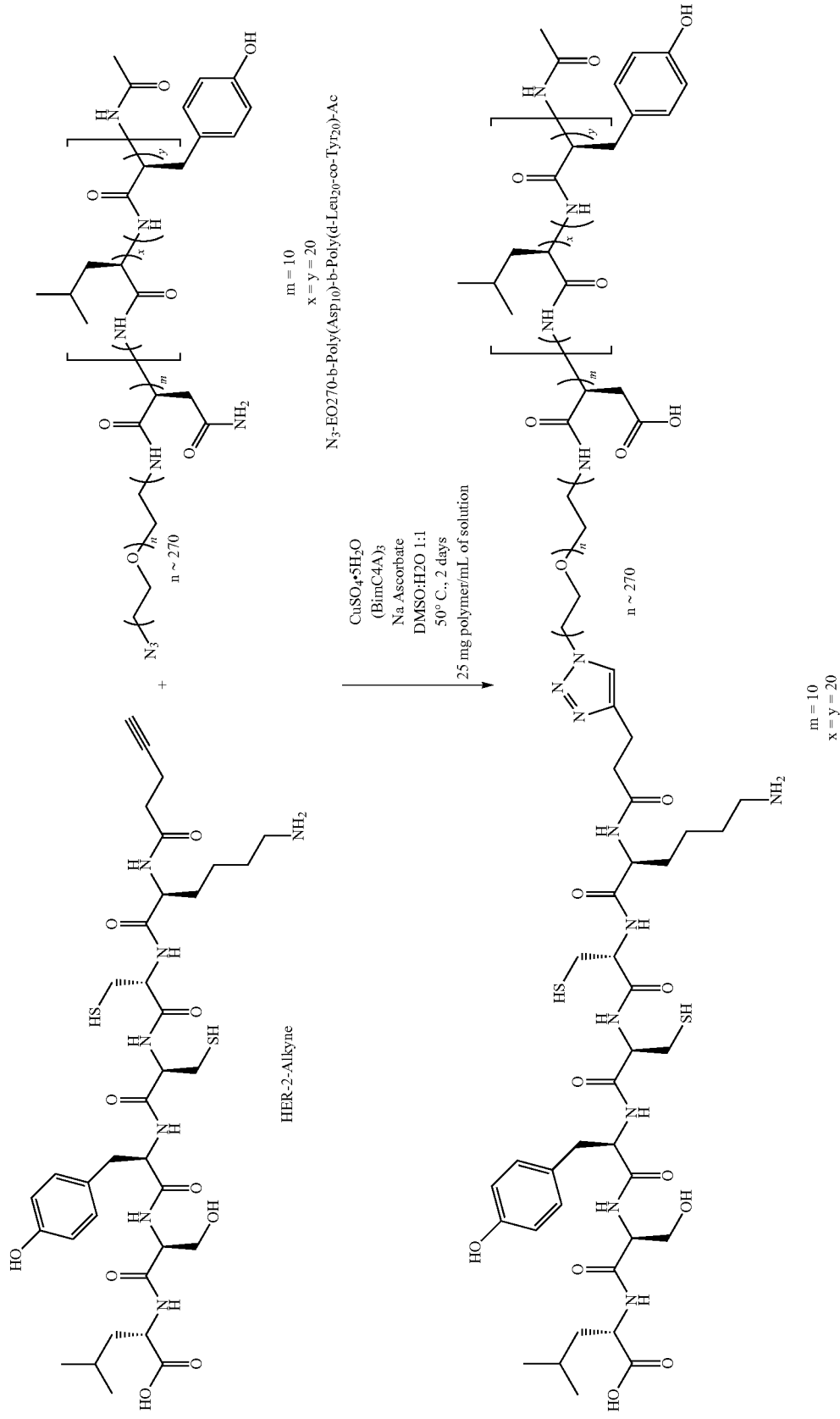

N$_3$-EO270-b-Poly(Asp(OBu)$_{10}$)-b-Poly(dLeu$_{20}$-co-Tyr (OBzl)$_{20}$)-Ac (299.3 mg, 16 µmol), HER 2-Alkyne (26.2 mg, 32.9 µmol), sodium ascorbate (79.8 mg, 0.402 mmol), (BimC4A)$_3$ (23.13 mg, 32.6 µmol), CuSO4.5H$_2$O (3.94 mg, 15.8 µmol), DMSO (6 mL) and water (6 mL) were added into a 20 mL vial, capped and stirred for 48 hr at 50° C. The light brown solution was dialyzed (3500 MWCO bag) 3 times against DI water with EDTA (15 g/L) and 2 times against DI water. The solution was freeze-dried and an off-white powder was obtained. (300 mg, 96% yield). $^1$H NMR (D$_2$O) δ 7.28-6.49, 4.66-4.40, 3.97-3.46, 2.77-2.52 ppm.

Example 22

CMC Determination

The CMC of micelles prepared from block copolymers, as described above, were determined using the method described by Eisnberg. (Astafieva, I.; Zhong, X. F.; Eisenberg, A. "Critical Micellization Phenomena in Block Copolymer Polyelectrolyte Solutions" *Macromolecules* 1993, 26, 7339-7352.) To perform these experiments, a constant concentration of pyrene ($5\times10^{-7}$ M) was equilibrated with varying concentrations of block copolymer (ca. $2\times10^2$-$1\times10^{-4}$ mg/mL) in phosphate buffered saline at room temperature for 16 hours. Excitation spectra (recorded on a Perkin Elmer LS-55 spectrophotometer with excitation between 328 and 342 nm, emission at 390 nm, 2.5 nm slit width, 15 nm/min scan speed) were recorded for each polymer concentration and the fluorescence intensities recorded at 333 and 338 nm. Eisenberg has shown that the vibrational fine structure of pyrene is highly sensitive to the polarity of its environment. Specifically, the (0,0) excitation band of pyrene will shift from 333 nm in an aqueous environment to 338.5 nm in a hydrophobic environment. The ratio of peak intensities ($I_{338}/I_{333}$) reveals the hydrophobicity of the environment surrounding the pyrene. Values of ~2.0 correspond to a hydrophobic environment such as polystyrene or poly(benzyl glutamate), whereas values of ~0.35 correspond to an aqueous environment. Plotting this ratio vs. log of the block copolymer concentration allows for the graphical interpretation of the CMC value. A more quantitative number can be obtained by fitting a logarithmic (y=a ln(x)+b) regression to the data points between the two plateaus (at ~2 and ~0.35). The CMC can be found by setting y=0.35 and solving for x (concentration in mg/mL).

Example 23

Preparation of Dox Loaded Micelles

N$_3$-EO270-b-Poly(Asp$_{10}$)-b-Poly(dLeu$_{20}$-co-Tyr$_{20}$)-Ac (524 mg) (From Example 11) and water (300 mL) was added to a 1 L beaker and stirred until a homogeneous solution was present. Doxorubicin hydrochloride (62 mg) was suspended in triethylamine (60 uL) and dichloromethane (10 mL). The resulting doxorubicin suspension was added dropwise to the rapidly stirring aqueous solution. The resulting solution was covered with foil and allowed to stir for an additional eight hours. Over this period of time, a color change from purple to red was noted. The solution was filtered through a 0.22 µm filter and then lyophilized to give 577 mg (93% yield) as a red powder.

Example 24

Crosslinking of DOX Loaded Micelles

Dox loaded micelles (30 mg) from Example 23 was dissolved in 20 mM Tris buffer (pH 7.4) supplemented with 5 mM zinc chloride (1 mL). The samples were stirred overnight then used as-is.

Example 25

Polymer Cytotoxicity

HUVEC cells were plated in 96-well plates in growth medium (F12K medium, 10% FBS, 0.1 mg/mL heparin, 0.03 mg/mL endothelial growth supplement, 2 mM L-Glutamine, 100 units/mL Pen/Strep solution). Polymer from Example 11 was dissolved at 50 mg/mL concentration and filtered through a 0.22 µm PES syringe filter. The following day, the polymer was diluted in HUVEC growth medium at the indicated concentrations and cells were treated for 72 hours without changing the media. Cell viability was assessed using the Cell-Titer Glo assay (Promega). Cells were treated in triplicate. Cell viability curves are shown in FIG. 1.

Example 26

Polymer Cytotoxicity

HUVEC cells were plated in 96-well plates in growth medium (F12K medium, 10% FBS, 0.1 mg/mL heparin, 0.03 mg/mL endothelial growth supplement, 2 mM L-Glutamine, 100 units/mL Pen/Strep solution). Polymer from Example 14 was dissolved at 50 mg/mL concentration and filtered through a 0.22 µm PES syringe filter. The following day, the polymer was diluted in HUVEC growth medium at the indicated concentrations and cells were treated for 72 hours without changing the media. Cell viability was assessed using the Cell-Titer Glo assay (Promega). Cells were treated in triplicate. Cell viability curve is shown in FIG. 2.

Example 27

Gel Electrophoresis of Crosslinked DOX Loaded Micelles

DOX loaded micelles (Example 20) or crosslinked Dox loaded micelles (Example 21) were prepared at a stock concentration of 20 mg/mL of doxorubicin in either 20 mM or 50 mM Tris at pH 7.5. Samples were diluted to 1 mg/mL doxorubicin concentration and 50 µg of doxorubicin was resolved in a 2% agarose gel in 200 mM Tris buffer, pH 9.0. Dox migration was toward the anode. The data shown in FIG. 3 exhibits reduced migration of doxorubicin in crosslinked micelles.

Example 28

Cytotoxicity Assay

MCF-7 cells were maintained in RPMI 1640 medium supplemented with 10% FBS, 2 mM L-Glutamine, and 100 units/mL of penicillin and streptomycin. MDA-MB-453 cells were maintained in DMEM supplemented with 10% FBS, 2 mM L-Glutamine, and 100 units/mL of penicillin and streptomycin. Cells were plated in 96-well white-walled plates at a concentration of $1.5$-$2.0\times10^4$ cells per well. The following day, cells were treated with 5 μM of free doxorubicin or doxorubicin loaded micelles (Example 20, IT-143 uncrosslinked) or crosslinked doxorubicin loaded micelles (Example 21, IT-143 crosslinked) for 24, 48, or 72 hours. At each timepoint, cell viability was determined using the Cell-Titer Glo assay (Promega). Cells were treated in triplicate and data is shown in FIG. 4 and FIG. 5.

Example 29

Pharmacokinetics of Crosslinked DOX Loaded Micelles

Athymic nude mice were injected with 15 mg/kg of either doxorubicin, crosslinked dox loaded micelles (IT-143, Example 24), or dox loaded micelles (Example 23) by a fast IV bolus into the tail vein with an injection volume of 0.2-0.4 mL. The delivery vehicle for drug administration was isotonic saline. Mouse blood was collected from mice into $K_2$-EDTA tubes by heart puncture at time points of 5 minutes, 15 minutes, 1 hour, and 4 hours. Plasma was isolated by centrifugation at 1000 RPM for 5 minutes, and 150 uL of extraction solution (ice cold methanol/100 ng/mL daunorubicin internal standard) was added to 50 uL of each plasma sample. Samples are then vortexed for 10 minutes, centrifuged at 13,000 RPM for 10 minutes, and 150 uL of the supernatant is transferred to HPLC vials for analysis.

Samples were analyzed on a Waters Alliance 2695 equipped with a 2475 fluorescence detector (Ex=470 nm; Em=580). A 5 μL sample injection was made onto a Waters 4 μm Nova Pak C18 (3.9×150 mm) at 30° C. with a flow rate of 0.750 mL per minute of 10 mM phosphate buffer (pH=1.4), methanol and acetonitrile (gradient from 70/10/20 to 40/10/50 for buffer/methanol/acetonitrile was made over eight minutes). Analyte eluted at 5.9 minutes under these conditions, was normalized to the internal standard, and quantitated using a standard curve comprised of seven standards. The pharmacokinetic parameters are summarized in the table below and the curves are shown in FIG. 6.

| Sample | Cmax (ug/mL) | AUC (ug * hr/mL) | $T^{1/2}$ (h) |
|---|---|---|---|
| Crosslinked Dox Micelle | 18.08 | 21.5 | 1.4 |
| Uncrosslinked Dox Micelle | 0.59 | 1.3 | 5.6 |
| Free Dox | 0.21 | 0.2 | 5.4 |

Example 30

Crosslinking of DOX Loaded Micelles

Dox loaded micelles (569.55 mg) from Example 23 was dissolved in 20 mM Tris buffer (pH 7.4) supplemented with 5 mM zinc chloride (25 mL). Once a homogeneous solution was present, the pH was adjusted to 7.5 with 1 N NaOH, then stirred overnight. The samples were used as-is for further experiments.

Example 31

Pharmacokinetics of Crosslinked DOX Loaded Micelles

Athymic nude mice were injected with 15 mg/kg of crosslinked dox loaded micelles (IT-143, Example 30 by a fast IV bolus into the tail vein with an injection volume of 0.4 mL. The delivery vehicle for drug administration was isotonic saline. Mouse blood was collected from mice into $K_2$-EDTA tubes by heart puncture at time points of 5 minutes, 15 minutes, 1 hour, and 4 hours. Plasma was isolated by centrifugation at 1000 RPM for 5 minutes, and 150 uL of extraction solution (ice cold methanol/100 ng/mL daunorubicin internal standard) was added to 50 uL of each plasma sample. Samples are then vortexed for 10 minutes, centrifuged at 13,000 RPM for 10 minutes, and 150 uL of the supernatant is transferred to HPLC vials for analysis.

Samples were analyzed on a Waters Alliance 2695 equipped with a 2475 fluorescence detector (Ex=470 nm; Em=580). A 5 μL sample injection was made onto a Waters 4 μm Nova Pak C18 (3.9×150 mm) at 30° C. with a flow rate of 0.750 mL per minute of 10 mM phosphate buffer (pH=1.4), methanol and acetonitrile (gradient from 70/10/20 to 40/10/50 for buffer/methanol/acetonitrile was made over eight minutes). Analyte eluted at 5.9 minutes under these conditions, was normalized to the internal standard, and quantitated using a standard curve comprised of seven standards. The pharmacokinetic parameters are summarized in the table below and the curves are shown in FIG. 7.

| Sample | Cmax (ug/mL) | AUC (ug * hr/mL) | $T^{1/2}$ (h) |
|---|---|---|---|
| IT-143 (Example 30) | 45.50 | 27.48 | 0.9 |

Example 32

Iron (III) Crosslinking of DOX Loaded Micelles

Dox loaded micelles (100 mg) (prepared as in Example 23) was dissolved in 20 mM Tris HCl buffer supplemented with 5 mM iron (III) chloride (4 mL). Once a homogeneous solution was present, the pH was adjusted to 8.0 with 1 N NaOH, then stirred overnight. The samples were lyophilized and the reddish-brown powder stored at 4° C.

Example 33

Stability of Iron (III) Crosslinked, DOX Loaded Micelles

Dox loaded micelles (prepared as in Example 23) was dissolved in 20 mM Tris, pH 7.5 with varying concentrations (0, 0.1, 1, 5, and 10 mM) of $FeCl_3$. Samples dissolved such that the final concentration of formulation was 25 mg/mL in the buffer. The pH of the samples was adjusted to 8.0 with 1 N NaOH, followed by overnight incubation at room temperature. Samples were diluted to 0.25 mg/mL polymer concentration with 10 mM pH 8 phosphate buffer, placed in a dialysis bag (Spectra Por 7, 3500 molecular weight cut off) and dialyzed for 6 hours against 10 mM pH 8 phosphate buffer. An aliquot before and after dialysis was analyzed by HPLC to determine the concentration of doxorubicin in each sample. FIG. 8 displays the percent of doxorubicin remaining in the dialysis bag compared to pre-dialysis samples as a function of iron (III) chloride concentration. A 10-fold increase in doxorubicin retention is observed for 5 and 10 mM of iron (III) chloride when compared to the sample with no iron added, indicating that crosslinking was achieved.

Example 34

Crosslinking Optimization with Iron (III) Chloride

Dox loaded micelles (10 mg) (prepared as in Example 23) were dissolved in 20 mM Tris HCl buffer supplemented with 5 mM iron (III) chloride (0.4 mL). Once homogeneous, the samples were adjusted to various pH values (native, 5.5, 6, 6.5, 7, 7.5, or 8) followed by overnight incubation. Samples were diluted to 0.25 mg/mL polymer concentration with 10 mM pH 8 phosphate buffer, placed in a dialysis bag (Spectra Por 7, 3500 molecular weight cut off) and dialyzed for 6 hours against 10 mM pH 8 phosphate buffer. An aliquot before and after dialysis was analyzed by HPLC to determine the concentration of doxorubicin in each sample. FIG. 9 displays the percent of doxorubicin remaining in the dialysis bag compared to pre-dialysis samples as a function of iron (III) chloride concentration. The data demonstrate that adjustment to pH 8.0 yielded the highest crosslinking efficiency.

Example 35

Crosslinking Kinetics with Iron (III) Chloride

Dox loaded micelles (10 mg) (prepared as in Example 23) were dissolved in 20 mM Tris HCl buffer supplemented with 5 mM iron (III) chloride (0.4 mL). Once homogeneous, the solution was adjusted to pH 8 with 1 N NaOH. Aliquots were removed from the solution at various time points after pH adjustment (2, 4, 6, 8, 12, 16, and 24 h) then diluted to 0.25 mg/mL polymer concentration with 10 mM pH 8 phosphate buffer, placed in a dialysis bag (Spectra Por 7, 3500 molecular weight cut off) and dialyzed for 6 hours against 10 mM pH 8 phosphate buffer. An aliquot before and after dialysis was analyzed by HPLC to determine the concentration of doxorubicin in each sample. FIG. 10 shows the kinetic dependence upon the crosslinking reaction with iron (III) chloride.

Example 36 pH Dependent Release from Iron (III) Crosslinked Micelles

Dox loaded micelles (prepared as in Example 23) was dissolved in 20 mM Tris, pH 7.5 with concentrations of 0, 5 and 10 mM of $FeCl_3$. Samples dissolved such that the final concentration of formulation was 25 mg/mL in the buffer. The pH of the samples was adjusted to 8.0 with 1 N NaOH, followed by overnight incubation at room temperature. Seven aliquots (50 µL) of each stock solution were then diluted into seven separate 10 mM phosphate buffer (5 mL) at pH 3, 4, 5, 6, 7, 7.4 and 8, giving a final concentration of 0.2 mg formulation per mL buffer. 3 mL of each sample was added to a Spectra-Por 3500 MWCO dialysis bag, then placed in a 400 mL beaker containing a stir bar and 300 mL of the corresponding 10 mM phosphate buffer. The samples were allowed to dialyze for 6 hours, then the samples removed from the dialysis bag. Samples pre and post dialysis were analyzed by HPLC to determine the doxorubicin concentration in each sample. FIG. 11 shows the pH dependent release of each sample. The data shows that the samples containing iron demonstrate improved retention of doxorubicin at high pH values, but release of the drug at low pH values.

Example 37

Crosslinking Optimization with Iron (II) and Iron (III) Chloride

Dox loaded micelles (prepared as in Example 23) was dissolved in 20 mM Tris, pH 7.5 with varying concentrations (0, 1, 2, 3, 4, and 5 mM) of $FeCl_2$ and $FeCl_3$. Samples dissolved such that the final concentration of formulation was 25 mg/mL in the buffer. The pH of the samples was adjusted to 8.0 with 1 N NaOH, followed by overnight incubation at room temperature. Samples were diluted to 0.25 mg/mL polymer concentration with 10 mM pH 8 phosphate buffer, placed in a dialysis bag (Spectra Por 7, 3500 molecular weight cut off) and dialyzed for 6 hours against 10 mM pH 8 phosphate buffer. An aliquot before and after dialysis was analyzed by HPLC to determine the concentration of doxorubicin in each sample. FIG. 12 displays the percent of doxorubicin remaining in the dialysis bag compared to pre-dialysis samples as a function of iron concentration. The data demonstrate effective crosslinking using either $FeCl_3$ or $FeCl_2$.

Example 38 pH Dependent Release from Iron (III) Crosslinked Micelles

Dox loaded micelles (prepared as in Example 23) was dissolved in 20 mM Tris, pH 7.5 with concentrations of 1, and 4 mM of $FeCl_2$ and 4 mM of $FeCl_3$. Samples dissolved such that the final concentration of formulation was 25 mg/mL in the buffer. The pH of the samples was adjusted to 8.0 with 1 N NaOH, followed by overnight incubation at room temperature. Seven aliquots (50 µL) of each stock solution were then diluted into seven separate 10 mM phosphate buffer (5 mL) at pH 3, 4, 5, 6, 7, 7.4 and 8, giving a final concentration of 0.2 mg formulation per mL buffer. 3 mL of each sample was added to a Spectra-Por 3500 MWCO dialysis bag, then placed in a 400 mL beaker containing a stir bar and 300 mL of the corresponding 10 mM phosphate buffer. The samples were allowed to dialyze for 6 hours, then the samples removed from the dialysis bag. Samples pre and post dialysis were analyzed by HPLC to determine the doxorubicin concentration in each sample. FIG. 13 shows the pH dependent release of each sample. The data demonstrates that the pH dependent release is present for crosslinking performed with iron (II) chloride, and can also be slightly tuned by the varying the addition of iron during the crosslinking step.

Example 39

Pharmacokinetics of Iron Crosslinked DOX Loaded Micelles

Fisher rats that possessed a jugular vein catheter were injected with 10 mg/kg of free doxorubicin, uncrosslinked micelles (prepared according to Example 23), and iron (III) crosslinked dox loaded micelles (Example 32) by a fast IV bolus with an injection volume of 1 mL. The delivery vehicle for drug administration was isotonic saline. Rat blood was collected from the catheter into $K_2$-EDTA tubes by heart puncture at time points of 1, minute, 5 minutes, 15 minutes, 1 hour, 4 hours, 8 hours and 24 hours. Plasma was isolated by centrifugation at 1000 RPM for 5 minutes, and 150 uL of extraction solution (ice cold methanol/100 ng/mL daunorubicin internal standard) was added to 50 uL of each plasma sample. Samples were then vortexed for 10 minutes, centrifuged at 13,000 RPM for 10 minutes, and 150 uL of the supernatant is transferred to HPLC vials for analysis.

Samples were analyzed on a Waters Alliance 2695 equipped with a 2475 fluorescence detector (Ex=470 nm; Em=580). A 5 μL sample injection was made onto a Waters 4 μm Nova Pak C18 (3.9×150 mm) at 30° C. with a flow rate of 0.750 mL per minute of 10 mM phosphate buffer (pH=1.4), methanol and acetonitrile (gradient from 70/10/20 to 40/10/50 for buffer/methanol/acetonitrile was made over eight minutes). Analyte eluted at 5.9 minutes under these conditions, was normalized to the internal standard, and quantitated using a standard curve comprised of seven standards. The pharmacokinetic parameters are summarized in the table below and the curves are shown in FIG. 14. It is important to note that the AUC is nearly 15 times great for the iron (III) crosslinked micelle when compared to the uncrosslinked micelle, again, indicating that the iron crosslinking is stabilizing the micelle when diluted in the bloodstream.

| Sample | Cmax (ug/mL) | AUC (ug * hr/mL) |
|---|---|---|
| Free DOX | 9.76 | 2.61 |
| Uncrosslinked Micelles | 18.18 | 7.05 |
| Iron (III) Crosslinked Micelles | 55.77 | 103.13 |

Example 40

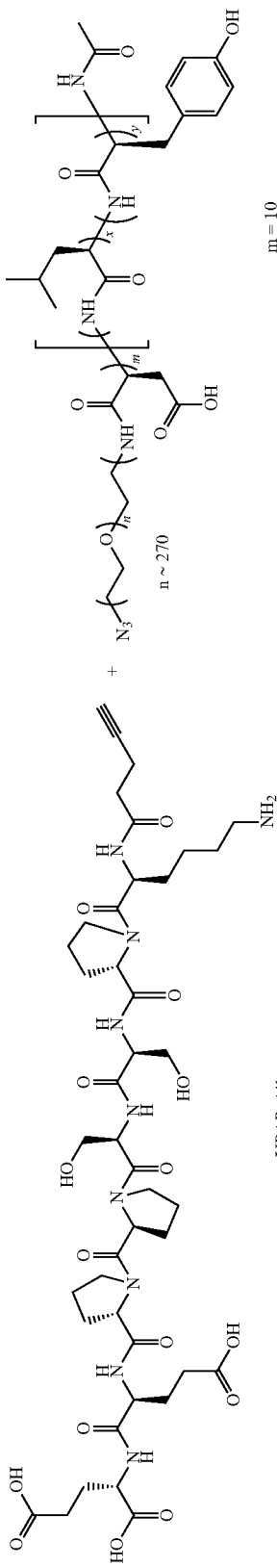
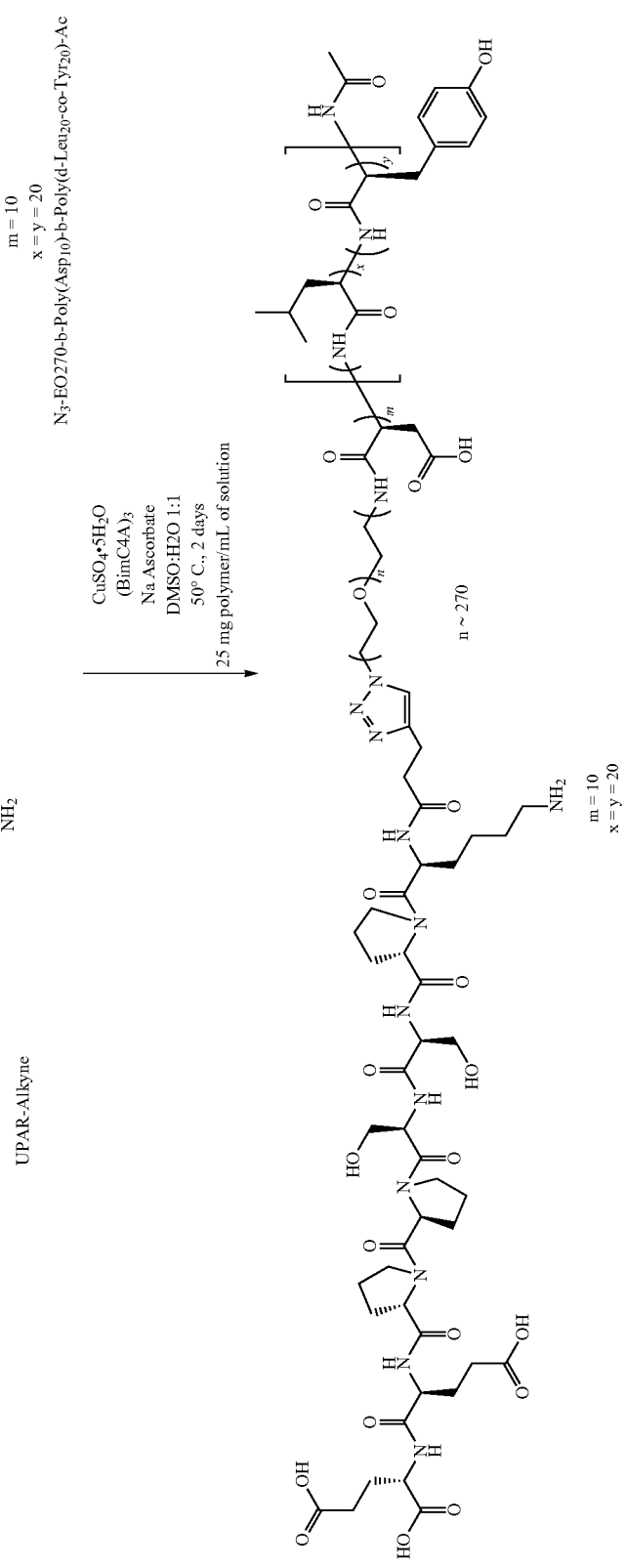

UPAR-Poly(ethylene oxide)$_{270}$-b-Poly(Asp$_{10}$)-b-Poly(dLeu$_{20}$-co-Tyr$_{20}$)-Ac N$_3$-Poly(ethylene oxide)$_{270}$-b-Poly(Asp$_{10}$)-b-Poly(dLeu$_{20}$-co-Tyr$_{20}$)-Ac (306.2 mg, 16.4 μmol) from Example 11, alkynyl-UPAR (25.0 mg, 21.1 μmol), sodium ascorbate (86.9 mg, 0.44 mmol), (BimC4A)3 (23.4 mg, 33.1 μmol), CuSO$_4$.5H$_2$O (5.44 mg, 21.8 μmol), DMSO (6 mL) and water (6 mL) were added into a 20 mL vial, capped and stirred for 48 hr at 50° C. The light brown solution was dialyzed (3500 MWCO bag) 3 times against deionized water with EDTA (15 g/L) and 2 times against deionized water. The solution was freeze-dried and the title compound was obtained as an off-white powder. (272.2 mg, 85% yield). $^1$H NMR (D$_2$O) δ 8.16 (1H), 7.84 (1H), 7.44-6.72 (4H), 4.60-4.26 (18H), 4.06-3.41 (1040H), 2.99 (6H), 2.73 (1H), 2.58-1.69 (34H).

Example 41

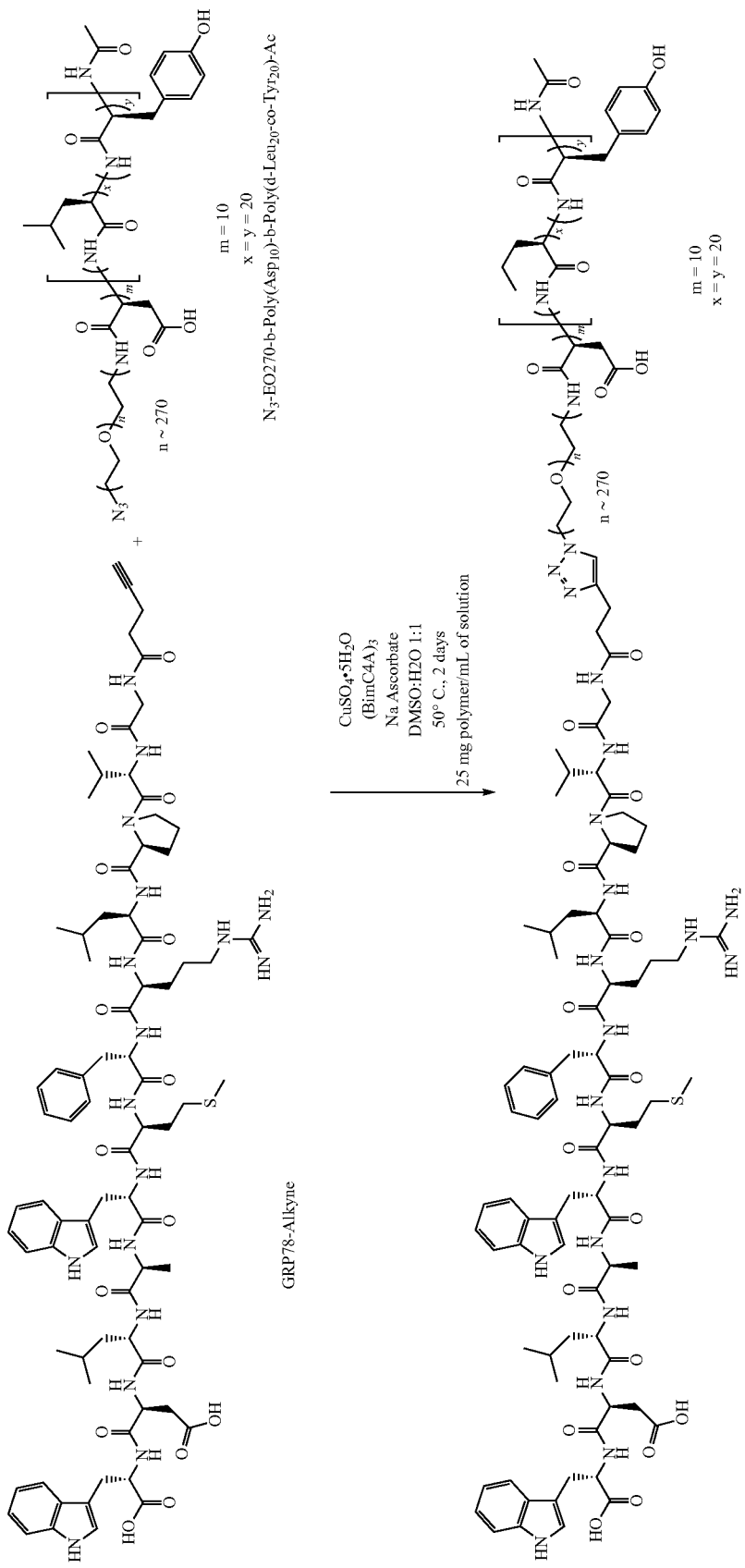

GRP78-Poly(ethylene oxide)$_{270}$-b-Poly(Asp$_{10}$)-b-Poly(dLeu$_{20}$-co-Tyr$_{20}$)-Ac N$_3$-Poly(ethylene oxide)$_{270}$-b-Poly(Asp$_{10}$)-b-Poly(dLeu$_{20}$-co-Tyr$_{20}$)-Ac (296.6 mg, 15.9 μmmol) from Example 11, alkynyl-GRP 78 (32.5 mg, 20.7 μmmol), sodium ascorbate (80.55 mg, 0.41 mmol), (BimC4A)3 (24.8 mg, 35 μmol), CuSO$_4$·5H$_2$O (5.30 mg, 21.2 μmol), DMSO (6 mL) and water (6 mL) were added into a 20 mL vial, capped and stirred for 48 hr at 50° C. The light brown solution was dialyzed (3500 MWCO bag) 3 times against DI water with EDTA (15 g/L) and 2 times against DI water. The solution was freeze-dried and an off-white powder was obtained. (244.3 mg, 92% yield). $^1$H NMR (D$_2$O) δ 8.16 (1H), 7.44-6.72 (8H), 4.35 (3H), 4.06-3.41 (1040H), 2.97-2.62 (12H).

Example 42

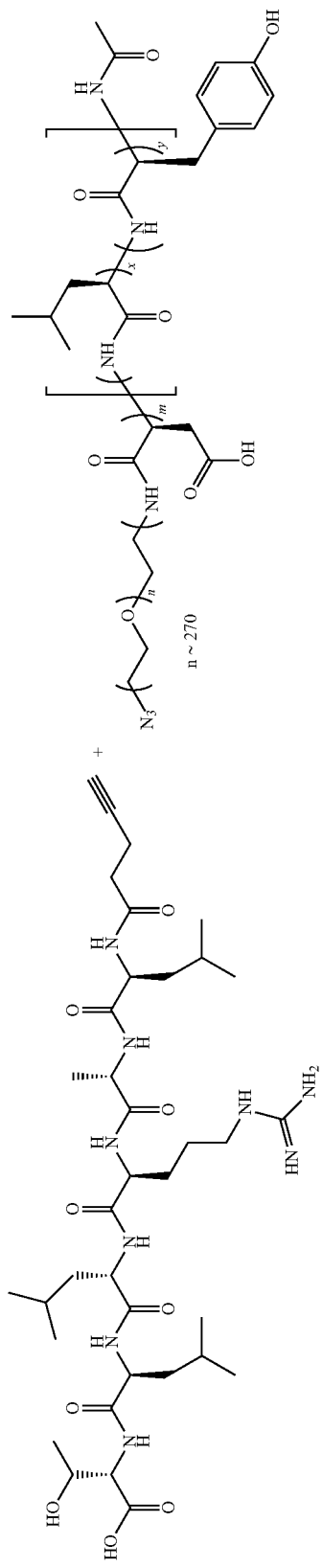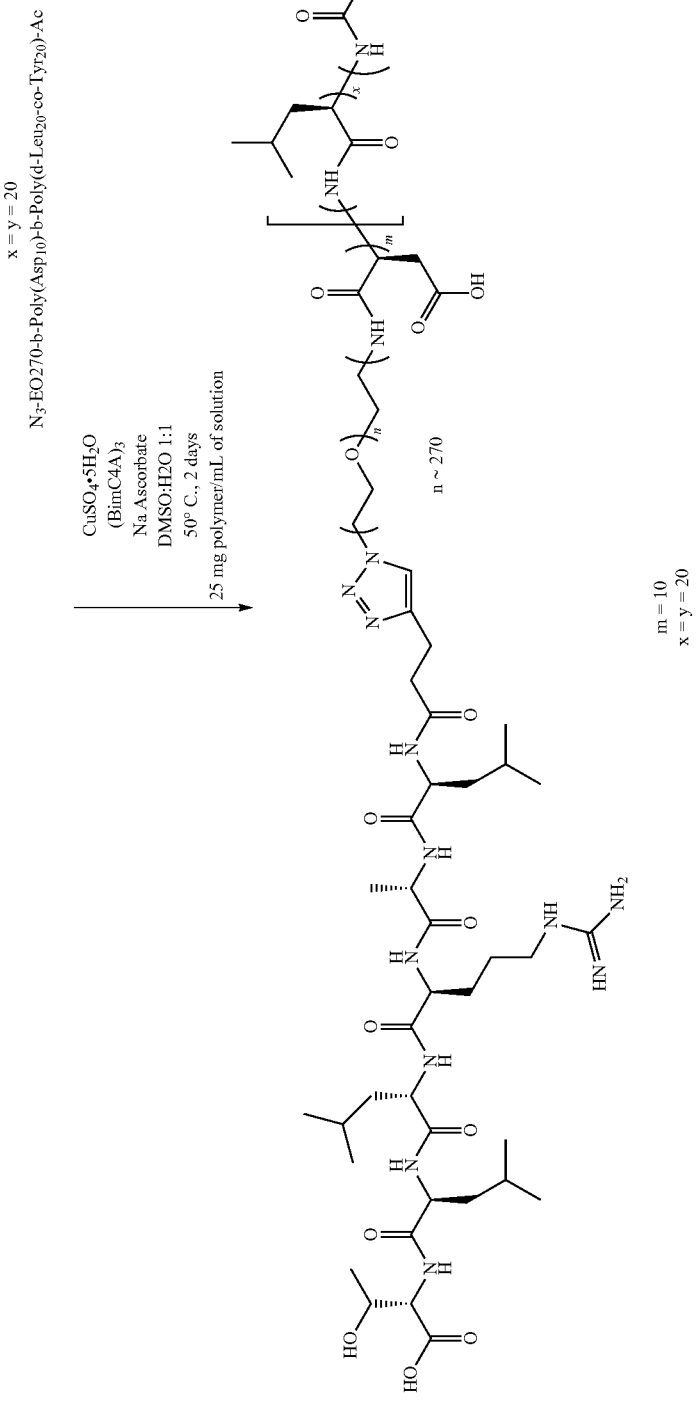

EGFR-Poly(ethylene oxide)270-b-Poly(Asp10)-b-Poly(dLeu20-co-Tyr20)-Ac

N3-Poly(ethylene oxide)$_{270}$-b-Poly(Asp$_{10}$)-b-Poly(dLeu$_{20}$-co-Tyr$_{20}$)-Ac (877 mg, 46 µmol) from Example 11, alkynyl-EGFR (50 mg, 56.3 µmol), sodium ascorbate (232 mg, 1.17 mmol), (BimC4A)3 (66 mg, 94 µmol), CuSO$_4$·5H$_2$O (12 mg, 47 µmol), DMSO (17 mL) and water (17 mL) were added into a 50 mL round bottom flask, capped and stirred for 48 hr at 50° C. The light brown solution was dialyzed (3500 MWCO bag) 3 times against DI water with EDTA (15 g/L) and 2 times against DI water. The solution was freeze-dried and an off-white powder was obtained. (512 mg, 56% yield). $^1$H NMR (D$_2$O) δ 8.16, 7.09, 6.82, 4.35, 4.06-3.41 (1040H), 3.27-2.73 (14H).

Example 43

Preparation of EGFR Targeted, DOX Loaded Micelles

N$_3$-EO270-b-Poly(Asp$_{10}$)-b-Poly(dLeu$_{20}$-co-Tyr$_{20}$)-Ac (97.5 mg) (Example 11) and EGFR-Poly(ethylene oxide)$_{270}$-b-Poly(Asp$_{10}$)-b-Poly(dLeu$_{20}$-co-Tyr$_{20}$)-Ac (Example 42) was dissolved in water (65 mL) and stirred until homogeneous. Doxorubicin hydrochloride (10 mg) was suspended in a 80% dichloromethane/20% methanol solution (3.9 mL), followed by the addition of triethylamine (11 uL). The resulting doxorubicin suspension was added dropwise to the rapidly stirring aqueous solution. The resulting solution was covered with foil and allowed to stir for an additional eight hours. Over this period of time, a color change from purple to red was noted. The solution was filtered through a 0.22 µm filter and then lyophilized to give 92 mg (84% yield) as a red powder.

Example 44

Preparation of uPAR Targeted, DOX Loaded Micelles

N$_3$-EO270-b-Poly(Asp$_{10}$)-b-Poly(dLeu$_{20}$-co-Tyr$_{20}$)-Ac (97.5 mg) (Example 11) and uPAR-Poly(ethylene oxide)$_{270}$-b-Poly(Asp$_{10}$)-b-Poly(dLeu$_{20}$-co-Tyr$_{20}$)-Ac (Example 40) was dissolved in water (65 mL) and stirred until homogeneous. Doxorubicin hydrochloride (10 mg) was suspended in a 80% dichloromethane/20% methanol solution (3.9 mL), followed by the addition of triethylamine (11 uL). The resulting doxorubicin suspension was added dropwise to the rapidly stirring aqueous solution. The resulting solution was covered with foil and allowed to stir for an additional eight hours. Over this period of time, a color change from purple to red was noted. The solution was filtered through a 0.22 µm filter and then lyophilized to give 96 mg (87% yield) as a red powder.

Example 45

Iron (II) Crosslinking of EGFR Targeted, DOX Loaded Micelles

EGFR targeted, Dox loaded micelles (20 mg) (Example 43) was dissolved in 20 mM Tris HCl buffer supplemented with 1 mM iron (II) chloride (1 mL). Once a homogeneous solution was present, the pH was adjusted to 8.0 with 1 N NaOH, then stirred overnight. The samples were lyophilized and the reddish-brown powder stored at 4° C.

Example 46

Iron (II) Crosslinking of uPAR Targeted, DOX Loaded Micelles uPAR targeted, Dox loaded micelles (20 mg) (Example 44) was dissolved in 20 mM Tris HCl buffer supplemented with 1 mM iron (II) chloride (1 mL). Once a homogeneous solution was present, the pH was adjusted to 8.0 with 1 N NaOH, then stirred overnight. The samples were lyophilized and the reddish-brown powder stored at 4° C.

Example 47 pH Dependent Release from Targeted, Iron (II) Crosslinked Micelles

Dox loaded micelles (prepared as in Example 23, 43, and 44) were dissolved in 20 mM Tris, pH 7.5 with 1 mM of FeCl$_2$. Samples dissolved such that the final concentration of formulation was 25 mg/mL in the buffer. The pH of the samples was adjusted to 8.0 with 1 N NaOH, followed by overnight incubation at room temperature. Seven aliquots (50 µL) of each stock solution were then diluted into seven separate 10 mM phosphate buffer (5 mL) at pH 3, 4, 5, 6, 7, 7.4 and 8, giving a final concentration of 0.2 mg formulation per mL buffer. 3 mL of each sample was added to a Spectra-Por 3500 MWCO dialysis bag, then placed in a 400 mL beaker containing a stir bar and 300 mL of the corresponding 10 mM phosphate buffer. The samples were allowed to dialyze for 6 hours, then the samples removed from the dialysis bag. Samples pre and post dialysis were analyzed by HPLC to determine the doxorubicin concentration in each sample. FIG. 15 shows the pH dependent release of each sample. It is important to note that the pH dependent release of the crosslinked micelles does not change with the addition of targeting groups.

Example 48

Pulse-Treatment Cytotoxicity Assay

A549 cells were maintained in F12K medium supplemented with 10% FBS, 2 mM L-Glutamine, and 100 units/mL of penicillin and streptomycin. Cells were plated in 96-well white-walled plates at a concentration of 5.0×10$^3$ cells per well. The following day, cells were treated with increasing concentrations of free doxorubicin, iron (II) crosslinked micelles (Example 37), EGFR targeted, iron (II) crosslinked micelles (Example 45), or uPAR targeted, iron (II) crosslinked micelles (Example 46) for 1.5 hours. After this time, cells were washed with PBS, fresh growth medium was added and cells were incubated for an additional 72 hours. Cell viability was then determined using the Cell-Titer Glo assay (Promega). Cells were treated in triplicate. FIG. 16 shows the in vitro cytotoxicity of the four samples in A549 cells, whereas FIG. 17 shows results in 8505C cells. It should be noted that the targeted, crosslinked micelles exhibit a much lower IC$_{50}$ than the untargeted and free doxorubicin.

Example 49

Continuous Cytotoxicity Assay with Iron (II) Doxorubicin Micelles

Caki-1 cells were maintained in McCoy's 5A media supplemented with 10% FBS, 2 mM L-Glutamine, and 100 units/mL of penicillin and streptomycin. MG-63 cells were maintained in RPMI 1640 media supplemented with 10% FBS, 2 mM L-Glutamine, and 100 units/mL of penicillin and streptomycin. Cells were plated in 96-well white-walled plates at a concentration of $1.0 \times 10^4$ cells (Caki-1) or $7.0 \times 10^3$ cells (MG-63) per well. The following day, cells were treated with increasing concentrations of free doxorubicin, or iron (II) crosslinked micelles (Example 37) for 72 hours. Cell viability was then determined using the Cell-Titer Glo assay (Promega). Cells were treated in triplicate. FIG. 18 shows the in vitro cytotoxicity of the four samples. It should be noted that the cytotoxicity profile of the iron (II) crosslinked doxorubicin micelle is similar to free doxorubicin.

Example 50

Preparation of Daunorubicin Loaded Micelles $N_3$-EO270-b-Poly(Asp$_{10}$)-b-Poly(dLeu$_{20}$-co-Tyr$_{20}$)-Ac (3 g) (From Example 11) and water (2 L) was added to a 4 L beaker and stirred until a homogeneous solution was present. Daunorubicin hydrochloride (301 mg) was suspended in 4:1 dichloromethane:methanol (60 mL), followed by the addition of triethylamine (82 uL). The resulting daunorubicin suspension was added dropwise to the rapidly stirring aqueous solution. The resulting solution was covered with foil and allowed to stir for an additional eight hours. The solution was filtered through a 0.22 μm filter and then lyophilized to give 2.95 g (89% yield) as a red powder.

Example 51

Crosslinking of Daunorubicin Micelle

Daunorubicin loaded micelles (Example 50) were dissolved at 25 mg/mL polymer concentration in either water or 20 mM Tris, pH 7.5 supplemented with 0, 0.5, 1, 2, 3, 4, or 5 mM FeCl$_2$. Once a homogeneous solution was present, the pH was adjusted to 8.0 with 1 N NaOH, then stirred overnight. Aliquots (50 μL) of each stock solution were then diluted in 10 mM phosphate buffer (5 mL) at pH 8, giving a final concentration of 0.25 mg formulation per mL buffer. 2 mL of each sample was added to a Spectra-Por 3500 MWCO dialysis bag, then dialyzed in 300 mL of 10 mM phosphate buffer pH 8. The samples were allowed to dialyze for 6 hours, then the samples removed from the dialysis bag. Samples pre and post dialysis were analyzed by HPLC to determine the daunorubicin concentration in each sample. FIG. 19 demonstrates that crosslinked is attainable using water or 20 mM Tris as a buffer. Furthermore, maximal crosslinking is achieved at a concentration of 2 mM iron (II) or greater.

Example 52 pH-Dependent Release of Crosslinked Daunorubicin Micelles

Daunorubicin loaded micelles (prepared as in Example 51) was dissolved in water with no iron chloride, 2 mM of FeCl$_2$ or 5 mM of FeCl$_2$. Once a homogeneous solution was present, the pH was adjusted to 8.0 with 1 N NaOH, then stirred overnight. Six aliquots (50 μL) of each stock solution were then diluted into six separate 10 mM phosphate buffer (5 mL) at pH 3, 4, 5, 6, 7, and 8, giving a final concentration of 0.25 mg formulation per mL buffer. 2 mL of each sample was added to a Spectra-Por 3500 MWCO dialysis bag, then placed in a 400 mL beaker containing a stir bar and 300 mL of the corresponding 10 mM phosphate buffer. The samples were allowed to dialyze for 6 hours, then the samples removed from the dialysis bag. Samples pre and post dialysis were analyzed by HPLC to determine the daunorubicin concentration in each sample. FIG. 20 shows the pH dependent release of each sample. The data demonstrate that the pH dependent release is present for crosslinking performed with either 2 mM or 5 mM iron (II) chloride. Although the uncrosslinked daunorubicin micelle has some stability and pH-dependent release with this assay, it is less stable than crosslinked daunorubicin micelles.

Example 53

Cytotoxicity of Daunorubicin Micelles Compared to Free Daunorubicin

All cell lines were obtained from ATCC (Manassas, Va.). Media and supplements were obtained from Cell Gro (Manassas, Va.). HT-1080 cells were maintained in Eagle's Minimum Essential Medium supplemented with 10% FBS, 2 mM L-Glutamine, 1 mM sodium pyruvate, and 100 units/mL of penicillin and streptomycin. MG-63 and 786-O cells were maintained in RPMI 1640 media supplemented with 10% FBS, 2 mM L-Glutamine, and 100 units/mL of penicillin and streptomycin. SKOV-3 cells were maintained in McCoy's 5A media with 10% FBS, 2 mM L-Glutamine, and 100 units/mL of penicillin and streptomycin. Cells were plated in 96-well white-walled plates at a concentration of $1.5 \times 10^4$ (HT-1080), $7.0 \times 10^3$ (MG-63), $1.0 \times 10^4$ (786-O), or $8.0 \times 10^3$ (SKOV-3) cells per well. The following day, cells were treated with increasing concentrations of free daunorubicin, uncrosslinked daunorubicin micelle (Example 50), 2 mM iron (II) (Example 52), or 5 mM iron (II) (Example 52) crosslinked daunorubicin micelles for 72 hours. Cell viability was then determined using the Cell-Titer Glo assay (Promega). Cells were treated in triplicate. The table below shows lists the IC50 values (in μM) of the four samples. It should be noted that the IC50 values of the daunorubicin micelles are very similar to free daunorubicin.

|  | HT-1080 | MG-63 | 786-0 | SKOV-3 |
| --- | --- | --- | --- | --- |
| Daunorubicin | 0.546 ± 0.057 | 0.231 ± 0.011 | 0.231 ± 0.011 | 0.200 ± 0.012 |
| Uncrosslinked | 0.753 ± 0.08 | 0.270 ± 0.044 | 0.306 ± 0.018 | 0.203 ± 0.021 |
| 2 mM iron (II) XL | 0.602 ± 0.041 | 0.251 ± 0.059 | 0.299 ± 0.007 | 0.193 ± 0.041 |
| 5 mM iron (II) XL | 0.655 ± 0.011 | 0.177 ± 0.026 | 0.308 ± 0.041 | 0.208 ± 0.037 |

Example 54

Rat Pharmacokinetics of Daunorubicin Micelles Compared to Free Daunorubicin

Fisher rats that possessed a jugular vein catheter were injected with 10 mg/kg of free daunorubicin, uncrosslinked daunorubicin micelle (prepared according to Example 50), and iron (II) crosslinked daunorubicin loaded micelles (Example 52) by a fast IV bolus with an injection volume of 2 mL on Day 0. The delivery vehicle for drug administration was isotonic saline. Rat blood was collected from the catheter into $K_2$-EDTA tubes by heart puncture at time points of 1, minute, 5 minutes, 15 minutes, 1 hour, 4 hours, 8 hours and 24 hours. Plasma was isolated by centrifugation at 1000 RPM for 5 minutes, and 150 uL of extraction solution (ice cold methanol/100 ng/mL daunorubicin internal standard) was added to 50 uL of each plasma sample. Samples were then vortexed for 10 minutes, centrifuged at 13,000 RPM for 10 minutes, and 150 uL of the supernatant is transferred to HPLC vials for analysis.

Samples were analyzed on a Waters Alliance 2695 equiped with a 2475 fluorescence detector (Ex=470 nm; Em=580). A 5 µL sample injection was made onto a Waters 4 µm Nova Pak C18 (3.9×150 mm) at 30° C. with a flow rate of 0.750 mL per minute of 10 mM phosphate buffer (pH=1.4), methanol and acetonitrile (gradient from 70/10/20 to 40/10/50 for buffer/methanol/acetonitrile was made over eight minutes). Analyte eluted at 5.9 minutes under these conditions, was normalized to the internal standard, and quantitated using a standard curve comprised of seven standards. The pharmacokinetic parameters are summarized in the table below and the curves are shown in FIG. 21.

| Sample | Cmax (ug/mL) | AUC (ug * hr/mL) |
| --- | --- | --- |
| Free Daunorubicin | 3.29 | 1.30 |
| Uncrosslinked Daunorubicin Micelles | 2.61 | 1.48 |
| 2 mM Iron (II) Crosslinked Micelles | 125.04 | 27.92 |
| 5 mM Iron (II) Crosslinked Micelles | 143.50 | 51.78 |

It is important to note that the AUC is nearly 18-35 times (for 2 mM and 5 mM XL, respectively) greater for the iron (II) crosslinked micelles when compared to the uncrosslinked micelle, again, indicating that the iron crosslinking is stabilizing the micelle when diluted in the bloodstream. This study was repeated, and the micelles were injected in the same rats seven days after the first injection. The pharmacokinetic results are shown in the table below, and graphed in FIG. 22.

| Sample | Cmax (ug/mL) | AUC (ug * hr/mL) |
| --- | --- | --- |
| Free Daunorubicin | 10.64 | 3.54 |
| Uncrosslinked Daunorubicin Micelles | 7.91 | 2.95 |
| 2 mM Iron (II) Crosslinked Micelles | 120.63 | 35.27 |
| 5 mM Iron (II) Crosslinked Micelles | 148.60 | 78.24 |

In the repeat experiment, the AUC of the 2 mM and 5 mM XL micelle was found to be 12-26 times greater than uncrosslinked micelle, and absolute AUC values that were higher than in the first experiment. The Cmax values for the second experiment were similar to the first experiment, with slightly higher Cmax values for free daunorubicin and uncrosslinked micelle. These data demonstrate that similar pharmacokinetic data were obtained following repeat injections of daunorubicin micelles in rats.

Example 55

ELISA Assay for Rat IgM Induction Following Multiple Administrations of Daunorubicin Micelles Plasma from the experiment described in Example 54 was used in an ELISA assay to determine the concentration of rat IgM following repeated injections of free daunorubicin and daunorubicin micelles. In addition to plasma collected on Day 0, 7, and 14 (days of injection), plasma from the rats was independently obtained on Day 3, 10, and 17. During the study described in Example 54, separate rats were repeatedly injected with the triblock copolymer and plasma was collected throughout the study. The concentration of rat IgM from plasma was determined using an ELISA kit according to the manufacturer's instructions (Bethyl Laboratories, Montgomery, Tex.). Results from the ELISA are shown in FIG. 22. The results demonstrate that none of the groups displayed any significant induction of rat IgM antibody, even after multiple injections.

We claim:

1. An anthracycline loaded micelle comprising a multiblock copolymer, wherein said micelle has a drug-loaded inner core, a crosslinked outer core, and a hydrophilic shell, wherein the multiblock copolymer is of formula IX:

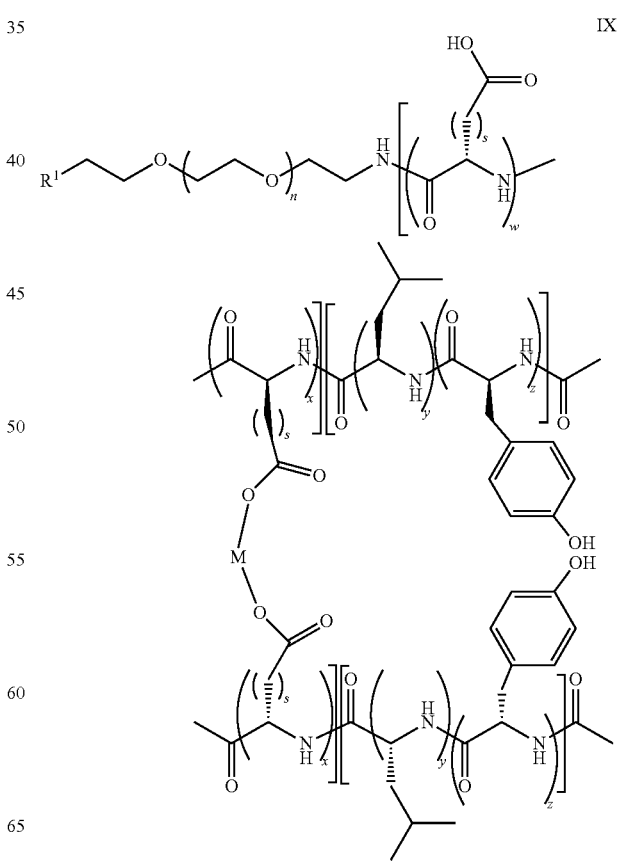

-continued

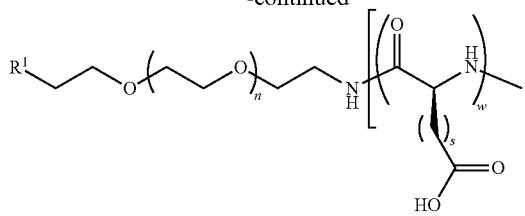

wherein:
each n is independently 10-2500;
each s is independently 1 or 2;
each w is independently 0-30;
each x is independently 1-30;
each y is independently 5-50;
each z is independently 5-50;
M is Fe; and
each $R^1$ is independently —$N_3$—$OCH_3$ or

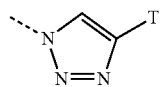

wherein T is a targeting group moiety.

2. The micelle according to claim 1, wherein $R^1$ is —$OCH_3$.

3. The micelle according to claim 2, wherein n is 110-450.

4. The micelle according to claim 2, wherein s is 1.

5. The micelle according to claim 2, wherein y is about 20 and z is about 20.

6. The micelle according to claim 1, wherein $R^1$ is —$N_3$.

7. The micelle according to claim 6, wherein n is 110-450.

8. The micelle according to claim 6, wherein s is 1.

9. The micelle according to claim 6, wherein y is about 20 and z is about 20.

10. The micelle according to claim 1, wherein s is 2.

11. The micelle according to claim 1, wherein the anthracyline is daunorubicin.

* * * * *